United States Patent
Hartman et al.

[11] Patent Number: 5,929,120
[45] Date of Patent: Jul. 27, 1999

[54] GUAINIDINO, FORMAMIDINO, AMINO AND RELATED COMPOUNDS FOR INHIBITING OSTEOCLAST-MEDIATED BONE RESORPTION

[75] Inventors: George D. Hartman, Lansdale; Mark E. Duggan, Schwenksville; William F. Hoffman, Lansdale, all of Pa.; Nathan C. Ihle, Mercer Island, Wash.

[73] Assignee: Merck & Co., Inc., Rahway, N.J.

[21] Appl. No.: 09/015,982

[22] Filed: Jan. 30, 1998

Related U.S. Application Data

[60] Division of application No. 08/714,097, Sep. 26, 1996, Pat. No. 5,741,796, which is a continuation-in-part of application No. 08/250,218, May 27, 1994, abandoned.

[51] Int. Cl.$^6$ .................. A61K 31/155; A61K 31/19; C07C 257/10; C07C 307/02
[52] U.S. Cl. .................. 514/634; 514/567; 514/568; 514/619; 562/430; 562/439; 564/84; 564/170; 564/246; 564/247
[58] Field of Search ................. 514/256, 300, 514/311, 567, 568, 619, 634; 544/332, 333; 546/164, 176, 177, 268.1, 290, 304; 562/430, 439; 564/84, 170, 246, 247

[56] References Cited

FOREIGN PATENT DOCUMENTS 478 328  4/1992  European Pat. Off. .
478 363  4/1992  European Pat. Off. .

*Primary Examiner*—Yogendra N. Gupta
*Attorney, Agent, or Firm*—Richard S. Parr; Melvin Winokur

[57] ABSTRACT

Compounds of the following general structure
X—Y—Z-Aryl-A—B,

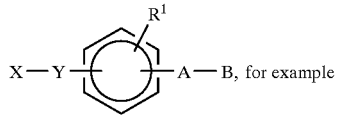

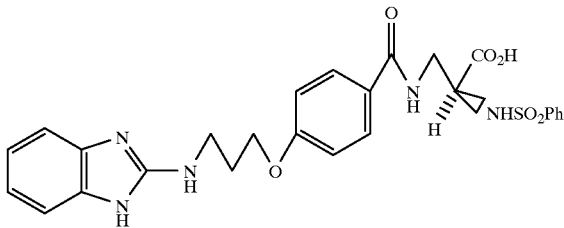

which inhibit osteoclast mediated bone resorption.

14 Claims, No Drawings

GUAINIDINO, FORMAMIDINO, AMINO AND RELATED COMPOUNDS FOR INHIBITING OSTEOCLAST-MEDIATED BONE RESORPTION

CROSS-REFERENCE TO RELATED APPLICATIONS

This application is a divisional of U.S. Ser. No. 08/714,097, filed Sep. 26, 1996, now U.S. Pat. No. 5,741,796 which is a continuation-in-part of U.S. Ser. No. 08/250,218, filed May 27, 1994, now abandoned.

BACKGROUND OF THE INVENTION

This invention relates to compounds for inhibiting bone resorption that is mediated by the action of a class of cells known as osteoclasts.

Osteoclasts are multinucleated cells of up to 400 μm in diameter that resorb mineralized tissue, chiefly calcium carbonate and calcium phosphate, in vertebrates. They are actively motile cells that migrate along the surface of bone. They can bind to bone, secrete necessary acids and proteases and thereby cause the actual resorption of mineralized tissue from the bone.

The pharmacologic activity of these compounds is useful in the treatment of mammals, including man.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment.

All these conditions are characterized by bone loss, resulting from an imbalance between bone resorption (breakdown) and bone formation, which continues throughout life at the rate of about 14% per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

There are currently 20 million people with detectable fractures of the vertebrae due to osteoporosis in the United States. In addition, there are 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Endothelial cells secrete growth factors that are mitogenic for endothelium and can induce formation of new blood vessels (angiogenesis). Angiogenic stimuli cause the elongation or proliferation of endothelial cells and generation of new vessels.

SUMMARY OF THE INVENTION

The present invention involves a compound of the formula

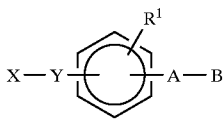

wherein
X is selected from the group consisting of

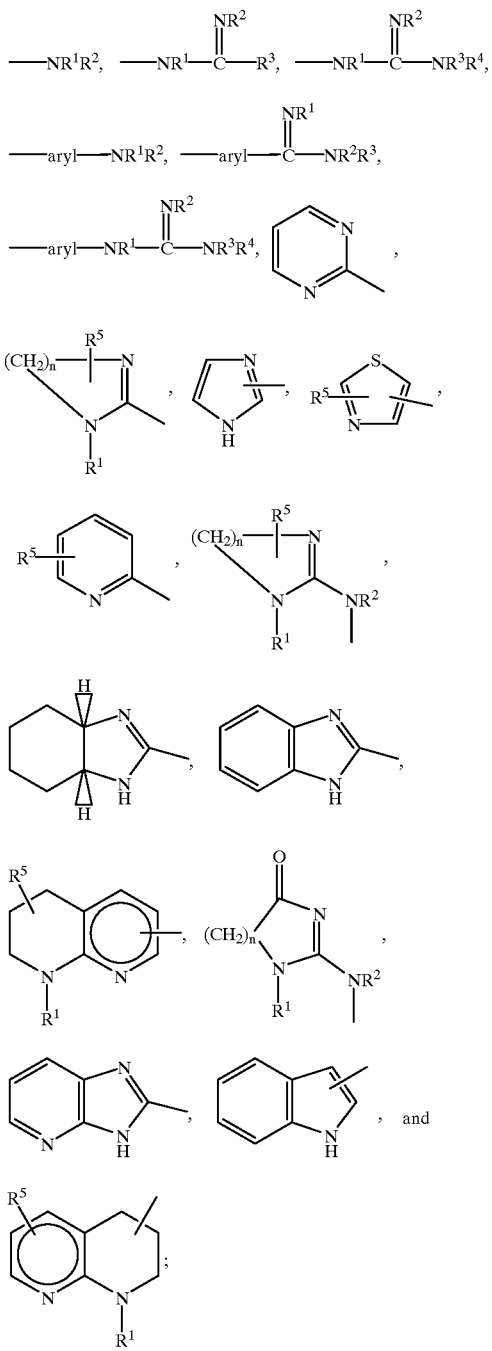

Y is selected from the group consisting of
$C_{1-8}$ alkylene,
$(CH_2)_m$-C≡C$(CH_2)_n$,
$(CH_2)_m CR^1$=$CR^2(CH_2)_n$, $(CH_2)_mCR^1=CR^2(CH_2)_nO$,
$C_{0-8}$ alkylene-$NR^3$—CO—$C_{0-8}$ alkylene,
$C_{0-8}$ alkylene-O—$C_{0-8}$ alkylene,
$C_{0-8}$ alkylene-$NR^3$—$C_{0-8}$ alkylene and
$C_{0-8}$ alkylene-$NR^3$—$C_{0-8}$ alkylene-O—;

A is selected from the group consisting of

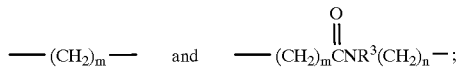

B is

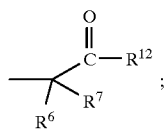

$R^1$, $R^2$, $R^3$ and $R^4$ are each independently selected from the group consisting of
hydrogen,
$C_{1-4}$ alkoxy $C_{0-6}$ alkyl,
$C_{1-4}$ alkoxycarbonyl $C_{0-6}$ alkyl,
$C_{1-6}$ alkylamino $C_{0-8}$ alkyl,
$C_{1-6}$ dialkylamino $C_{0-8}$ alkyl,
amino $C_{0-8}$ alkyl and
aryl $C_{0-8}$ alkyl;

$R^5$ is selected from the group consisting of
hydrogen,
$C_{1-4}$ alkoxy $C_{0-6}$ alkyl,
$C_{1-4}$ alkoxycarbonyl $C_{0-6}$ alkyl,
$C_{1-6}$ alkylamino $C_{0-8}$ alkyl,
$C_{1-6}$ dialkylamino $C_{0-8}$ alkyl,
amino $C_{0-8}$ alkyl,
oxo and aryl $C_{0-8}$ alkyl;

$R^6$ and $R^7$ are each independently selected from the group consisting of:
hydrogen,
$C_{0-6}$ alkylamino $C_{0-6}$ alkyl,
$C_{0-6}$ dialkylamino $C_{0-6}$ alkyl,
aryl $C_{0-6}$ alkyloxycarbonylamino $C_{0-6}$ alkyl,
aryl $C_{0-6}$ alkylsulfonylamino $C_{0-6}$ alkyl and
aryl $C_{0-6}$ alkylcarbonylamino $C_{0-6}$ alkyl;

$R^{12}$ is selected from the group consisting of
hydroxy,
$C_{1-8}$ alkyloxy,
$C_{1-6}$ dialkylaminocarbonylmethoxy and
aryl $C_{1-6}$ dialkylaminocarbonylmethoxy; and m and n are integers independently chosen from 0–6;
provided that when the compound is

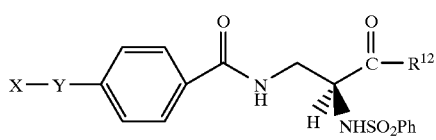

wherein $R^{12}$ is hydroxy or $C_{1-4}$ alkyloxy, then X-Y is not

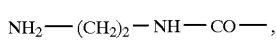

-continued

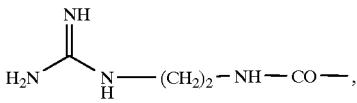

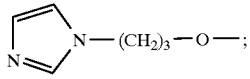 or

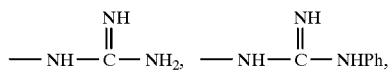

and the pharmaceutically acceptable salts thereof.

In one embodiment is the compound wherein

X is selected from the group consisting of

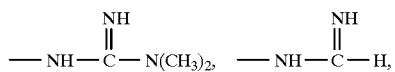

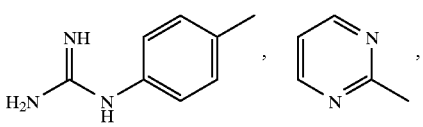

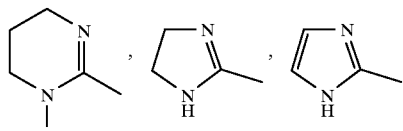

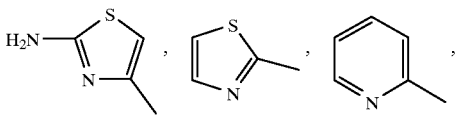

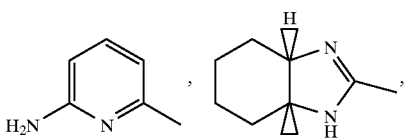

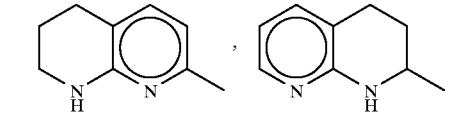

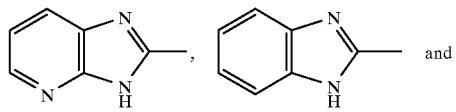 and

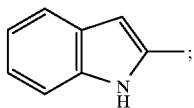

Y is selected from the group consisting of
$C_{1-3}$ alkylene,
—C≡C—,
$C_{0-2}$ alkylene-NH—CO—,
$C_{0-5}$ alkylene-O—$C_{0-1}$ alkylene
—NH—$C_{2-4}$ alkylene and
—NH—$C_{2-4}$ alkylene-O—;
A is selected from the group consisting of

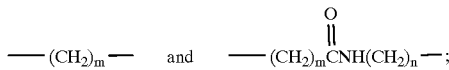

$R^1$ is selected from the group consisting of
hydrogen and $C_{1-4}$ alkoxy;
$R^6$ and $R^7$ are each independently selected from the group consisting of
hydrogen,
—NHCbz,
—NHSO$_2$Ph,
—NHC(O)—Ph and
—N(CH$_3$)—SO$_2$Ph; and
m and n are integers independently chosen from 0–6.
In another embodiment is the compound

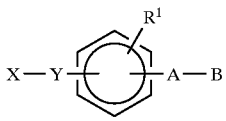

wherein
X is selected from the group consisting of

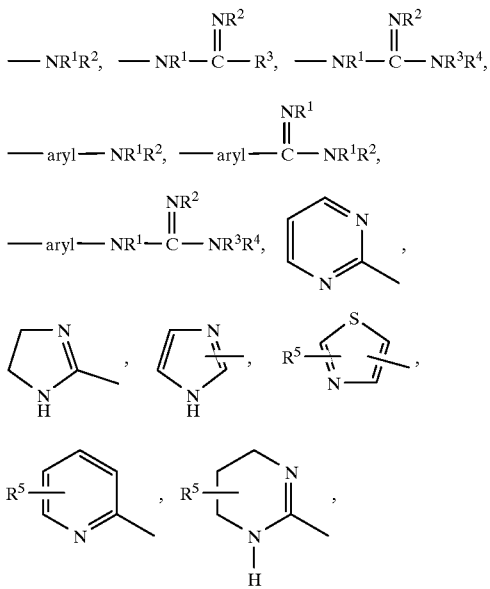

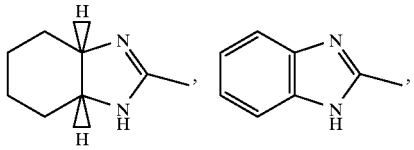

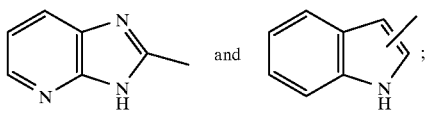
and 

Y is selected from the group consisting of
$C_{1-8}$ alkylene,
$(CH_2)_m$—C≡C—$(CH_2)_n$,
$(CH_2)_m CR^1$=$CR^2(CH_2)_n$,
$(CH_2)_m CR^1$=$CR^2(CH_2)_n O$,
$C_{0-8}$ alkylene-NR$^3$—CO—$C_{0-8}$ alkylene,
$C_{0-8}$ alkylene-O—$C_{0-8}$ alkylene,
$C_{0-8}$ alkylene-NR$^3$-$C_{0-8}$ alkylene and
$C_{0-8}$ alkylene-NR$^3$-$C_{0-8}$ alkylene-O—;
A is selected from the group consisting of

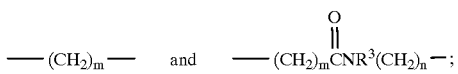

B is

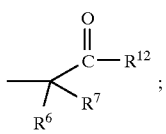

$R^1$, $R^2$, $R^3$ and $R^4$ are each independently selected from the group consisting of
hydrogen,
$C_{1-4}$ alkoxy $C_{0-6}$ alkyl,
$C_{1-4}$ alkoxycarbonyl $C_{0-6}$ alkyl,
$C_{1-6}$ alkylamino $C_{0-8}$ alkyl,
$C_{1-6}$ dialkylamino $C_{0-8}$ alkyl,
amino $C_{0-8}$ alkyl and aryl $C_{0-8}$ alkyl;
$R^5$ is selected from the group consisting of
hydrogen,
$C_{1-4}$ alkoxy $C_{0-6}$ alkyl,
$C_{1-4}$ alkoxycarbonyl $C_{0-6}$ alkyl,
$C_{1-6}$ alkylamino $C_{0-8}$ alkyl,
$C_{1-6}$ dialkylamino $C_{0-8}$ alkyl,
amino $C_{0-8}$ alkyl,
oxo and aryl $C_{0-8}$ alkyl;
$R^6$ and $R^7$ are each independently selected from the group consisting of:
hydrogen,
$C_{0-6}$ alkylamino $C_{0-6}$ alkyl,
$C_{0-6}$ dialkylamino $C_{0-6}$ alkyl,
aryl $C_{0-6}$ alkyloxycarbonylamino $C_{0-6}$ alkyl,
aryl $C_{0-6}$ alkylsulfonylamino $C_{0-6}$ alkyl and
aryl $C_{0-6}$ alkylcarbonylamino $C_{0-6}$ alkyl;
$R^{12}$ is selected from the group consisting of
hydroxy,
$C_{1-8}$ alkyloxy,
$C_{1-6}$ dialkylaminocarbonylmethoxy and
aryl $C_{1-6}$ dialkylaminocarbonylmethoxy; and m and n are integers independently chosen from 0–6; provided that when the compound is

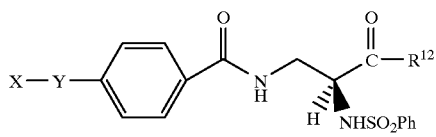

wherein $R^{12}$ is hydroxy or $C_{1-4}$ alkyloxy, then X-Y is not

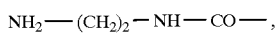

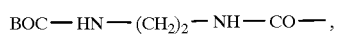

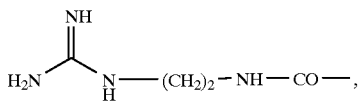

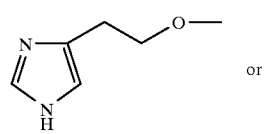

or

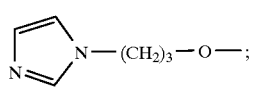

and the pharmaceutically acceptable salts thereof.

In a class of this embodiment is the compound wherein

X is selected from the group consisting of

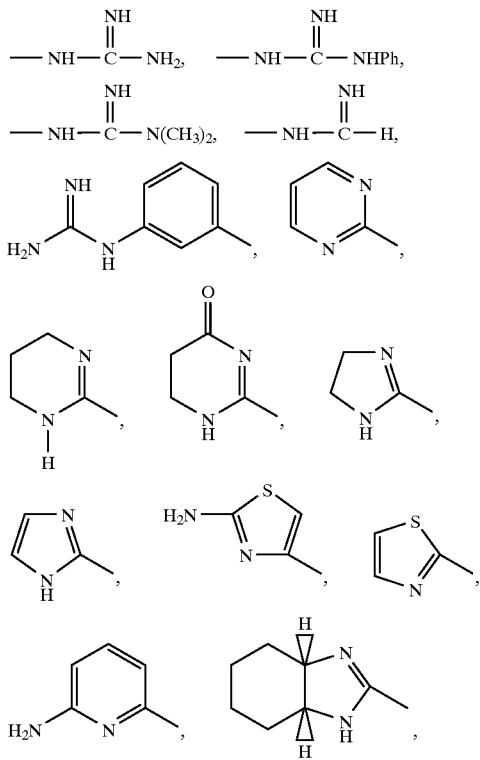

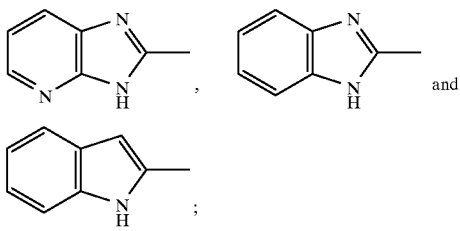

Y is selected from the group consisting of
$C_{1-2}$ alkylene,
—C≡C—,
$C_{0-2}$ alkylene-NH—CO—,
$C_{0-5}$ alkylene-O—$C_{0-1}$ alkylene and
—NH—$C_{2-4}$ alkylene-O—;

A is selected from the group consisting of

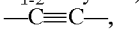

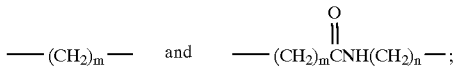

$R^1$ is selected from the group consisting of
hydrogen and
$C_{1-4}$ alkoxy;

$R^6$ and $R^7$ are each independently selected from the group consisting of
hydrogen,
—NHCbz,
—NHSO$_2$Ph,
—NHC(O)—Ph and
—N(CH$_3$)—SO$_2$Ph; and m and n are integers independently chosen from 0–1.

Examples of this class are compounds selected from the group of:

4-(2-Guanidoethyloxy)phenylcarbonyl-2(S)-benzyloxycarbonylamino-β-alanine,
4-(2-Guanidoethyloxy)phenylcarbonyl-2(S)-phenylsulfonylamino-β-alanine,
2(S)-Phenylsulfonylamino-3-[4-(4-guanidobutyloxy)phenyl]-propionic acid,
2(S)-(N-Benzyloxycarbonylamino)-3-[4-(5-guanidopentyloxy)phenyl]-propionic acid,
4-(3-Guanidinopropyloxy)benzoyl-2-(S)-phenylsulfonylamino-β-alanine,
4-(3-Formamidinopropyloxy)benzoyl-2-(S)-phenylsulfonylamino-β-alanine,
3-Methoxy-4-(3-guanidinopropyloxy)benzoyl-2(S)-phenylsulfonyl-amino-β-alanine,
3-Methoxy-4-(3-aminopropyloxy)benzoyl-2(S)-phenylsulfonylamino-β-alanine,
3-(3-Guanidinopropyloxy)benzoyl-2(S)-phenylsulfonylamino-β-alanine,
4-[2-(N-Phenylguanidino)ethyloxy]benzoyl-2(S)-phenylsulfonylamino-β-alanine,
4-[2-(N,N-Dimethylguanidino)ethyloxy]benzoyl-2(S)-phenylsulfonyl-amino-β-alanine,
4-(Guanidinophen-3-yloxy)benzoyl-2(S)-phenylsulfonylamino-β-alanine,
4-[2-(Guanidino)ethyloxymethyl]benzoyl-2(S)-phenylsulfonylamino-β-alanine,
3-[2-(Guanidino)ethylaminocarbonyl]benzoyl-2(S)-phenylsulfonylamino-β-alanine,
4-[2-(2-Aminothiazol-4-yl)ethyloxy]benzoyl-2(S)-phenylsulfonylamino-β-alanine t-butyl ester, 4-[2-(2-Aminothiazol-4-yl)ethyloxy]benzoyl-2(S)-phenylsulfonylamino-β-alanine, 4-[2-(N-(2-Imidazolin-2-yl)aminoethyloxy]benzoyl-2(S)-phenylsulfonyl-amino-β-alanine, 2(S)-Phenylsulfonylamino-3-[4-(4-(N-imidazolin-2-yl)aminobutyloxy)-phenyl]propionic acid, 4-[2-[N-[Cis-3a,4,5,6,7,7a-Hexahydro-1H-benzimidazol-2-yl]amino]-ethyloxybenzoyl-2(S)-phenylsulfonylamino-β-alanine, 4-[2-(Pyrimidin-2-ylamino)ethyloxy]benzoyl-2(S)-phenylsulfonylamino-β-alanine, 4-[2-(3,4,5,6-Tetrahydropyrimidin-2-ylamino)ethyloxy]benzoyl-2(S)-phenylsulfonylamino-β-alanine, 4-[2-(2-Aminothiazol-4-yl)ethyl]benzoyl-2(S)-phenylsulfonylamino-β-alanine t-butyl ester, 4-[2-(2-Aminothiazol-4-yl)ethyl]benzoyl-2(S)-phenylsulfonylamino-β-alanine, 4-[2(S)-(N-(2-Imidazolin-2-yl)amino)propyloxy]benzoyl-2(S)-phenyl-sulfonylamino-β-alanine, 4-[2-(Imidazol-2-yl)ethyl]benzoyl-2(S)-phenylsulfonylamino-β-alanine, 4-[2-(Thiazol-2-ylamino)ethyloxy]benzoyl-2(S)-phenylsulfonylamino-β-alanine, 4-[2-(Pyrimidin-2-ylamino)ethyloxy]benzoyl-2(S)-benzyloxycarbonyl-amino-β-alanine, 4-[2-(3,4,5,6-Tetrahydropyrimidin-2-ylamino)ethyloxy]benzoyl-2(S)-benzyloxycarbonylamino-β-alanine, Methyl 2(S)-benzoylamino-3-[4-(4-pyrimidin-2-ylaminobutyloxy)-phenyl]propionate, 2(S)-Benzoylamino-3-[4-(4-pyrimidin-2-ylainino)butyloxy)phenyl]-propionic acid, 2(S)-Benzoylamino-3-[4-(4-(3,4,5,6-tetrahydropyrimidin-2-ylamino)-butyloxy)phenyl]propionic acid, 4-[2-(Pyrimidin-2-ylamino)ethyloxy]benzoyl-2(S)-N-methyl-N-phenylsulfonylamino-β-alanine t-butyl ester, 4-[2-(Pyrimidin-2-ylamino)ethyloxy]benzoyl-2(S)-N-methyl-N-phenylsulfonylamino-β-alanine, 4-[2-(3,4,5,6-Tetrahydropyrimidin-2-ylamino)ethyloxy]benzoyl-2(S)-N-methyl-N-phenylsulfonylamino-β-alanine, 4-[2-(N-(5,6-Dihydro-4-keto-1(H)-pyrimidin-2-yl)amino)ethyloxy]-benzoyl-2(S)-phenylsulfonylamino-β-alanine, 4-(2-Aminopyridin-6-ylethynyl)benzoyl-2(S)-phenylsulfonylamino-β-alanine t-butyl ester, 4-(2-Aminopyridin-6-ylethynyl)benzoyl-2(S)-phenylsulfonylamino-β-alanine, 4-[2-(2-Aminopyridin-6-yl)ethyl]benzoyl-2(S)-phenylsulfonylamino-β-alanine, 4-[2-(2-Aminopyridin-6-yl)ethyloxy]benzoyl-2(S)-phenylsulfonylamino-β-alanine t-butyl ester, 4-[2-(2-Aminopyridin-6-yl)ethyloxy]benzoyl-2(S)-phenylsulfonylamino-β-alanine, 4-[2-(Indol-2-yl)ethyloxy]benzoyl-2(S)-phenylsulfonylamino-β-alanine, methyl ester, 4-[2-(Indol-2-yl)ethyloxy]benzoyl-2(S)-phenylsulfonylamino-β-alanine, 4-[2-(1H-Imidazo [4,5-6]pyridin-2-yl)ethenyl]benzoyl-2(S)-phenylsulfonylamino-β-alanine t-butyl ester, 4-[2-(1H-Imidazo[4,5-b]pyridin-2-yl)ethenyl]benzoyl-2(S)-phenylsulfonylamino-β-alanine, 4-[2-(1H-Imidazo[4,5-b]pyridin-2-yl)ethyl]benzoyl-2(S)-phenylsulfonylamino-β-alanine, 4-[2-(1,8-Naphthyidin-7-yl)ethenyl]benzoyl-2(S)-phenylsulfonylamino-β-alanine t-butylester, 4-[2-(1,2,3,4-Tetrahydro-1,8-naphthyridin-7-yl)ethyl]benzoyl-2(S)-phenylsulfonylamino-β-alanine t-butyl ester, 4-[2-(1,2,3,4-Tetrahydro-1,8-naphthyridin-7yl)ethyl]benzoyl-2(S)-phenylsulfonylamino-β-alanine, 4-[2-(1,8-Naphthyridin-7-yl)ethenyl]benzoyl-2(S)-phenylsulfonylamino-β-alanine ethyl ester, 4-[2-(1,2,3,4-Tetrahydro-1,8-naphthyridin-7-yl)ethyl]benzoyl-2(S)-phenylsulfonylamino-β-alanine ethyl ester, 4-[2-(1,2,3,4-Tetrahydro-1,8 naphthyridin-7-yl)ethyl]benzoyl-2(S)-[1 (S)10-camphorsulfonylamido] β-alanine ethyl ester, 4-[2-(1,2,3,4-Tetrahydro-1,8 naphthyridin-7-yl)ethyl]benzoyl-2(S)-[1(S)10-camphorsulfonylamido] β-alanine, 4-[(3-Aminoisoquinolin-1-yl)ethynyl]benzoyl-2(S)-phenylsulfonamido-β-alanine ethyl ester, 4-[(3-Aminoisoquinolin-1-yl)ethynyl]benzoyl-2(S)-phenylsulfonamido-β-alanine trifluoroacetate, 4-[2-(3-Aminoisoquinolin-1-yl)ethyl]benzoyl-2(S)-phenylsulfonamido-β-alanine trifluoroacetate, 4-[3-[N-(1H-Benzimidazo-2-yl)amino]propoxy]benzoyl-2(S)-phenylsulfonylamino-β-alanine t-butyl ester, and 4-[3-[N-(1H-Benzimidazol-2-yl)amino]propoxy]benzoyl-2(S)-phenylsulfonylamino -β-alanine.

Illustrative of the embodiment is a method of inhibiting the bone resorption activity of mammalian osteoclast cells comprising the step of administering a pharmacologically effective amount of the compound.

A further illustration of the embodiment is a composition for inhibiting bone resorption activity of mammalian osteoclast cells comprising a pharmacologically effective amount of the compound and a pharmaceutically acceptable carrier.

Exemplifying the class is a method of inhibiting the bone resorption activity of mammalian osteoclast cells comprising the step of administering a pharmacologically effective amount of the compound.

Further exemplifying the class is a composition for inhibiting bone resorption activity of mammalian osteoclast cells comprising a pharmacologically effective amount of the compound and a pharmaceutically acceptable carrier.

Also included within the scope of the invention is a method of inhibiting the bone resorption activity of mammalian osteoclast cells comprising the step of administering a pharmacologically effective amount of a compound of the formula:

wherein:
Aryl is a 6-membered aromatic ring containing 0, 1, 2 or 3 N atoms and either unsubstituted or substituted with one or more groups chosen from $R^1$ and $R^2$;

X is selected from

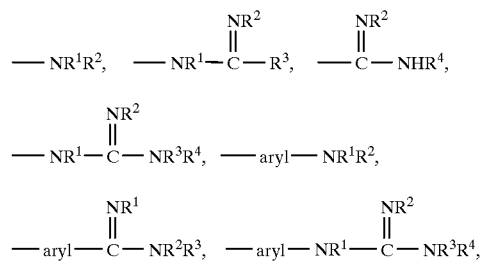

or a 4- to 10-membered mono- or polycyclic aromatic or nonaromatic ring system containing 0, 1, 2, 3 or 4 heteroatoms selected from N, O and S and either unsubstituted or substituted with $R^{13}$, $R^{14}$, $R^{15}$ or $R^{16}$;

Y is selected from the group consisting of
$C_{0-8}$ alkylene,
$C_{3-10}$ cycloalkyl,
$C_{0-8}$ alkylene-$NR^3$—CO—$C_{0-8}$ alkylene,
$C_{0-8}$ alkylene-$CONR^3$—$C_{0-8}$ alkylene,
$C_{0-8}$ alkylene-O—$C_{0-8}$ alkylene,
$C_{0-8}$ alkylene-$NR^1$—$C_{0-8}$ alkylene,
$C_{0-8}$ alkylene-$S(O)_{0-2}$—$C_{0-8}$ alkylene,
$C_{0-8}$ alkylene-$SO_2$—$NR^3$—$C_{0-8}$ alkylene,
$C_{0-8}$ alkylene-$NR^3$—$SO_2$—$C_{0-8}$ alkylene,
$C_{0-8}$ alkylene-CO—$C_{0-8}$ alkylene,
$(CH_2)_{0-6}$ aryl$(CH_2)_{0-6}$,
$(CH_2)_{0-6}$ aryl-CO—$(CH_2)_{0-6}$,
$(CH_2)_{0-6}$ aryl-CO—$NR^3$—$(CH_2)_{0-6}$,
$(CH_2)_{0-6}$ aryl$NR^3CO(CH_2)_{0-6}$

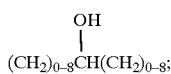

Z and A are each independently selected from the group consisting of

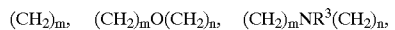

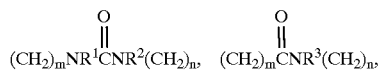

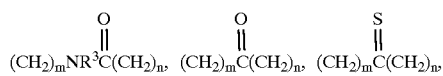

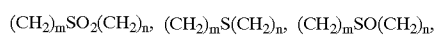

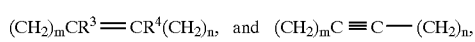

where m and n are integers independently chosen from 0–6;
B is selected from

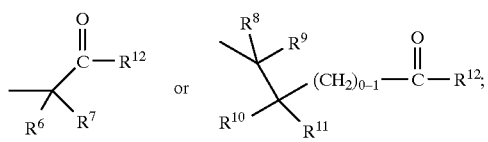

$R^1$, $R^2$, $R^3$ and $R^4$ are each independently selected from the group consisting of
hydrogen,
halogen,
$C_{1-10}$ alkyl,
aryl $C_{0-8}$ alkyl,
amino $C_{0-8}$ alkyl,
$C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
aryl $C_{0-6}$ alkylamino $C_{0-6}$ alkyl,
$C_{1-4}$ alkoxyamino $C_{0-8}$ alkyl,
hydroxy $C_{1-6}$ alkylamino $C_{0-8}$ alkyl,
$C_{1-4}$ alkoxy $C_{0-6}$ alkyl,
carboxy $C_{0-6}$ alkyl,
$C_{1-4}$ alkoxycarbonyl $C_{0-6}$ alkyl,
carboxy $C_{0-6}$ alkyloxy,
hydroxy $C_{1-6}$ alkylamino $C_{0-6}$ alkyl,
hydroxy $C_{0-6}$ alkyl,

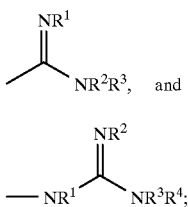

$R^6$, $R^7$, $R^8$, $R^9$, $R^{10}$, and $R^{11}$ are each independently selected from
hydrogen,
fluorine,
$C_{1-8}$ alkyl,
hydroxyl,
hydroxy $C_{1-6}$ alkyl,
carboxy $C_{0-6}$ alkyl,
$C_{1-6}$ alkyloxy,
$C_{1-6}$ alkylcarbonyl,
aryl $C_{0-6}$ alkylcarbonyl,
$C_{0-6}$ alkylcarbonyloxy,
aryl $C_{0-6}$ alkylcarbonyloxy,
$C_{1-6}$ alkylaminocarbonyloxy,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl,
aryl $C_{0-6}$ alkylcarbonyl $C_{0-6}$ alkyl,
$C_{1-6}$ alkylthiocarbonylamino $C_{0-6}$ alkyl, and
aryl $C_{0-6}$ alkylthiocarbonylamino $C_{0-6}$ alkyl wherein the alkyl, aryl, or N atoms may be unsubstituted or substituted with one or more substituents selected from $R^1$ and $R^2$;

$R^{12}$ is selected from
hydroxy,
$C_{1-8}$ alkyloxy,
aryl $C_{0-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy,
$C_{1-6}$ dialkylaminocarbonylmethyloxy,
aryl $C_{1-6}$ dialkylaminocarbonylmethyloxy or
an L- or D-amino acid joined by an amide linkage and wherein the carboxylic acid moiety of said amino acid is as the free acid or is esterified by $C_{1-6}$ alkyl; and $R^{13}$, $R^{14}$, $R^{15}$ and $R^{16}$ are each independently selected from the group consisting of
hydrogen,
$C_{1-10}$ alkyl,
aryl $C_{0-8}$ alkyl,
oxo,
thio, amino $C_{0-8}$ alkyl,
$C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
aryl $C_{0-6}$ alkylamino $C_{0-6}$ alkyl,
$C_{1-4}$ alkoxyamino $C_{0-8}$ alkyl,
hydroxy $C_{1-6}$ alkylamino $C_{0-8}$ alkyl,
$C_{1-4}$ alkoxy $C_{0-6}$ alkyl,
carboxy $C_{0-6}$ alkyl,
$C_{1-4}$ alkoxycarbonyl $C_{0-6}$ alkyl,
carboxy $C_{0-6}$ alkyloxy,
hydroxy $C_{1-6}$ alkylamino $C_{0-6}$ alkyl,
hydroxy $C_{0-6}$ alkyl,

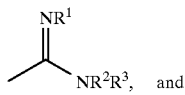

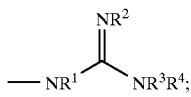

and the pharmaceutically acceptable salts thereof.

In one embodiment of the method, compounds have the formula:

X—Y—Z-Aryl-A—B wherein:

Aryl is a 6-membered aromatic ring containing 0, 1, 2 or 3 N atoms and either unsubstituted or substituted with one or more groups chosen from $R^1$ and $R^2$;

X is selected from

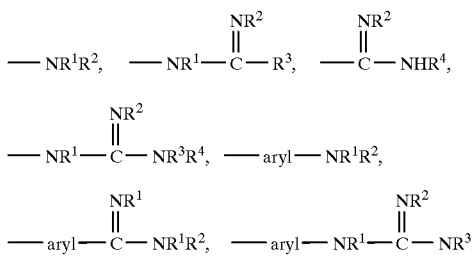

or a 4- to 10-membered mono- or polycyclic aromatic or nonaromatic ring system containing 0, 1, 2, 3 or 4 heteroatoms selected from N, O and S and either unsubstituted or substituted with $R^{13}$, $R^{14}$, $R^{15}$ or $R^{16}$;

Y is selected from the group consisting of
$C_{0-8}$ alkylene,
$C_{3-10}$ cycloalkyl,
$C_{0-8}$ alkylene-$NR^3$—CO—$C_{0-8}$ alkylene,
$C_{0-8}$ alkylene-$CONR^3$—$C_{0-8}$ alkylene,
$C_{0-8}$ alkylene-O—$C_{0-8}$ alkylene,
$C_{0-8}$ alkylene-$NR^1$—$C_{0-8}$ alkylene,
$C_{0-8}$ alkylene-$S(O)_{0-2}$—$C_{0-8}$ alkylene,
$C_{0-8}$ alkylene-$SO_2$—$NR^3$—$C_{0-8}$ alkylene,
$C_{0-8}$ alkylene-$NR^3$—$SO_2$—$C_{0-8}$ alkylene,
$C_{0-8}$ alkylene-CO—$C_{0-8}$ alkylene,
$(CH_2)_{0-6}$ aryl$(CH_2)_{0-6}$,
$(CH_2)_{0-6}$ aryl-CO—$(CH_2)_{0-6}$,
$(CH_2)_{0-6}$ aryl-CO—NH—$(CH_2)_{0-6}$, and

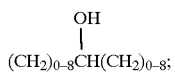

Z and A are each independently selected from the group consisting of

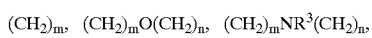

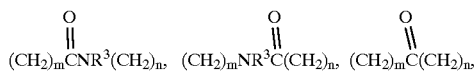

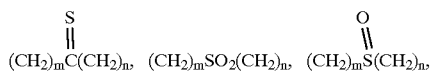

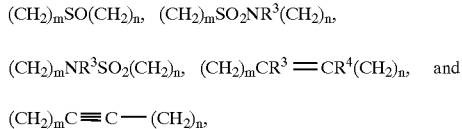

where m and n are integers independently chosen from 0–6;
B is selected from

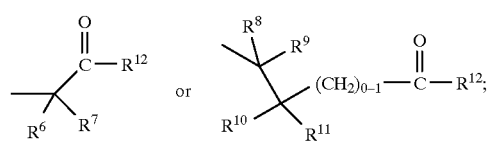

$R^1$, $R^2$, $R^3$ and $R^4$ are each independently selected from the group consisting of
hydrogen,
halogen,
$C_{1-10}$ alkyl,
aryl $C_{0-8}$ alkyl,
amino $C_{0-8}$ alkyl,
$C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
aryl $C_{0-6}$ alkylamino $C_{0-6}$ alkyl,
$C_{1-4}$ alkoxyamino $C_{0-8}$ alkyl,
hydroxy $C_{1-6}$ alkylamino $C_{0-8}$ alkyl,
$C_{1-4}$ alkoxy $C_{0-6}$ alkyl,
carboxy $C_{0-6}$ alkyl,
$C_{1-4}$ alkoxycarbonyl $C_{0-6}$ alkyl,
carboxy $C_{0-6}$ alkyloxy,
hydroxy $C_{1-6}$ alkylamino $C_{0-6}$ alkyl,
hydroxy $C_{0-6}$ alkyl,

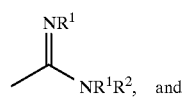

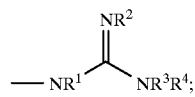

$R^6$, $R^7$, $R^8$, $R^9$, $R^{10}$, and $R^{11}$ are each independently selected from hydrogen,
fluorine,
$C_{1-8}$ alkyl,
hydroxyl,
hydroxy $C_{1-6}$ alkyl,
carboxy $C_{0-6}$ alkyl,
$C_{1-6}$ alkyloxy,
$C_{1-6}$ alkylcarbonyl,
aryl $C_{0-6}$ alkylcarbonyl,
$C_{1-6}$ alkylcarbonyloxy,
aryl $C_{0-6}$ alkylcarbonyloxy,
$C_{1-6}$ alkylaminocarbonyloxy,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl,
aryl $C_{0-6}$ alkylcarbonyl $C_{0-6}$ alkyl,
$C_{1-6}$ alkylthiocarbonylamino $C_{0-6}$ alkyl, and
aryl $C_{0-6}$ alkylthiocarbonylamino $C_{0-6}$ alkyl
wherein the alkyl or aryl groups may be unsubstituted or substituted with one or more substituents selected from $R^1$ and $R^2$;

$R^{12}$ is selected from
hydroxy,
$C_{1-8}$ alkyloxy,
aryl $C_{0-6}$ alkyloxy,
$C_{1-8}$ alkylcarbonyloxy $C_{1-4}$ alkyloxy,
aryl $C_{1-8}$ alkylcarbonyloxy $C_{1-4}$ alkyloxy,
$C_{1-6}$ dialkylaminocarbonylmethyloxy,
aryl $C_{1-6}$ dialkylarninocarbonylmethyloxy or
an L- or D-amino acid joined by an amide linkage and wherein the carboxylic acid moiety of said amino acid is as the free acid or is esterified by $C_{1-6}$ alkyl; and $R^{13}$, $R^{14}$, $R^{15}$ and $R^{16}$ are each independently selected from the group consisting of
hydrogen,
$C_{1-10}$ alkyl,
aryl $C_{0-8}$ alkyl,
oxo,
thio,
amino $C_{0-8}$ alkyl,
$C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
aryl $C_{0-6}$ alkylamino $C_{0-6}$ alkyl,
$C_{1-4}$ alkoxyamino $C_{0-8}$ alkyl,
hydroxy $C_{1-6}$ alkylamino $C_{0-8}$ alkyl,
$C_{1-4}$ alkoxy $C_{0-6}$ alkyl,
carboxy $C_{0-6}$ alkyl,
$C_{1-4}$ alkoxycarbonyl $C_{0-6}$ alkyl,
carboxy $C_{0-6}$ alkyloxy,
hydroxy $C_{1-6}$ alkylamino $C_{0-6}$ alkyl,
hydroxy $C_{0-6}$ alkyl,

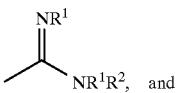

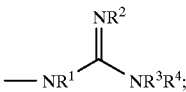

and the pharmaceutically acceptable salts thereof.

In a class of this embodiment, the compounds have the formula wherein Aryl is a 6-membered aromatic ring containing 0, 1 or 2 N atoms and either unsubstituted or substituted with one or more groups chosen from $R^1$ and $R^2$;

X is defined as above;

Y is selected from
$C_{0-8}$ alkylene,
$C_{0-8}$ alkylene-$NR^3$—CO—$C_{0-8}$ alkylene,
$C_{0-8}$ alkylene-$CONR^3$—$C_{0-8}$ alkylene,
$C_{0-8}$ alkylene-O—$C_{0-8}$ alkylene,
$C_{0-8}$ alkylene-$NR^1$—$C_{0-8}$ alkylene,
$C_{0-8}$ alkylene-$S(O)_{0-2}$—$C_{0-8}$ alkylene,
$C_{0-8}$ alkylene-$SO_2$—$NR^3$—$C_{0-8}$ alkylene, or
$C_{0-6}$ alkylene-aryl-$C_{0-6}$ alkylene;

Z and A are each independently selected from the group consisting of

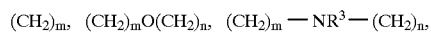

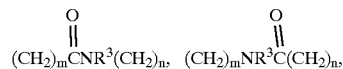

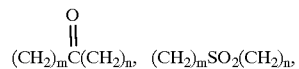

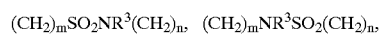

and 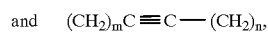

wherein m and n are independently chosen from 0–6;

B is defined as above;

$R^1$, $R^2$, $R^3$ and $R^4$ are each independently selected from
hydrogen,
$C_{1-10}$ alkyl,
aryl $C_{0-8}$ alkyl,
amino $C_{0-8}$ alkyl,
$C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
$C_{1-4}$ alkyloxy $C_{0-6}$ alkyl,
carboxy $C_{0-6}$ alkyl,
$C_{1-4}$ alkyloxycarbonyl $C_{0-6}$ alkyl,
carboxy $C_{0-6}$ alkyloxy,
hydroxy $C_{0-6}$ alkyl,

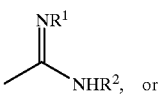

-continued

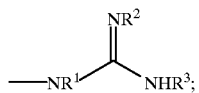

$R^6$, $R^7$, $R^8$, $R^9$, $R^{10}$ and $R^{11}$ are independently selected from the group consisting of
hydrogen,
hydroxyl,
fluorine,
$C_{1-8}$ alkyl,
$C_{3-8}$ cycloalkyl,
aryl $C_{0-6}$ alkyl,
$C_{0-6}$ alkylamino $C_{0-6}$ alkyl,
$C_{0-6}$ dialkylamino $C_{0-6}$ alkyl,
$C_{1-8}$ alkylsulfonylamino $C_{0-6}$ alkyl,
aryl $C_{0-6}$ alkylsulfonylamino $C_{0-6}$ alkyl,
$C_{1-8}$ alkyloxycarbonylamino $C_{0-8}$ alkyl,
aryl $C_{0-8}$ alkyloxycarbonylamino $C_{0-8}$ alkyl,
$C_{1-8}$ alkylcarbonylamino $C_{0-6}$ alkyl,
aryl $C_{0-6}$ alkylcarbonylamino $C_{0-6}$ alkyl,
$C_{0-8}$ alkylaminocarbonylamino $C_{0-6}$ alkyl,
aryl $C_{0-8}$ alkylaminocarbonylamino $C_{0-6}$ alkyl,
$C_{0-8}$ alkylaminosulfonylamino $C_{0-6}$ alkyl,
aryl $C_{0-8}$ alkylaminosulfonylamino $C_{0-6}$ alkyl,
$C_{1-6}$ alkylsulfonyl $C_{0-6}$ alkyl,
aryl $C_{0-6}$ alkylsulfonyl $C_{0-6}$ alkyl,
$C_{1-6}$ alkylcarbonyl $C_{0-6}$ alkyl, and
aryl $C_{0-6}$ alkylcarbonyl $C_{0-6}$ alkyl;

$R^{12}$ is selected from the group consisting of
hydroxy,
$C_{1-8}$ alkyloxy,
aryl $C_{0-6}$ alkyloxy,
$C_{1-8}$ alkylcarbonyloxy $C_{1-4}$ alkyloxy, and
aryl $C_{1-8}$ alkylcarbonyloxy $C_{1-4}$ alkyloxy; and $R^{13}$, $R^{14}$, $R^{15}$ and $R^{16}$ are each independently selected from
hydrogen,
$C_{1-10}$ alkyl,
aryl $C_{0-8}$ alkyl,
oxo,
amino $C_{0-8}$ alkyl,
$C_{1-3}$ acylamino $C_{0-8}$ alkyl,
$C_{1-6}$ alkylamino $C_{0-8}$ alkyl,
$C_{1-6}$ dialkylamino $C_{0-8}$ alkyl,
$C_{1-4}$ alkyloxy $C_{0-6}$ alkyl,
carboxy $C_{0-6}$ alkyl,
$C_{1-4}$ alkyloxycarbonyl $C_{0-6}$ alkyl,
carboxy $C_{0-6}$ alkyloxy,
hydroxy $C_{0-6}$ alkyl,

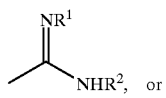

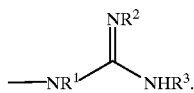

In a subclass of the class is the method wherein the compound has the formula:

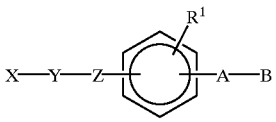

wherein:

X is selected from the group consisting of

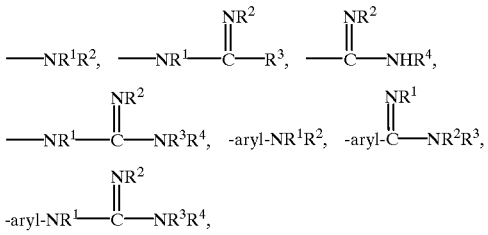

or a 5- to 10-membered aromatic or nonaromatic ring system containing 0, 1, 2, 3 or 4 heteroatoms selected from N and S and either unsubstituted or substituted with $R^{13}$, $R^{14}$, $R^{15}$ or $R^{16}$;

Y is selected from the group consisting of
$C_{0-8}$ alkylene,
$C_{0-8}$ alkylene-$NR^3$—CO—$C_{0-8}$ alkylene,
$C_{0-8}$ alkylene-$CONR^3$—$C_{0-8}$ alkylene,
$C_{0-8}$ alkylene-O—$C_{0-8}$ alkylene,
$C_{0-8}$ alkylene-$NR^1$—$C_{0-8}$ alkylene and
$C_{0-8}$ alkylene-$S(O)_{0-2}$—$C_{0-8}$ alkylene;

Z and A are each independently selected from the group consisting of

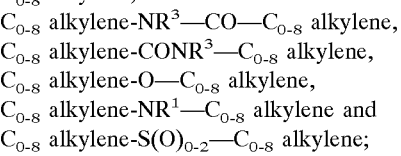

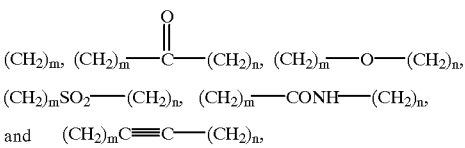

wherein m and n are independently chosen from 0–6;

B is defined as above;

$R^1$, $R^2$, $R^3$ or $R^4$, are each independently selected from the group consisting of
hydrogen,
$C_{1-10}$ alkyl,
aryl $C_{0-8}$ alkyl,
$C_{1-4}$ alkyloxy $C_{0-6}$ alkyl,
$C_{1-4}$ alkoxycarbonyl $C_{0-6}$ alkyl,
carboxy $C_{0-6}$ alkyl,
hydroxy $C_{0-6}$ alkyl,
amino $C_{0-8}$ alkyl,
$C_{1-6}$ alkylamino $C_{0-8}$ alkyl,
$C_{1-6}$ dialkylamino $C_{0-8}$ alkyl,

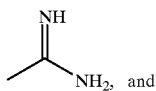

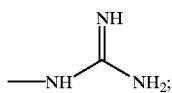

$R^{13}$, $R^{14}$, $R^{15}$ or $R^{16}$, are each independently selected from the group consisting of
hydrogen,
$C_{1-10}$ alkyl,
aryl $C_{0-8}$ alkyl,
oxo,
$C_{1-4}$ alkyloxy $C_{0-6}$ alkyl,
$C_{1-4}$ alkoxycarbonyl $C_{0-6}$ alkyl,
carboxy $C_{0-6}$ alkyl,
hydroxy $C_{0-6}$ alkyl,
amino $C_{0-8}$ alkyl,
$C_{1-6}$ alkylamino $C_{0-8}$ alkyl,
$C_{1-6}$ dialkylamino $C_{0-8}$ alkyl,

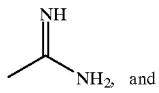

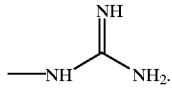

In a group of this subclass is a method wherein X of the compound is selected from the group consisting of

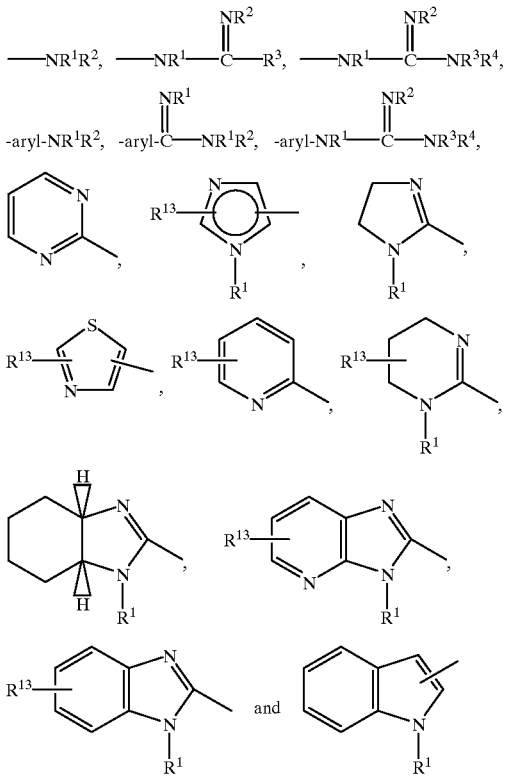

Y is selected from the group consisting of
$C_{0-8}$ alkylene,
$C_{0-8}$ alkylene-$NR^3$—CO—$C_{0-8}$ alkylene,
$C_{0-8}$ alkylene-O—$C_{0-8}$ alkylene and
$C_{0-8}$ alkylene-$NR^1$—$C_{0-8}$ alkylene;

Z and A are each independently selected from the group consisting of

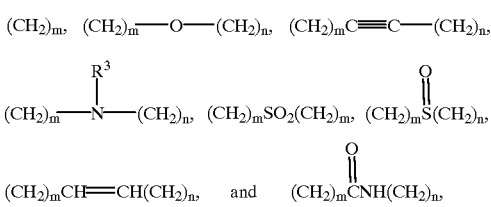

wherein m and n are independently chosen from 0–6;
B is

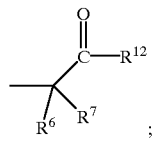

$R^1$, $R^2$, $R^3$ and $R^4$ are each independently selected from the group consisting of
hydrogen,
$C_{1-4}$ alkoxy $C_{0-6}$ alkyl,
$C_{1-4}$ alkoxycarbonyl $C_{0-6}$ alkyl,
$C_{1-6}$ alkylamino $C_{0-8}$ alkyl,
$C_{1-6}$ dialkylamino $C_{0-8}$ alkyl,
amino $C_{0-8}$ alkyl and
aryl $C_{0-8}$ alkyl;

$R^6$ and $R^7$ are each independently selected from the group consisting of:
hydrogen,
$C_{0-6}$ alkylamino $C_{0-6}$ alkyl,
$C_{0-6}$ dialkylamino $C_{0-6}$ alkyl,
aryl $C_{0-6}$ alkyloxycarbonylamino $C_{0-6}$ alkyl,
aryl $C_{0-6}$ alkylsulfonylamino $C_{0-6}$ alkyl and
aryl $C_{0-6}$ alkylcarbonylamino $C_{0-6}$ alkyl;

$R^{12}$ is selected from the group consisting of
hydroxy and
$C_{1-8}$ alkyloxy; and $R^{13}$ is selected from the group consisting of
hydrogen,
$C_{1-4}$ alkoxy $C_{0-6}$ alkyl,
$C_{1-4}$ alkoxycarbonyl $C_{0-6}$ alkyl,
$C_{1-6}$ alkylamino $C_{0-8}$ alkyl,
$C_{1-6}$ dialkylamino $C_{0-8}$ alkyl,
amino $C_{0-8}$ alkyl,
oxo and
aryl $C_{0-8}$ alkyl.

In a subgroup of this group is a method wherein X of the compound is selected from the group consisting of

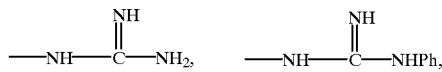

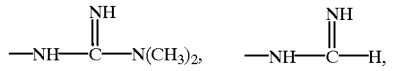

-continued

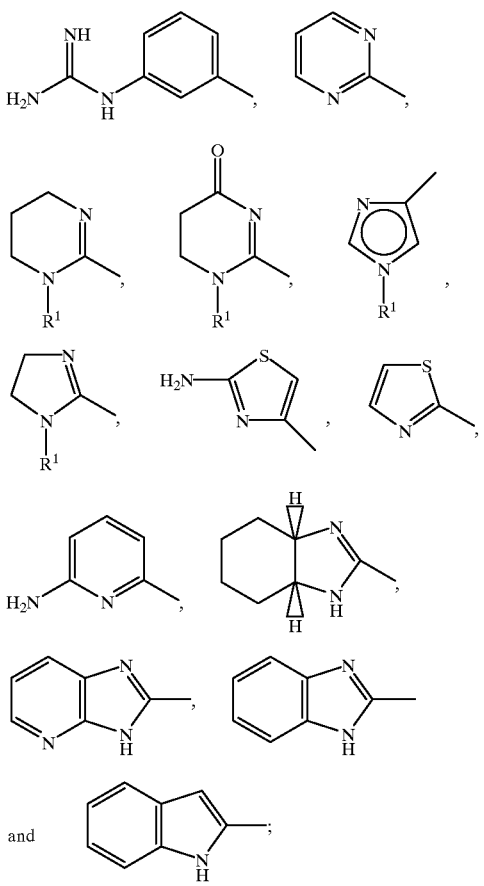

Y is selected from the group consisting of
C$_{0-2}$ alkylene,
C$_{0-2}$ alkylene-NH—CO—,
C$_{0-5}$ alkylene-O—C$_{0-1}$ alkylene and
—NH—C$_{2-4}$ alkylene;
R$^6$ and R$^7$ are each independently selected from the group consisting of
hydrogen,
—NHCbz,
—NHSO$_2$Ph,
—NHC(O)—Ph, and
—N(CH3)—SO$_2$Ph.

Exemplifying the subgroup is the method wherein the compound is selected from the group consisting of:
4-(2-Guanidinoethyloxy)benzoyl-2(S)-benzyloxycarbonylamino-β-alanine,
4-(2-Guanidinoethyloxy)benzoyl-2(S)-phenylsulfonylamino-β-alanine,
2(S)-Phenylsulfonylamino-3-[4-(4-Guanidinobutyloxy)phenyl]-propionic acid,
2(S)-(N-Benzyloxycarbonylamino)-3-[4-(5-guanidopentyloxy)phenyl]-propionic acid,
4-(3-Guanidinopropyloxy)benzoyl-2-(S)-phenylsulfonylamino-β-alanine,
4-(3-Formamidinopropyloxy)benzoyl-2-(S)-phenylsulfonylamino-β-alanine,
3-Methoxy-4-(3-Guanidinopropyloxy)benzoyl-2(S)-phenylsulfonylamino-β-alanine,
3-Methoxy-4-(3-aminopropyloxy)benzoyl-2(S)-phenylsulfonylamino-β-alanine,
3-(3-Guanidinopropyloxy)benzoyl-2(S)-phenylsulfonylamino-β-alanine,
4-[2-(N-Phenylguanidino)ethyloxy]benzoyl-2(S)-phenylsulfonylamino-β-alanine,
4-[2-(N,N-Dimethylguanidino)ethyloxy]benzoyl-2(S)-phenylsulfonylamino-β-alanine,
4-(Guanidinophen-3-yloxy)benzoyl-2(S)-phenylsulfonylamino-β-alanine,
4-[2-(Guanidino)ethyloxymethyl]benzoyl-2(S)-phenylsulfonylamino-β-alanine,
3-[2-(Guanidino)ethylaminocarbonyl]benzoyl-2(S)-phenylsulfonylamino-β-alanine,
4-[2-(1-Benzylimidazol-4-yl)ethyloxy]benzoyl-2(S)-phenylsulfonylamino-β-alanine,
4-[2-(Imidazol-4-yl)ethyloxy]benzoyl-2(S)-phenylsulfonylamino-β-alanine,
4-[2-(2-Aminothiazol-4-yl)ethyloxy]benzoyl-2(S)-phenylsulfonylamino-β-alanine t-butyl ester,
4-[2-(2-Aminothiazol-4-yl)ethyloxy]benzoyl-2(S)-phenylsulfonylamino-β-alanine,
4-[2-(N-(2-Imidazolin-2-yl)aminoethyloxy]benzoyl-2(S)-phenylsulfonylamino-β-alanine,
2(S)-Phenylsulfonylamino-3-[4-(4-(N-imidazolin-2-yl)aminobutyloxy)-phenyl]propionic acid,
4-[2-[N-[Cis-3a,4,5,6,7,7a-Hexahydro-1H-benzimidazol-2-yl]amino]-ethyloxybenzoyl-2(S)-phenylsulfonylamino-β-alanine,
4-[2-(Pyrimidin-2-ylamino)ethyloxy]benzoyl-2(S)-phenylsulfonylamino-β-alanine,
4-[2-(3,4,5,6-Tetrahydropyrimidin-2-ylamino)ethyloxy]benzoyl-2(S)-phenylsulfonylamino-β-alanine,
4-[2-(2-Aminothiazol-4-yl)ethyl]benzoyl-2(S)-phenylsulfonylamino-β-alanine t-butyl ester,
4-[2-(2-Aminothiazol-4-yl)ethyl]benzoyl-2(S)-phenylsulfonylamino-β-alanine,
4-[2(S)-(N-(2-Imidazolin-2-yl)amino)propyloxy]benzoyl-2(S)-phenylsulfonylamino-β-alanine,
4-[2-(Imidazol-2-yl)ethyl]benzoyl-2(S)-phenylsulfonylamino-β-alanine,
4-[2-(Thiazol-2-ylamino)ethyloxy]benzoyl-2(S)-phenylsulfonylamino-β-alanine,
4-[2-(Pyrimidin-2-ylamino)ethyloxy]benzoyl-2(S)-benzyloxycarbonyl-amino-β-alanine,
4-[2-(3,4,5,6-Tetrahydropyrimidin-2-ylamino)ethyloxy]benzoyl-2(S)-benzyloxycarbonylamino-β-alanine,
Methyl 2(S)-benzoylamino-3-[4-(4-pyrimidin-2-ylaminobutyloxy)-phenyl]propionate,
2(S)-Benzoylamino-3-[4-(4-pyrimidin-2-ylamino)butyloxy)phenyl]-propionic acid,
2(S)-Benzoylamino-3-[4-(4-(3,4,5,-6-tetrahydropyrimidin-2-ylamino)-butyloxy)phenyl]propionic acid,
4-[2-(Pyrimidin-2-ylamino)ethyloxy]benzoyl-2(S)-N-methyl-N-phenylsulfonylamino-β-alanine t-butyl ester,
4-[2-(Pyrimidin-2-ylamino)ethyloxy]benzoyl-2(S)-N-methyl-N-phenylsulfonylamino-β-alanine,
4-[2-(3,4,5,6-Tetrahydropyrimidin-2-ylamino)ethyloxy]benzoyl-2(S)-N-methyl-N-phenylsulfonylamino-β-alanine,
4-[2-(N-(5,6-Dihydro-4-keto-1 (H)-pyrimidin-2-yl)amino)ethyloxy]-benzoyl-2(S)-phenylsulfonylamino-β-alanine,
4-(2-Aminopyridin-6-ylethynyl)benzoyl-2(S)-phenylsulfonylamino-β-alanine t-butyl ester,
4-(2-Aminopyridin-6-ylethynyl)benzoyl-2(S)-phenylsulfonylamino-β-alanine,
4-[2-(2-Aminopyridin-6-yl)ethyl]benzoyl-2(S)-phenylsulfonylamino-β-alanine,
4-[2-(2-Aminopyridin-6-yl)ethyloxy]benzoyl-2(S)-phenylsulfonylamino-β-alanine t-butyl ester,
4-[2-(2-Aminopyridin-6-yl)ethyloxy]benzoyl-2(S)-phenylsulfonylamino -β-alanine, 4-[2-(Indol-2-yl)ethyloxy]benzoyl-2(S)-phenylsulfonylamino-β-alanine methyl ester, and 4-[2-(Indol-2-yl)ethyloxy]benzoyl-2(S)-phenylsulfonylamino-β-alanine.

In another embodiment of the method of the invention, X of the compound is

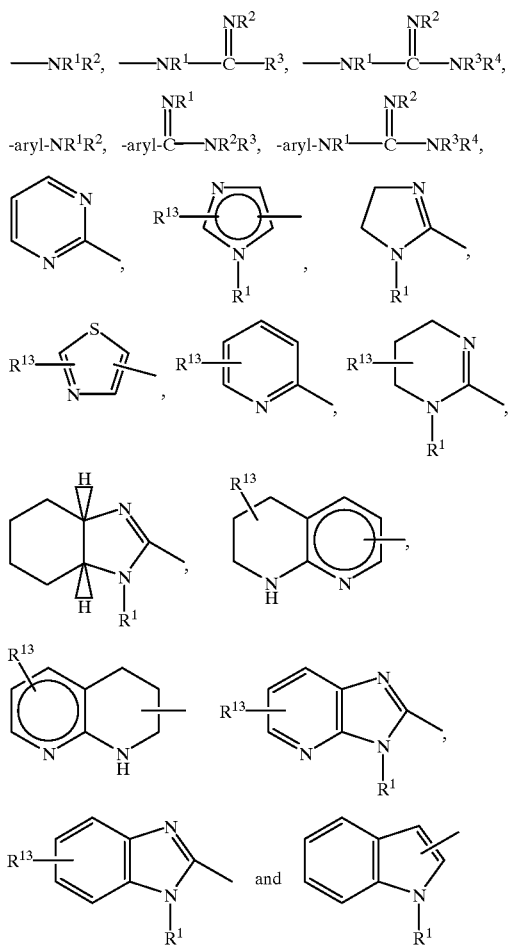

Y is selected from the group consisting of
$C_{0-8}$ alkylene,
$C_{0-8}$ alkylene-$NR^3$—CO—$C_{0-8}$ alkylene,
$C_{0-8}$ alkylene-O—$C_{0-8}$ alkylene and
$C_{0-8}$ alkylene-$NR^1$—$C_{0-8}$ alkylene;

Z and A are each independently selected from the group consisting of

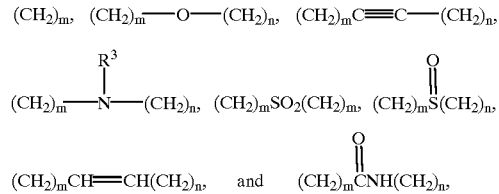

wherein m and n are independently chosen from 0–6;

B is

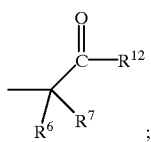

$R^1$, $R^2$, $R^3$ and $R^4$ are each independently selected from the group consisting of
hydrogen,
$C_{1-4}$ alkoxy $C_{0-6}$ alkyl,
$C_{1-4}$ alkoxycarbonyl $C_{0-6}$ alkyl,
$C_{1-6}$ alkylamino $C_{0-8}$ alkyl,
$C_{1-6}$ dialkylamino $C_{0-8}$ alkyl,
amino $C_{0-8}$ alkyl and
aryl $C_{0-8}$ alkyl;

$R^6$ and $R^7$ are each independently selected from the group consisting of:
hydrogen,
$C_{0-6}$ alkylamino $C_{0-6}$ alkyl,
$C_{0-6}$ dialkylamino $C_{0-6}$ alkyl,
aryl $C_{0-6}$ alkyloxycarbonylamino $C_{0-6}$ alkyl,
aryl $C_{0-6}$ alkylsulfonylamino $C_{0-6}$ alkyl and
aryl $C_{0-6}$ alkylcarbonylamino $C_{0-6}$ alkyl;

$R^{12}$ is selected from the group consisting of
hydroxy and
$C_{1-8}$ alkyloxy; and $R^{13}$ is selected from the group consisting of
hydrogen,
$C_{1-4}$ alkoxy $C_{0-6}$ alkyl,
$C_{1-4}$ alkoxycarbonyl $C_{0-6}$ alkyl,
$C_{1-6}$ alkylamino $C_{0-8}$ alkyl,
$C_{1-6}$ dialkylamino $C_{0-8}$ alkyl,
amino $C_{0-8}$ alkyl,
oxo and
aryl $C_{0-8}$ alkyl.

In a class of this embodiment, X of the compound is selected from

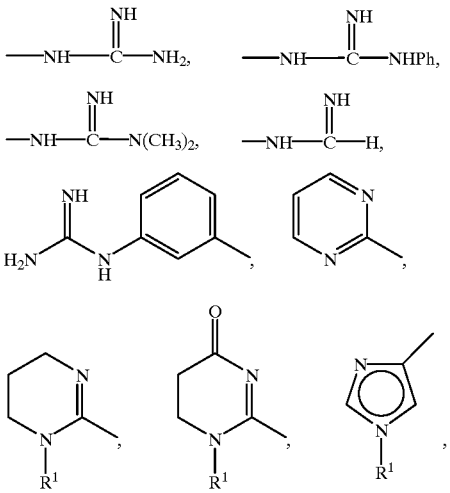

-continued

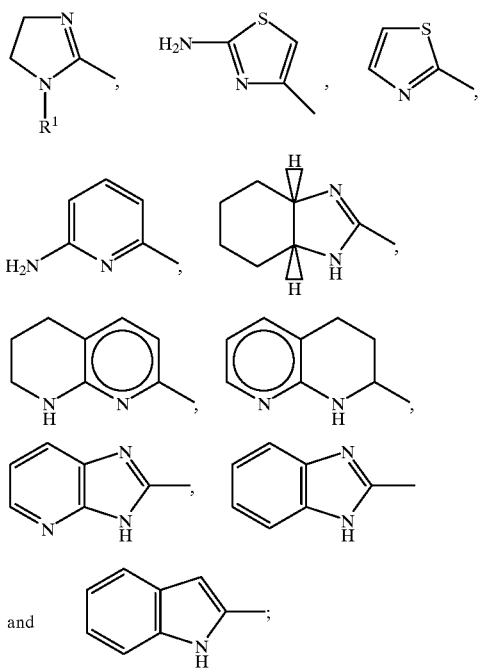

and

A and B are defined as above;
Y is selected from the group consisting of
  $C_{0-2}$ alkylene,
  $C_{0-2}$ alkylene-NH-CO—,
  $C_{0-5}$ alkylene-O-$C_{0-1}$ alkylene and
  —NH—$C_{2-4}$ alkylene;
$R^6$ and $R^7$ are each independently selected from the group consisting of
  hydrogen,
  —NHCbz,
  —NHSO$_2$Ph,
  —NHC(O)—Ph, and
  —N(CH3)—SO$_2$Ph.

Exemplifying the class is a method wherein the compound is selected from the group consisting of
4-[2-(1H-Imidazo[4,5-6]pyridin-2-yl)ethenyl]benzoyl-2(S)-phenylsulfonylamino-β-alanine t-butyl ester,
4-[2-(1H-Imidazo [4,5-b]pyridin-2-yl)ethenyl]benzoyl-2(S)-phenylsulfonylamino-β-alanine,
4-[2-(1H-Imidazo[4,5-b]pyridin-2-yl)ethyl]benzoyl-2(S)-phenylsulfonylamino-β-alanine,
4-[2-( 1,8-Naphthyidin-7-yl)ethenyl)benzoyl-2(S)-phenylsulfonylamino-β-alanine t-butylester,
4-[2-(1,2,3,4-Tetrahydro-1,8-naphthyridin-7-yl)ethyl]benzoyl-2(S)-phenylsulfonylamino-β-alanine t-butyl ester,
4-[2-(1,2,3,4-Tetrahydro-1,8-naphthyridin-7yl)ethyl]benzoyl-2(S)-phenylsulfonylamino-β-alanine,
4-[2-(1,8-Naphthyridin-7-yl)ethenyl]benzoyl-2(S)-phenylsulfonylamino-β-alanine ethyl ester,
4-[2-(1,2,3,4-Tetrahydro-1,8-naphthyridin-7-yl)ethyl]benzoyl-2(S)-phenylsulfonylamino-β-alanine ethyl ester,
4-[2-(1,2,3,4-Tetrahydro-1,8 naphthyridin-7-yl)ethyl]benzoyl-2(S)-[1(S)10-camphorsulfonylamido]β-alanine ethyl ester,
4-[2-(1,2,3,4-Tetrahydro-1,8 naphthyridin-7-yl)ethyl]benzoyl-2(S)-[1(S)10-camphorsulfonylamido]β-alanine,
4-[(3-Aminoisoquinolin-1-yl)ethynyl]benzoyl-2(S)-phenylsulfonamido-β-alanine ethyl ester,
4-[(3-Aminoisoquinolin-1-yl)ethynyl]benzoyl-2(S)-phenylsulfonamido-β-alanine trifluoroacetate,
4-[2-(3-Aminoisoquinolin-1-yl)ethyl]benzoyl-2(S)-phenylsulfonamido-β-alanine trifluoroacetate,
4-[3-[N-(1H-Benzimidazo-2-yl)amino]propoxy]benzoyl-2(S)-phenylsulfonylamino-β-alanine t-butyl ester, and
4-[3-[N-(1H-Benzimidazol-2-yl)amino]propoxy]benzoyl-2 1(S)-phenylsulfonylamino-β-alanine.

DETAILED DESCRIPTION OF THE INVENTION

Compounds of the invention are useful for treating mammals suffering from a bone condition caused or mediated by increased bone resorption, who are in need of such therapy. Pharmacologically effective amounts of the compounds, including pharamaceutically acceptable salts thereof, are administered to the mammal, to inhibit the activity of mammalian osteoclasts.

Compounds of the invention are also useful for inhibiting tumor growth in mammals. Pharmacologically effective amounts of the compounds, including pharamaceutically acceptable salts thereof, are administered to the mammal, to inhibit tumor growth. The growth of tumors depends on an adequate blood supply, which in turn depends on growth of new vessels into the tumor. New vessels are stimulated by factors secreted by the tumor. Inhibition of angiogenesis can cause tumor regression in animals.

Compounds of the invention are also useful for treating and preventing diabetic retinopathy in mammals. Pharmacologically effective amounts of the compounds, including pharamaceutically acceptable salts thereof, are administered to the mammal, to inhibit diabetic retinopathy.

Compounds are also useful in the prevention of restenosis of vessels.

The term "pharmaceutically acceptable salts" means non-toxic salts of the compounds of this invention which are generally prepared by reacting the free base with a suitable organic or inorganic acid. Representative salts include the following salts: Acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, glucoheptanate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, pantothenate, phosphate/diphosphate, polygalactouronate, salicylate, stearate, subacetate, succinate, tannate, tartrate, teoclate, tosylate, triethiodide, valerate. The term also includes acid salts of the compounds, e.g., sodium salts, potassium salts, magnesium salts, etc.

The term "pharmaceutically effective amount" means that amount of a drug or pharmaceutical agent that will elicit the biological or medical response that is being sought by a researcher or clinician.

The term "aryl" means a mono- or polycyclic system composed of 5- and/or 6-membered aromatic rings containing 0, 1, 2, 3, or 4 heteroatoms chosen from N, O or S and either unsubstituted or substituted. "aryl" with a lower case "a" is defined herein to be broader than the term "Aryl" with a capital "A". One skilled in the art can readily distinguish between the two terms which are clearly defined herein.

The term "bone resorption activity" means the process by which osteoclasts solubilize bone minerals and increase the activity of enzymes that degrade bone matrix.

The term "alkyl" means straight, branched, or cyclic alkane, alkene or alkyne.

The term "alkylene" shall include both straight and branched chain alkylenes (e.g., —$CH_2$—, —$CH(CH_3)$—, —$CH(CH_3)$—$CH_2$—, etc.).

The term "alkoxy" includes an alkyl portion where alkyl is as defined above.

The terms "arylalkyl" and "alkylaryl" include an alkyl portion where alkyl is as defined above and an aryl portion where aryl is as defined above. The $C_{0-n}$ or $C_{1-n}$ designation where n may be an integer from 1–10 or 2–10 respectively, refers to the alkyl component of the arylalkyl or alkylaryl unit.

The term "halogen" includes fluorine, chlorine, iodine and bromine. The term "oxy" means an oxygen (O) atom. The term "oxo" refers to a bivalent oxygen atom (=O). The term "thio" shall mean a sulfur (S) atom. In the schemes and examples below, various reagent symbols have the following meanings:

The term "L- or D-amino acids" means naturally occurring L- or D-amino acids, for example, those naturally occurring L-amino acids present in humans, e.g. protein amino acids,, including L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine, and those naturally occurring D-amino acids which are non-protein amino acids, such as those found, for example, in antibiotic substances produced by bacteria and fingi, including D-valine, D-asparagine, D-glutamate, D-ornithine, D-phenylalanine, D-leucine, D-cysteine, and D-aspartate. (see Zubay "BIOCHEMISTRY" Addison-Wesley Publishing Company, Inc. (Reading, Mass.) 1983 pp. 867–870 and Stryer "BIOCHEMISTRY" W. H. Freeman and Company (New York, N.Y.) 3rd Edition 1988 pp. 16–21).

BOC(Boc): t-butyloxycarbonyl.
Pd/C: Palladium on activated carbon catalyst.
DMF: Dimethylformamide.
DMSO: Dimethylsulfoxide.
CBZ(Cbz): Carbobenzyloxy or benzyloxycarbonyl.
$CH_2Cl_2$: Methylene chloride.
$CHCl_3$: Chloroform.
EtOH: Ethanol.
NMM: N-methylmorpholine
CDI: Carbonyldiimidazole
HOBT: 1-Hydroxybenzotriazole
MeOH: Methanol.
EtOAc: Ethyl acetate.
HOAc: Acetic acid.
BOP: Benzotriazol-1-yloxytris(dimethylamino)-phosphonium hexafluorophosphate.
DPFN: 3,5-Dimethyl-1-pyrazolylformamidine nitrate
$BH_3.DMS$ Borane-dimethylsulfide
EDC: 1-(3-Dimethylaminopropyl)-3-ethylcarbodiimide hydrochloride
LDA: Lithium diisopropylamide
DME: 1,2-Dimethoxyethane
DEAD: Diethyl azodicarboxylate
Dibal: Diisobutylaluminum hydride
THF: Tetrahydrofuran
TEA: Triethylamine
TFA: Trifluoroacetic acid
DIPEA: Diisopropylethylamine
DIAD: Diisopropyl azodicarboxylate
PCA.HCl: Pyrazole carboxamidine hydrochloride The compounds of the present invention can be administered in such oral dosage forms as tablets, capsules (each of which includes sustained release or timed release formulations), pills, powders, granules, elixers, tinctures, suspensions, syrups and emulsions. Likewise, they may also be administered in intravenous (bolus or infusion), intraperitoneal, subcutaneous or intramuscular form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration, the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day and preferably 1.0–100 mg/kg/day and most preferably 1.0 to 20 mg/kg/day. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta- lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The novel compounds of the present invention were prepared according to the procedure of the following schemes and examples, using appropriate materials and are further exemplified by the following specific examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

SCHEME 1

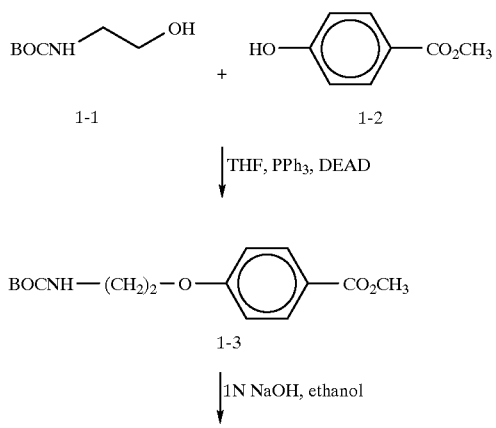

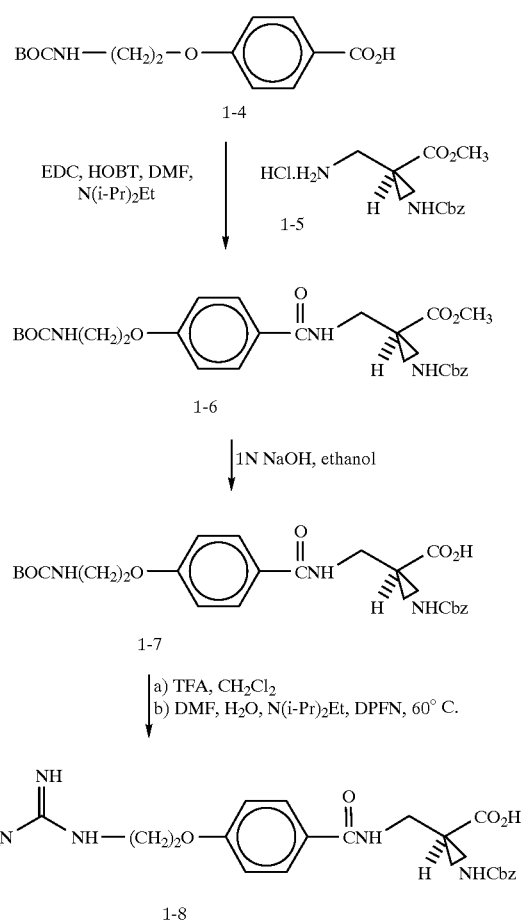

Methyl 4-(2-N-BOC-Aminoethyloxy)benzoate (1-3)

To a stirred solution of 1-2 (1.6 g, 10.5 mmol; Aldrich), PPh$_3$ (3.4 g, 13.1 mmol), and THF (38 mL) at ambient temperature, was added 1-1 (1.7 g, 10.5 mmol) and DEAD (5.1 mL, 11.0 mmol; 40% toluene solution) in THF (15 mL) dropwise over a 15 min period. After stirring for 20 h the reaction mixture was diluted with EtOAc and then washed with sat. NaHCO$_3$, 10% KHSO$_4$ and brine, dried (MgSO$_4$) and concentrated. Flash chromatography (silica, 20% EtOAc/hexanes) gave 1-3 as a colorless oil. R$_f$ 0.84 (silica, 30% EtOAc/hexanes).

$^1$H NMR (300 MHz, CDCl$_3$) δ 8.02 (d, 2H), 6.93 (d, 2H), 5.02 (m, 1H), 4.11 (m, 2H), 3.89 (s, 3H), 3.58 (m, 2H), 1.46 (s, 9H).

4-[2-(N-BOC-Amino)ethyloxy]benzoic acid (1-4)

A mixture of 1-3 (1.3 g, 4.4 mmol), 1N NaOH (26.7 mL, 26.7 mmol) and ethanol (33 mL) was stirred at ambient temperature for 20 h. The reaction mixture was concentrated and the residue dissolved in H$_2$O (15 mL) and then washed with ether. The aqueous portion was acidified with 10% KHSO$_4$ and then extracted with EtOAc. The organic phase was washed with brine, dried (MgSO$_4$) and concentrated to give 1-4 as a white solid. R$_f$ 0.26 (silica, 9:1:1 CH$_2$Cl$_2$/CH$_3$OH/AcOH).

¹H NMR (300 MHz, CDCl₃) δ 8.08 (d, J=9 Hz, 2H), 6.96 (d, J=9 Hz, 2H), 5.02 (m, 1H), 4.12 (m, 2H), 3.60 (m, 2H), 1.48 (s, 9H).

4-[2-(N-BOC-Amino)ethyloxy]benzoyl-2(S)-benzyloxycarbonylamino-β-alanine methyl ester (1-6)

To a stirred solution of 1-4 (1.1 g, 4.1 mmol), 1-5 (0.97 g, 4.1 mmol) HOBT (0.55 g, 4.1 mmol), N(i-Pr)₂Et (2.2 mL, 12.3 mmol), and DMF (45 mL) at −15° C. was added EDC (0.81 g, 4.1 mmol) followed by removal of the cooling bath. After 72 h the reaction mixture was diluted with EtOAc and then washed with H₂O, sat. NaHCO₃, 10% KHSO₄ and brine, dried (MgSO₄) and concentrated. Flash chromatography (silica, 70% EtOAc/hexanes) gave 1-6 as a white powder. R$_f$ 0.64 (silica, EtOAc).

¹H NMR (300 MHz, CDCl₃) δ 7.72 (d, J=9 Hz, 2H), 7.34 (m, 5H), 6.91 (d, J=9 Hz, 2H), 6.80 (m, 1H), 5.95 (m, 1H), 5.13 (m, 2H), 4.99 (m, 1H), 4.55 (m, 1H), 4.08 (m, 2H), 3.85 (m, 2H), 3.80 (s, 3H), 3.56 (m, 2H), 1.47 (s, 9H).

4-[2-(N-BOC-Anino)ethyloxy]benzoyl-2(S)-benzyloxycarbonylamino-β-alanine (1-7)

Utilizing the procedure for converting 1-3 to 1-4,1-6 (300 mg, 0.64 mmol) gave 1-7 as a colorless oil. R$_f$ 0.59 (silica, 9:1:1 CH₂Cl₂/CH₃OH/AcOH).

¹H NMR (300 MHz, CDCl₃) δ 7.70 (d, 2H), 7.30 (m, 5H), 6.80 (d, 2H), 6.52 (m, 1H), 5.12 (m, 1H), 5.06 (m, 2H), 4.39 (m, 1H), 4.00–3.50 (m, 6H), 1.46 (s, 9H).

4-[2-(Guanido)ethyloxy]benzoyl-2(S)-benzyloxycarbonylamino-β-alanine (1-8)

A solution of 1-7 (210 mg, 0.46 mmol), CH₂Cl₂ (3 mL) and TFA (3 mL) was stirred at ambient temperature for 30 min followed by concentration. Most of the excess TFA was then removed azeotropically with toluene. The resulting oil was dissolved in DMF/H₂O (4 mL; 3:1), treated with DIPEA (0.36 mL, 2.5 mmol) and DPFN (0.12 g, 0.65 mmol) and then heated at 60° C. for 2 h. The cooled reaction mixture was concentrated and the residual H₂O removed with an ethanol azeotrope. Flash chromatography (silica, 10:0.8:0.8 ethanol/NH₄OH/H₂O) gave 1-8 as a white powder. R$_f$ 0.25 (silica, 10:1:1 ethanol/NH₄OH/H₂O).

¹H NMR (400 MHz, CD₃OD) δ 7.53 (d, J=9 Hz, 2H), 7.06 (m, 5H), 6.74 (d, J=9 Hz, 2H), 4.81 (m, 2H), 4.03 (m, 1H), 3.94 (t, J=5 Hz, 2H), 3.48 (m, 2H), 3.36 (t, J=5 Hz, 2H).

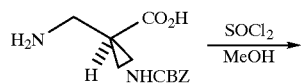

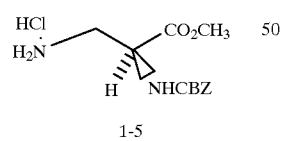

Methyl 3-Amino-2(S)-benzyloxycarbonylaminopropionate hydrochloride (1-5)

3-Amino-2(S)-benzyloxycarbonylaminopropionic acid (Fluka) (5.0 g, 21.0 mmoles) was suspended in MeOH and at −10° SOCl₂ (23.0 mmoles) was added. The reaction mixture was allowed to gradually warm to room temperature over 16 h. The solvent was then removed and the resulting solid was triturated with Et₂O to give 1-5.

¹H NMR (300 MHz, D₂O) δ 3.32 (2H, m), 3.52 (2H, m), 3.70 (1H,m), 3.80 (4H, m), 4.59 (1H, m), 5,18 (3H, s), 7.45 (5H, s).

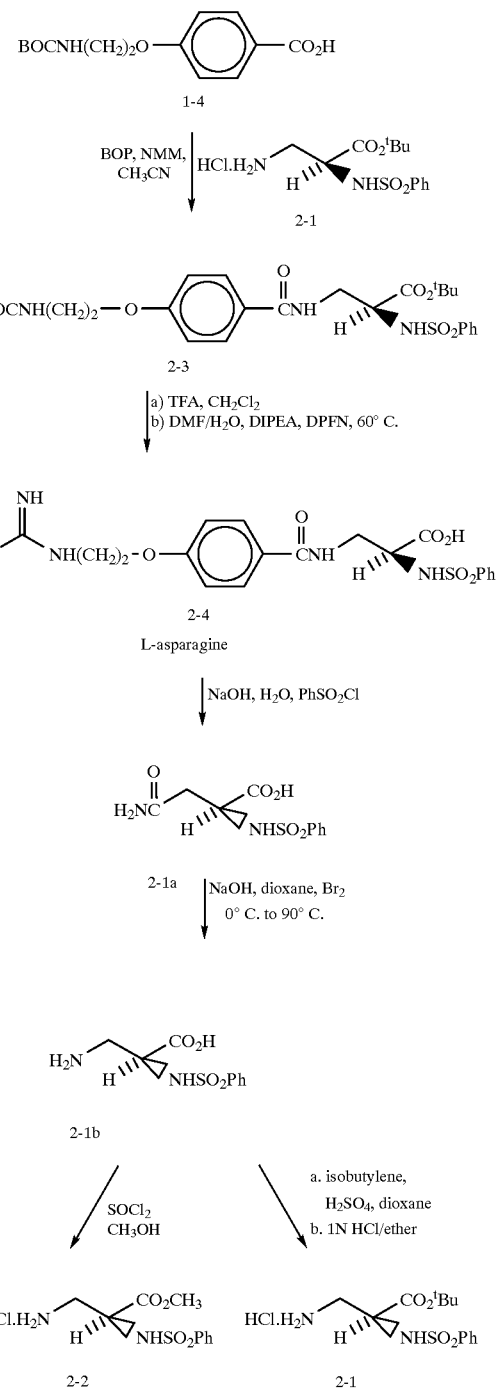

SCHEME 2 tert-Butyl 3-amino-2(S)-phenylsulfonylaminopropionate hydrochloride (2-1)

In a Fischer-Porter tube, a mixture of 2-1b (10.2 g, 42 mmol) and DME (150 mL) was sequentially treated with H₂SO₄ (6.4 mL, 0.12 mol), cooled to −78° C., and then condensed isobutylene (75 mL). The cooling bath was removed. After 24 h, ice/water (250 mL) was added followed by washing with ether (2×). The aqueous phase was basified with aq 6N NaOH, then saturated with NaCl, followed by extraction with EtOAc (3×). The combined extracts were washed with brine, dried (MgSO₄), and concentrated to give a white solid. This was dissolved in CH₂Cl₂ and treated with 1N HCl/ether (22 mL), and then concentrated to give 2-1 as a glassy yellow solid.

¹H NMR (400 MHz, DMSO) δ 8.25–8.00 (m, 4H), 7.85–7.58 (m, 5H), 4.08 (m, 1H), 3.10 (m, 1H), 2.73 (m, 1H), 1.17 (s, 9H). 4-[2-(N-BOC-Amino)ethyloxy]benzoyl-2(S)-phenylsulfonylamino-β-alanine tert-butyl ester (2-3)

To a stirred solution of 1-4 (200 mg, 0.71 mmol), 2-1 (260 mg, 0.85 mmol), NMM (313 μL, 2.8 mmol), and CH₃CN (4 mL) at ambient temperature was added BOP reagent (473 mg, 1.1 mmol). After 20 h the reaction mixture was diluted with EtOAc and then washed with H₂O, sat. NaHCO₃, 10% KHSO₄ and brine, dried (MgSO₄) and concentrated. Flash chromatography (silica, 40% EtOAc/hexanes) gave 2-3 as a white solid. R_f 0.19 (silica, 40% EtOAc/hexanes).

¹H NMR (300 MHz, CD₃OD) δ 7.77 (m, 2H), 7.67 (d, J=9 Hz, 2H), 7.42 (m, 3H), 6.92 (d, J=9 Hz, 2H), 4.02 (m, 3H), 3.59 (dd, 1H), 3.42 (dd, 1H), 3.38 (m, 2H), 1.38 (s, 9H), 1.16 (s, 9H).

4-[2-(Guanidino)ethyloxy]benzoyl-2(S)-phenylsulfonylamino-β-alanine (2-4)

A solution of 2-3 (340 mg, 0.64 mmol), TFA (3 mL), and CH₂Cl₂ (3 mL) was stirred at ambient temperature for 1.0 h. Concentration, followed by azeotropic removal of the residual TFA, with toluene, gave an oil which was dissolved in DMF/H₂O (3 mL; 3:1) and then treated with N(i-Pr)₂Et (334 μL, 1.9 mmol) and DPFN (193 mg, 0.95 mmol). This solution was heated at 60° C. for 4 h and the cooled reaction mixture concentrated. Flash chromatography (silica, 10/0.2/0.2 to 10/1/1 ethanol/NH₄OH/H₂O) gave 2-4 as a white powder. R_f 0.20 (silica, 10/1/1 ethanol/NH₄OH/H₂O).

¹H NMR (400 MHz, D₂O) δ 7.62 (m, 2H), 7.43 (d, J=9 Hz, 2H), 7.18 (m, 3H), 6.93 (d, J=9 Hz, 2H), 4.18 (m, 2H), 3.72 (m, 1H), 3.55 (m, 3H), 3.19 (m, 1H).

N-Phenylsulfonyl-L-asparagine (2-1a)

To a stirred solution of L-asparagine (Aldrich) (10 g, 76 mmol), NaOH (3.4 g, 85 mmol), H₂O (50 mL), and dioxane (50 mL) at 0° C. was added PhSO₂Cl (10.6 mL, 84 mmol). After 1 min, NaOH (3.4 g) in H₂O (50 mL) was added and the reaction mixture stirred for 30 MIN. The reaction mixture was then concentrated to remove dioxane then washed with EtOAc. The aqueous phase was then cooled to 0° C. and acidified to pH 5.0 with conc. HCl to effect product precipitation. The resulting solid was collected by filtration, washed with H₂O (20 mL) and dried at 50° C. under vacuum to give N-phenylsulfonyl-L-asparagine (2-1a) as a white solid.

R_f 0.40 (silica, 10:1:1 ethanol/H₂O/NH₄OH). ¹H NMR (300 MHz, D₂O) δ 7.59 (m, 2H), 7.26 (m, 3H), 3.92 (m, 1H), 3.02 (m, 1H), 2.35 (m, 1H).

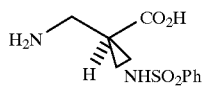

3-Amino-2(S)-phenylsulfonylaminopropionic acid (2-1b)

To stirred solution of NaOH (15.6 g, 0.4 mol) in H₂O (70 mL), cooled with an icebath, was added bromine (3.6 mL, 0.07 mol) dropwise. After 5 min, a cold solution of N-phenylsulfonyl-L-asparagine 2-1a (14.6 g, 54 mmol) and NaOH (4.3 g, 0.1 mol) in H₂O (50 mL) was added in one portion. The solution was stirred for 20 min at 0° C. then 30 min at 90° C. The reaction mixture was recooled to 0° C., and the pH adjusted to 7 through dropwise addition of conc. HCl. The white precipitate formed was collected by filtration and then dried to give (2-1b) as a white solid. ¹H NMR (300 MHz, D₂O) δ 8.00–7.50 (m, 5H), 3.88 (m, 1H), 3.37 (m, 1H), 3.12 (m, 1H).

Methyl 3-Amino-2(S)-phenylsulfonylaminopropionate hydrochloride (2-2)

To a stirred solution of 2-1b (5.0 g, 21 mmol) in CH₃OH (100 mL) at 0° C. was added SOCl₂ (7.5 mL, 100 mmol) dropwise. The cooling bath was then removed and the solution stirred at ambient temperature for 20 h. Concentration and trituration with ether gave 2-2 as a white solid.

¹H NMR (300 MHz, D₂O) δ 7.82–7.50 (m, 5H), 4.32 (m, 1H), 3.40 (m, 1H), 3.32 (s, 3H), 3.10 (m, 1H).

tert-Butyl 3-amino-2(S)-phenylsulfonylaminopropionate hydrochloride (2-1)

In a Fischer-Porter tube, a mixture of 2-1b (10.2 g, 42 mmol) and DME (150 mL) was sequentially treated with H₂SO₄ (6.4 mL, 0.12 mol), cooled to −78° C., and then condensed isobutylene (75 mL). The tube was sealed and the cooling bath was removed. After 24 h, ice/water (250 mL) was added followed by washing with ether (2×). The aqueous phase was basified with aq 6N NaOH, then saturated with NaCl, followed by extraction with EtOAc (3×). The combined extracts were washed with brine, dried (MgSO₄), and concentrated to give a white solid. This was dissolved in CH₂Cl₂ and treated with 1N HCl/ether (22 mL), and then concentrated to give 2-1 as a glassy yellow solid.

¹H NMR (400 MHz, DMSO) δ 8.25–8.00 (m, 4H), 7.85-7.58 (m, 5H), 4.08 (m, 1H), 3.10 (m, 1H), 2.73 (m, 1H), 1.17 (s, 9H).

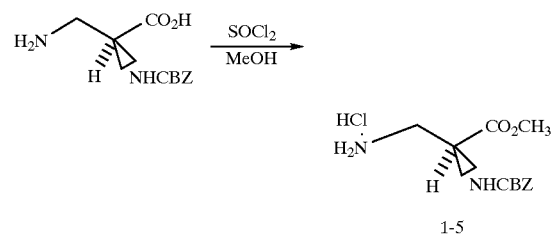

Methyl 3-amino-2(S)-benzyloxycarbonylaminopropionate hydrochloride (1-5)

3-Amino-2(S)-benzyloxycarbonylaminopropionic acid (Fluka) (5.0 g, 21.0 mmoles) was suspended in MeOH and at −10° C. SOCl₂ (1.7 mL, 23.0 mmoles) was added. The reaction mixture was allowed to gradually warm to room temperature over 16 h. The solvent was then removed and the resulting solid was triturated with Et₂O to give 1-5.

¹H NMR (300 MHz, D₂O) δ 7.45 (s, 5H), 5.18 (s, 3H), 4.59 (m, 1H), 3.80 (m, 4H), 3.70 (m, 1H), 3.52 (m, 2H), 3.32 (m, 2H).

SCHEME 3

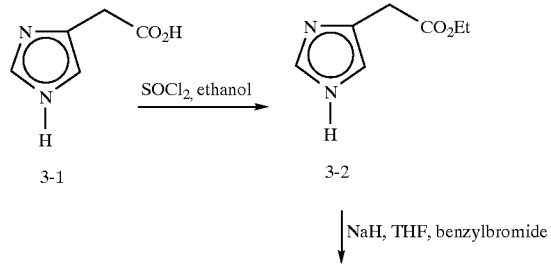

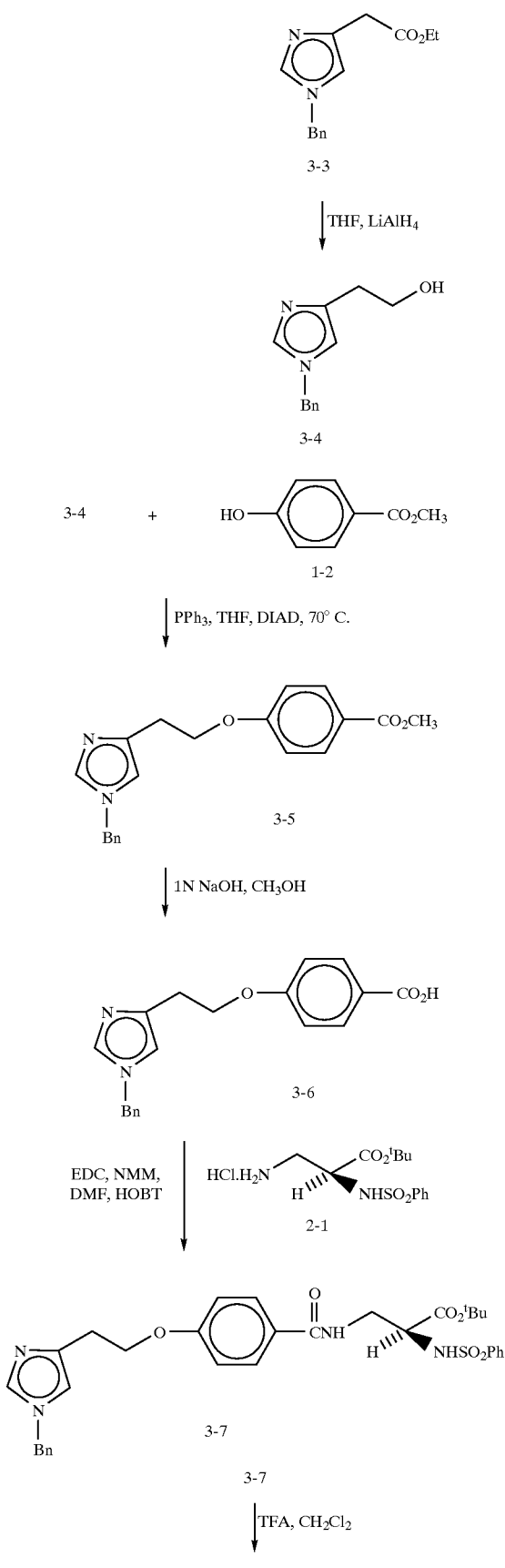

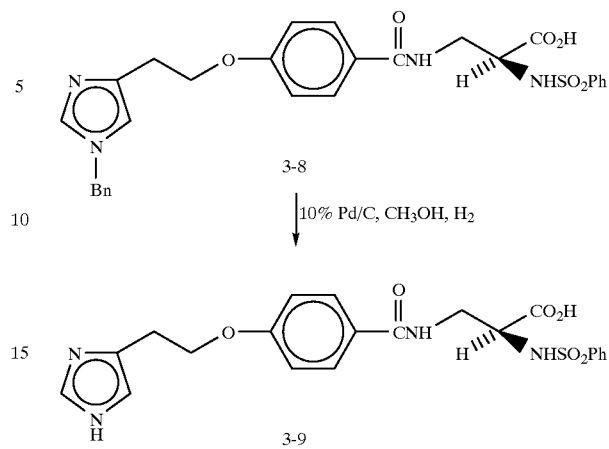

Ethyl imidazol-4-ylacetate (3-2)

To a suspension of 3-1 (5.0 g, 30.7 mmol, Aldrich) in ethanol (100 mL) at ambient temperature was added SOCl$_2$ (11.2 mL, 154 mmol) dropwise. After stirring overnight the homogenous solution was concentrated and the residue suspended in CH$_2$Cl$_2$ and washed with 10 sat. NaHCO$_3$. The sat. NaHCO$_3$ was back-extracted with CH$_2$Cl$_2$. The CH$_2$Cl$_2$ portions were combined, dried (MgSO$_4$), and concentrated to give 3-2 as a pale yellow liquid.

$^1$H NMR (300 MHz, CDCl$_3$) δ 7.60 (s, 1H), 6.97 (s, 1H), 4.10 (q, 2H), 3.67 (s, 2H), 1.24 (t, 3H).

Ethyl 1-Benzylimidazol-4-ylacetate (3-3)

A THF (15 mL) solution of 3-2 (3.8 g, 24.6 mmol), was added dropwise to a stirred suspension of NaH (1.1 g, 26.5 mmol) in THF (25 mL) at 0° C. over 30 min. The cooling bath was then removed and the mixture stirred at ambient temperature for 3 h followed by dropwise addition of benzyl bromide (24.6 mmol) over 30 min. After 20 h the solvent was evaporated and the residue partitioned between CH$_2$Cl$_2$ and H$_2$O. The organic phase was washed with H$_2$O, dried (MgSO$_4$), and concentrated. Flash chromatography (silica, 40% (CHCl$_3$/NH$_3$)/EtOAc) gave 3-3 as a pale yellow oil. R$_f$ 0.15 (silica, 40% (CHCl$_3$/NH$_3$)/EtOAc)).

$^1$H NMR (300 MHz, CDCl$_3$) δ 7.52 (s, 1H), 7.40–7.10 (m, 5H), 6.87 (s, 1H), 5.08 (s, 2H), 4.15 (q, 2H), 3.62 (s, 2H), 1.26 (t, 3H).

2-(1-Benzylimidazol-4-yl)ethanol (3-4)

To a stirred solution of 3-3 (4.6 g, 19 mmol) in THF (50 mL) at ambient temperature was added LiAlH$_4$ (9.4 mL, 9.4 mmol; 1M THF solution). After 1.0 h the reaction was quenched with sat. NaK tartrate solution. The mixture was poured into a EtOAc/H$_2$O mixture. The organic portion was washed with brine, dried (MgSO$_4$) and concentrated to give 3-4 as a yellow viscous oil.

$^1$H NMR (300 MHz, CDCl$_3$) δ 7.44 (s, 1H), 7.40–7.10 (m, 5H), 6.68 (s, 1H), 5.03 (s, 2H), 3.87 (t, J=6 Hz, 2H), 2.77 (t, J=6 Hz, 2H).

Methyl 4-[2-(1-Benzylimidazol-4-yl)ethyloxy]benzoate (3-5)

A solution of 1-2 (152 mg, 1.0 mmol), PPh$_3$ (341 mg, 1.3 mmol), and THF (20 mL) was treated dropwise with DIAD (256 mL, 1.3 mmol) and 3-4 (202 mg, 1.0 mmol) in THF (10 mL) over a 30 min period and then heated at 70° overnight. After 72 h, the reaction mixture was concentrated and then subjected to flash chromatography (silica, 40% (CHCl$_3$/NH$_3$)/EtOAc) to give 3-5 as a colorless oil. R$_f$ 0.16 (silica, 40% (CHCl$_3$/NH$_3$)/EtOAc).

$^1$H NMR (300 MHz, CDCl$_3$) δ 7.96 (d, J=9 Hz, 2H), 7.46 (s, 1H), 7.40–7.10 (m, 5H), 6.89 (d, J=9 Hz, 2H), 6.74 (s, 1H), 5.04 (s, 2H), 4.28 (t, J=6 Hz, 2H), 3.85 (s, 3H), 3.06 (t, J=6 Hz, 2H).

4-[2-(1-Benzylimidazol-4-yl)ethyloxy]benzoic acid (3-6)

A mixture of 3-5 (170 mg, 0.51 mmol), 1N NaOH (5 mL), and CH$_3$OH (10 mL) was stirred at ambient temperature for 20 h. The reaction mixture was cooled to 0° C., neutralized with 1N HCl (5 mL), and then concentrated. The solid was extracted with CHCl$_3$ and the combined extracts concentrated to give 3-6 as a gelatinous solid.

$^1$H NMR (300 MHz, CD$_3$OD) δ 7.90 (d, J=9 Hz, 2H), 7.67 (s, 1H), 7.40–7.20 (m, 5H), 6.95 (s, 1H), 6.88 (d, J=9 Hz, 2H), 5.16 (s, 2H), 4.22 (t, J=6 Hz, 2H), 2.99 (t, J=6 Hz, 2H).

4-[2-(1-Benzyl-imidazol-4-yl)ethyloxy]benzoyl-2(S)-phenylsulfonylamino-β-alanine tert-butyl ester (3-7)

A stirred mixture of 3-6 (147 mg, 0.46 mmol), HOBT (94 mg, 0.61 mmol), 2-1 (154 mg, 0.46 mmol), NMM (100 μL, 0.91 mmol), and DMF (1.2 mL) at 0° C. was treated with EDC (118 mg, 0.61 mmol) followed by removal of the cooling bath. The reaction pH was adjusted to 8 by addition of more NMM. After 20 h the reaction mixture was concentrated and the residue purified by to a flash chromatography column (silica, 9/0.5/0.5 CH$_2$Cl$_2$/CH$_3$OH/AcOH) to give 3-7 as a yellow solid after azeotropic removal of residual AcOH with toluene. R$_f$ 0.48 (silica, 9/0.5/0.5 CH$_2$Cl$_2$/CH$_3$OH/AcOH).

$^1$H NMR (300 MHz, CDCl$_3$) δ 7.87 (d, J=9 Hz, 2H), 7.80–7.10 (m, 11H), 6.92 (d, J=9 Hz, 2H), 6.75 (s, 1H), 6.58 (m, 1H), 5.67 (m, 1H), 5.06 (s, 2H), 4.29 (t, J=6 Hz, 2H), 3.90 (m, 2H), 3.56 (m, 1H), 3.06 (t, J=6 Hz, 2H), 1.29 (s, 9H).

4-[2-(1-Benzylimidazol-4-yl)ethyloxy]benzoyl-2(S)-phenylsulfonylamino-β-alanine (3-8)

A solution of 3-7 (252 mg, 0.42 mmol), TFA (3 mL) and CH$_2$Cl$_2$ (10 mL) was stirred at ambient temperature for 3 h, followed by concentration. Flash chromatography (silica, 9:0.5:0.5 ethanol/NH$_4$OH/H$_2$O (2×)) gave 3-8 as a viscous gum. R$_f$ 0.08 (silica, 9:0.5:0.5 ethanol/NH$_4$OH/H$_2$O).

$^1$H NMR (300 MHz, CD$_3$OD) δ 7.99 (s, 1H), 7.84 (d, 2H), 7.72 (d, 2H), 7.40–7.20 (m, 8H), 7.06 (s, 1H), 6.92 (d, J=9 Hz, 2H), 5.22 (s, 2H), 4.24 (t, J=6 Hz, 2H), 3.86 (m, 1H), 3.68 (dd, 1H), 3.53 (dd, 1H), 3.03 (t, J=6 Hz, 2H).

4-[2-(Imidazol-4-yl)ethyloxy]benzoyl-2(S)-phenylsulfonylamino-β-alanine (3-9)

A mixture of 3-8 (94 mg, 0.17 mmol), 10% Pd/C (94 mg), and 4.4% formic acid/CH$_3$OH was stirred at ambient temperature under a hydrogen atmosphere (1 atm) for 72 h. The reaction mixture was filtered through a celite pad and the filtrate concentrated. Flash chromatography (silica, 5/3/0.5 CH$_2$Cl$_2$/CH$_3$OH/32% AcOH; then 10/1/1 ethanol/NH$_4$OH/H$_2$O) gave 3-9 as a colorless solid. R$_f$ 0.33 (silica, 5/3/0.5 CH$_2$Cl$_2$/CH$_3$OH/32% AcOH).

$^1$H NMR (400 MHz, CD$_3$OD) δ 7.85 (m, 3H), 7.77 (d, J=9 Hz, 2H), 7.50 (m, 3H), 7.03 (s, 1H), 6.97 (d, J=9 Hz, 2H), 4.28 (t, J=6 Hz, 2H), 3.77 (m, 1H), 3.67 (dd, 1H), 3.54 (dd, 1H), 3.11 (t, J=6 Hz, 2H).

SCHEME 4

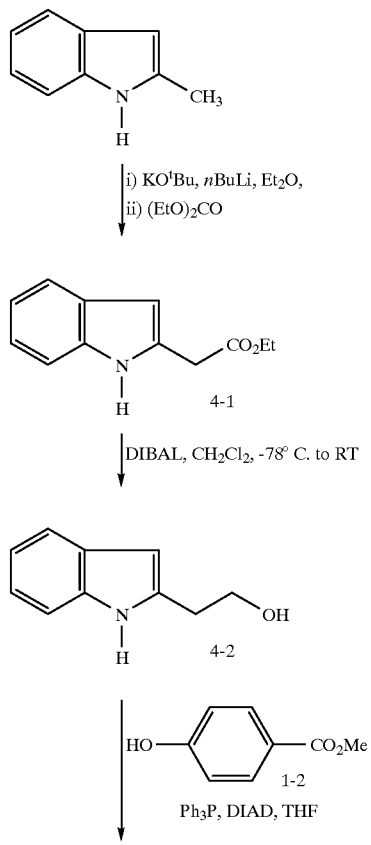

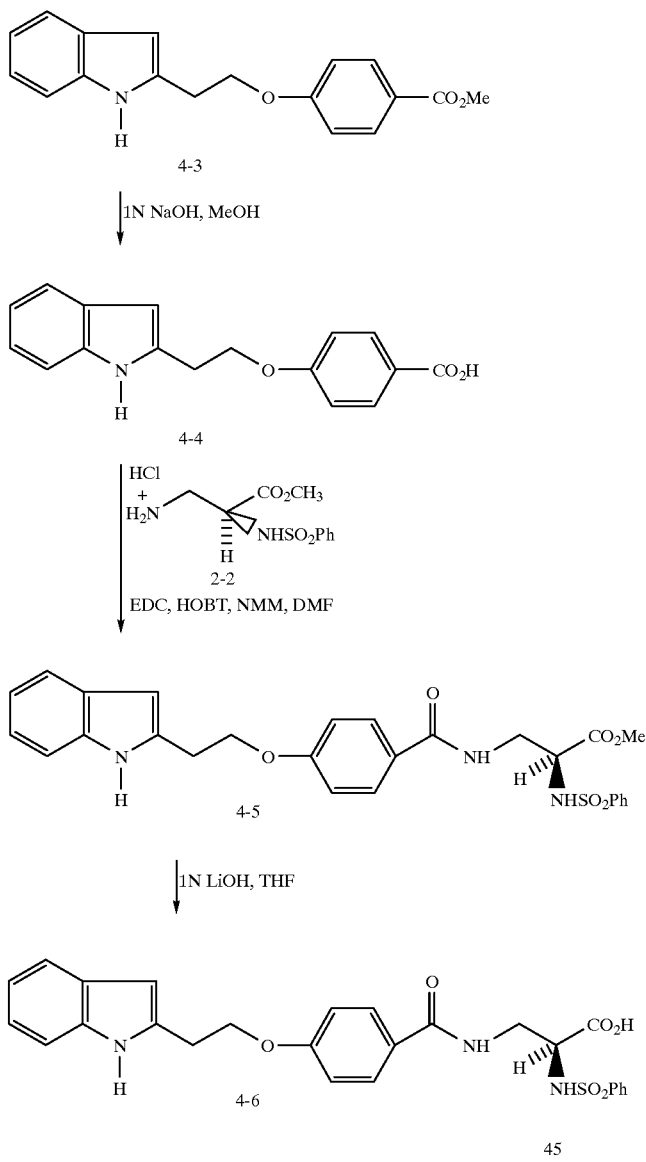

Ethyl Indol-2-ylacetate (4-1)

2-Methylindole (1.7 g, 13 mmol) in 130 mL Et$_2$O was treated with nBuLi (1.6M in hexane, 24.4 mL, 39 mmol) and KO$^t$Bu (1.0M in THF, 26 mL, 26 mmol) at RT for 40 min, then diethylcarbonate (3.15 mL, 26 mmol) was added. After 1 h the reaction was quenched with water, adjusted to pH 7 with 6N HCl, extracted with EtOAc, then the organic layer was washed with water and brine, dried (MgSO$_4$), and concentrated. Flash chromatography (silica 10% then 20% EtOAc/hexane) provided 4-1 as a brown oil. R$_f$ 0.33 (silica, 20% EtOAc/hexane).

$^1$H NMR (300 MHz, CDCl$_3$) δ 8.67 (br s, 1H), 7.55 (dd, J=8,1 Hz, 1H), 7.35 (dd, J=8, 1 Hz, 1H), 7.20–7.05 (m, 2H), 6.35 (m, 1H), 4.21 (q, J=7 Hz, 2H), 3.83 (s, 2H), 1.30 (t, J=7 Hz, 3H).

2-(Indol-2-yl)ethanol (4-2)

Ester 4-1 (0.54 g, 2.6 mmol) was dissolved in 13 mL CH$_2$Cl$_2$ at −78°, and DIBAL (1M in CH$_2$Cl$_2$, 5.8 ml, 5.8 mmol) was added dropwise. The mixture was stirred at −78° for 15 min then warmed to RT for 30 min and quenched in sat. aqueous Na/K tartrate. This solution was extracted with EtOAc. The organic layer was washed with brine, dried (Na$_2$SO$_4$), and concentrated. Flash chromatography (silica 50% EtOAc/hexane) provided 4-2 as a brown oil. R$_f$ 0.38 (silica, 50% EtOAc/hexane).

$^1$H NMR (300 MHz, CDCl$_3$) δ 8.43 (br s, 1H), 7.54 (dd, J=8, 1 Hz, 1H), 7.32 (dd, J=8, 1 Hz, 1H), 7.20–7.05 (m, 2H), 6.29 (m, 1H), 3.9 (q, J=5 Hz, 2H), 3.02 (t, J=5 Hz, 2H).

Methyl 4-[2-(Indol-2-yl)ethyloxy]benzoate (4-3)

Alcohol 4-2 (136 mg, 0.84 mmol), phenol 1-2 (128 mg, 0.84 mmol) and Ph$_3$P (277 mg, 1.06 mmol) were combined in 8 mL THF, and a solution of DIAD (0.22 mL, 1.1 mmol) in 5 mL THF was added dropwise during 1.5 h. After 2.5 h the mixture was diluted with EtOAc, washed with water/brine, 1N NaOH, and brine, dried (MgSO$_4$), and concentrated. Flash chromatography (silica 15% EtOAc/hexane) provided 4-3 as an oil. R$_f$ 0.14 (silica, 15% EtOAc/hexane).

$^1$H NMR (300 MHz, CDCl$_3$) δ 8.25 (br s, 1H), 8.01 (dd, J=9 Hz, 2H), 7.55 (dd, J=8, 1 Hz, 1H), 7.34 (dd, J=8, 1Hz, 1H), 7.20–7.05 (m, 2H), 6.97 (d, J=9 Hz, 2H), 6.34 (m, 1H), 4.34 (t, J=6 Hz, 2H), 3.89 (s, 3H), 3.28 (t, J=6 Hz, 2H).

4-[2-(Indol-2-yl)ethyloxy]benzoic acid (4-4)

Ester 4-3 (150 mg, 0.51 mmol) and 1N NaOH (1.3 mL, 1.3 mmol) were combined in 10 mL MeOH. After 16 h additional 1N NaOH (5 mL, 5 mmol) was added, and 7 h later, 5 mL more 1N NaOH. After a total of 2 d the mixture was heated at 50° for 1 h, then concentrated, redissolved in H$_2$O, washed with EtOAc, and the pH of the aqueous layer was adjusted to 1 with 20% KHSO$_4$. This was extracted with EtOAc, and this organic layer was washed with brine, dried (MgSO$_4$) and concentrated, providing 4-4 as a gray solid. R$_f$ 0.48 (silica, EtOAc).

$^1$H NMR (300 MHz, CD$_3$OD) δ 7.96 (d, J=9 Hz, 2H), 7.42 (ds J=8 Hz, 1H), 7.29 (dd, J=8, 1 Hz, 1H), 7.02 (d, J=9 Hz, 2H), 7.03–6.93 (m, 2H), 6.27 (s, 1H), 4.37 (t, J=7 Hz, 2H), 3.25 (t, J=7 Hz, 2H).

4-[2-(Indol-2-yl)ethyloxy]benzoyl-2(S)-phenylsulfonylamino-β-alanine methyl ester (4-5)

Acid 4-4 (100 mg, 0.36 mmol), amine 2-2 (105 mg, 0.36 mmol), EDC (88 mg., 0.46 mmol), HOBT (62 mg, 0.46 mmol) and NMM (137 μL, 1.2 mmol) were combined in 2 mL DMF. After 16 h the mixture was diluted with EtOAc, washed with water, sat. NaHCO$_3$, 5% KHSO$_4$, and brine, dried (MgSO$_4$) and concentrated. Flash chromatography (silica, 65% EtOAc/hexane) provided 4-5 as an oil. R$_f$ 0.32 (silica, 65% EtOAc/hexane).

$^1$H NMR (300 MHz, CDCl$_3$) δ 8.41 (br s, 1H), 7.83 (d, J=7 Hz, 2H), 7.74 (d, J=9 Hz, 2H), 7.60–7.43 (m, 4H), 7.34 (dd, J=8, 1 Hz, 1H), 7.20–7.02 (m, 2H), 6.93 (d, J=9 Hz, 2H), 6.72 (br t, 1H) 6.34 (m, 1H), 5.87 (d, J=8 Hz, 1H), 4.28 (t, J=6 Hz, 2H), 4.05 (m, 1H), 3.86 (m 1H), 3.67 (m, 1H), 3.60 (s, 3H), 3.26 (t, J=6 Hz, 2H).

4-[2-(Indol-2-yl)ethyloxy]benzoyl-2(S)-phenylsulfonylamino-β-alanine (4-6)

Ester 4-5 (147 mg, 0.28 mmol), and 1N LiOH (0.70 mL, 0.70 mmol), were combined in 3 mL THF. After 16 h the mixture was concentrated and purified by flash chromatography (silica, 33:20:1:1 EtOAc/EtOH/NH$_4$OH/H$_2$O) providing 4-6 as a white solid. R$_f$ 0.33 (silica, 33:20:1:1 EtOAc/EtOH/NH$_4$OH/H$_2$O).

$^1$H NMR (300 MHz, DMSO) δ 8.46 (br s, 1H), 7.77 (d, J=7 Hz, 2H), 7.71 (d, J=9 Hz, 2H), 7.60–7.46 (m, 3H), 7.41 (d, J=8 Hz, 1H), 7.29 (d, J=8 Hz, 1H), 7.02 (d, J=9 Hz, 2H), 7.02–6.86 (m, 4H), 6.26 (br s,1H), 4.35 (t, J=7 Hz, 2H), 3.60–3.20 (m), 3.19 (t, J=7 Hz, 2H).

SCHEME 5

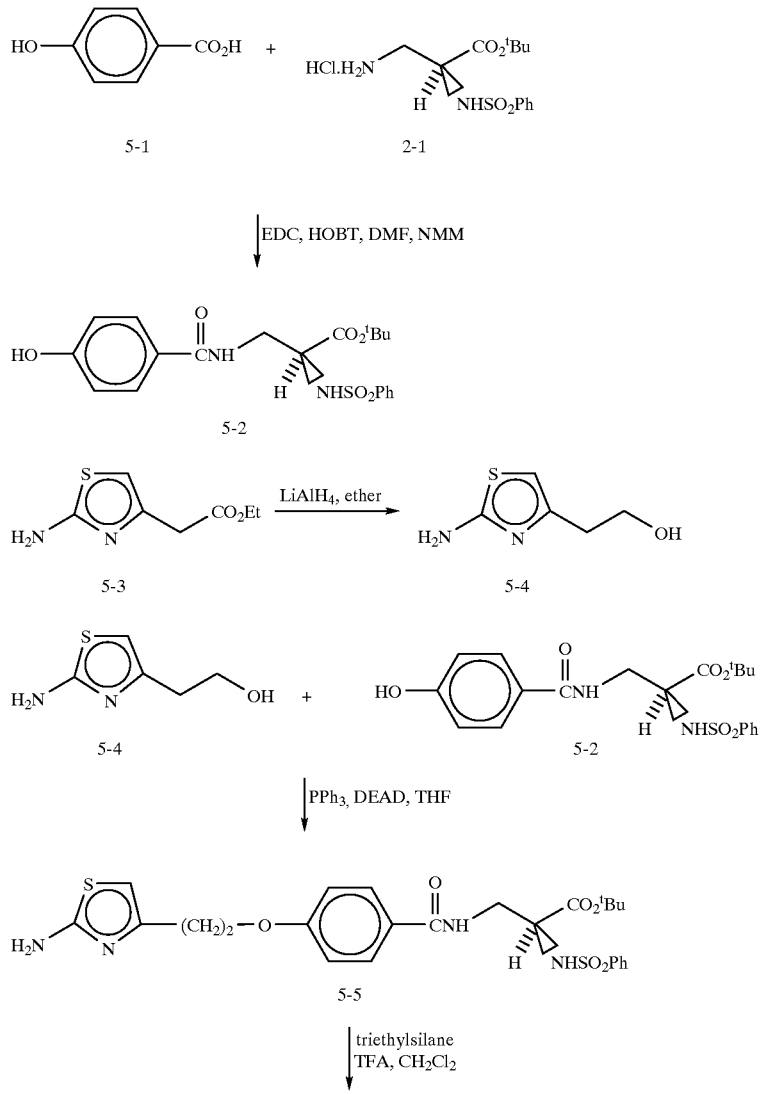

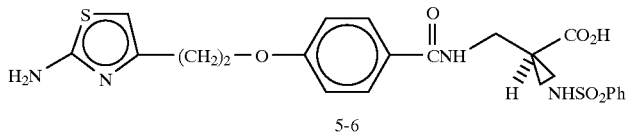

5-6

4-Hydroxybenzoyl-2(S)-phenylsulfonylamino-β-alanine tert-butyl ester (5-2)

To a stirred solution of 5-1 (0.41 g, 2.9 mmol; Aldrich), 2-1 (1.0 g, 2.9 mmol), HOBT (0.52 g, 3.9 mmol) NMM (0.65 mL, 5.9 mmol), and DMF (15 mL) at 0° C. was added EDC (0.74 g, 3.9 mmol) followed by removal of the cooling bath. After 20 h, the reaction mixture was diluted with EtOAc and then washed with $H_2O$ (2×), sat. $NaHCO_3$, 5% $KHSO_4$ and brine, dried ($MgSO_4$), filtered and concentrated. Flash chromatography (silica, 60% to 80% EtOAc/hexanes), then redissolving in EtOAc, washing with water (2×) and brine, drying, filtering and concentrating gave 5-2 as a white foam. $R_f$ 0.38 (silica, 60% EtOAc/hexanes).

$^1$H NMR (300 MHz, $CDCl_3$) δ 7.86 (m, 2H), 7.72 (d, J=9 Hz, 2H), 7.53 (m, 3H), 6.87 (d, J=9 Hz, 2H), 6.62 (m, 1H), 5.63 (d, J=7 Hz, 1H), 5.42 (m, 1H), 3.90 (m, 2H), 3.55 (m, 1H), 1.29 (s, 9H).

2-(2-Aminothiazol-4-yl)ethanol (5-4)

To a stirring suspension of 5-3 (2.0 g, 10.7 mmol; Fluka) in ether (54 mL) at ambient temperature was added $LiAlH_4$ (16.1 mL, 16.1 mmol; 1M/THF) dropwise. After complete addition, the reaction mixture was stirred for 30 min and then quenched by sequential addition of $H_2O$ (0.61 mL), 15% NaOH (0.61 mL), and $H_2O$ (1.83 mL). The reaction mixture was filtered through a celite pad and the filtrate concentrated to give 5-4 as a brown oil. $R_f$ 0.26 (silica, 5:1:1 $CH_2Cl_2/CH_3OH/AcOH$).

$^1$H NMR (400 MHz, DMSO) δ 6.81 (s, 1H), 3.76 (t, J=6 Hz, 2H), 2.88 (t, J=6 Hz, 2H).

4-[2-(2-Aminothiazol-4-yl)ethyloxy]benzoyl-2(S)-phenylsulfonylamino-βalanine tert-butyl ester (5-5)

To a stirred solution of 5-2 (0.14 g, 0.32 mmol) and $PPh_3$ (0.11 g, 0.41 mmol) in THF (2 mL) at ambient temperature was added a solution of 5-4 (56 μg, 0.39 mmol) DEAD (67 μL, 0.42 mmol) in THF (2 mL) dropwise over a 15 min period. After 72 h, the reaction mixture was diluted with EtOAc and then washed with $H_2O$, sat. $NaHCO_3$, 10% $KHSO_4$ and brine, dried ($MgSO_4$) and concentrated. After two flash columns: silica, 85% EtOAc/hexanes; silica, 5% to 30% isopropanol/$CHCl_3$), 5-5 was obtained as a yellow oiL $R_f$ 0.19 (silica, 85% EtOAc/hexanes).

$^1$H NMR (400 MHz, $CDCl_3$) δ 7.86 (m, 2H), 7.73 (d, J=9 Hz, 2H), 7.52 (m, 3H), 6.92 (d, J=9 Hz, 2H), 6.67 (m, 1H), 6.22 (s, 1H), 5.81 (m, 1H), 5.5 (m, 2H), 4.24 (t, J=6 Hz, 2H), 3.90 (m, 2H), 3.56 (m, 1H), 3.02 (t, J=6 Hz, 2H), 1.28 (s, 9H).

4-[2-(2-Aminothiazol-4-yl)ethyloxy]benzoyl-2(S)-phenylsulfonylamino-β-alanine (5-6)

A stirred solution of 5-5 (33 mg, 60 mmol), $CH_2Cl_2$ (0.5 mL), and triethylsilane (24 μL, 0.15 mmol) at ambient temperature was treated with TFA (0.5 mL). After 4 h, the solution was concentrated and the residual TFA removed azeotropically with toluene. Flash chromatography (silica, 10:0.1:0.1 ethanol/$NH_4OH/H_2O$) gave 5-6 as a white solid.

$^1$H NMR (400 MHz, $D_2O$+DCl) δ 7.49 (m, 2H), 7.30 (d, J=9 Hz, 2H), 7.08 (m, 3H), 6.73 (d, J=9 Hz, 2H), 4.11 (t, 2H), 3.97 (m, 1H), 3.50 (m, 1H), 3.38 (m, 1H), 3.20 (m, 1H) 2.82 (m, 2H).

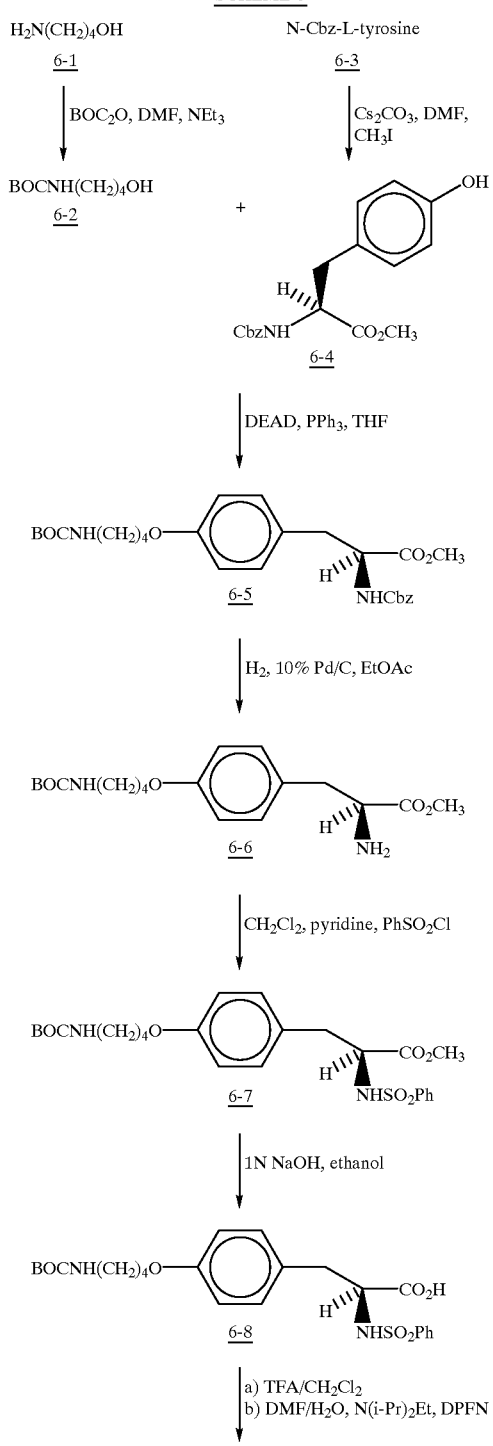

SCHEME 6

-continued

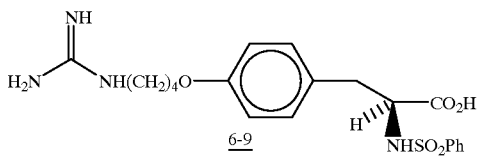

4-N-BOC-Aminobutanol (6-2)

To a stirred solution of 6-1 (Aldrich) (5.0 g, 56 mmol), NEt$_3$ (11.7 mL, 84 mmol), and DMF (150 mL) at 0° C. was added BOC$_2$O (14.7 g, 67 mmol) followed by removal of the cooling bath. After 1.0 h, the solution was diluted with EtOAc and then washed with 10% KHSO$_4$ and brine, dried (MgSO$_4$) and concentrated to give 6-2 as a colorless oil.

$^1$H NMR (300 MHz, CDCl$_3$) δ 3.68 (m, 2H), 3.15 (m, 2H), 1.60 (m, 4H), 1.47 (s, 9H).

N-Cbz-L-Tyrosine methyl ester (6-4)

A suspension of Cs$_2$CO$_3$ (0.65 g, 2.0 mmol), N-Cbz-L-tyrosine (1.3 g, 4.0 mmol; Bachem) and DMF (40 mL) at ambient temperature was treated with methyl iodide (0.5 mL, 4.0 mmol). After 2.0 h the reaction mixture was diluted with EtOAc and then washed with H$_2$O and brine, dried (MgSO$_4$) and concentrated. Flash chromatography (silica, 25% EtOAc/hexanes) gave 6-4 as a white solid. R$_f$ 0.53 (silica, 50% EtOAc/hexanes).

Methyl 2(S)-(N-Benzyloxycarbonylamino)-3-[4-(4-N-Boc-aminobutyloxy)phenyl]propionate (6-5)

To a stirred solution of 6-4 (500 mg, 1.5 mmol), PPh$_3$ (0.5 g, 1.9 mmol) and THF (10 mL) was added a solution of 6-2 (430 mg, 2.3 mmol), DEAD (326 mg, 1.9 mmol), and THF (10 mL) dropwise over a 30 min period. After 2.0 h the solution was diluted with EtOAc and then washed with H$_2$O, 1N NaOH, 10% KHSO$_4$ and brine, dried (MgSO$_4$) and concentrated. Flash chromatography (silica, 25% EtOAc/hexanes) gave 6-5 as a white solid. R$_f$ 0.50 (silica, 50% EtOAc/hexanes).

$^1$H NMR (300 MHz, CD$_3$OD) δ 7.22 (m, 5H), 7.02 (d, J=9 Hz, 2H), 6.72 (d, J=9H, 2H), 4.97 (m, 2H), 4.34 (m, 1H), 3.89 (m, 2H), 3.63 (s, 3H), 3.02 (m, 2H), 3.01 (m, 1H), 2.81 (m, 1H), 1.73 (m, 2H), 1.62 (m, 2H), 1.47 (s, 9H).

Methyl 2(S)-amino-3-[4-(4-N-Boc-aminobutyloxy)phenyl]propionate (6-6)

A mixture of 6-5 (500 mg, 0.99 mmol), 10% Pd/C (250 mg), and EtOAc (5 mL) was stirred under a hydrogen atmosphere (1 atm) at ambient temperature for 1.0 h. The reaction mixture was then filtered through a celite pad and the filtrate concentrated to give 6-6 as a yellow solid. R$_f$ 0.36 (silica, 10:1:1 CH$_2$Cl$_2$/CH$_3$OH/AcOH).

$^1$H NMR (300 MHz, CD$_3$OD) δ 7.02 (d, J=9 Hz, 2H), 6.80 (d, J=9 Hz, 2H), 3.90 (m, 2H), 3.63 (s, 3H), 3.03 (m, 2H), 2.85 (m, 2H), 1.73 (m, 2H), 1.62 (m, 2H), 1.47 (s, 9H).

Methyl 2(S)-phenylsulfonylamino-3-[4-(4-N-Boc-aminobutyloxy)-phenyl]propionate (6-7)

To a stirred solution of 6-6 (350 mg, 0.95 mmol), CH$_2$Cl$_2$ (5 mL), and pyridine (229 μL, 3.0 mmol) at 0° C. was added phenylsulfonyl chloride (145 μL, 1.2 mmol), followed by removal of the cooling bath. After 20 h the reaction mixture was diluted with EtOAc and then washed with H$_2$O, sat. NaHCO$_3$, 10% KHSO$_4$ and brine, dried (MgSO$_4$) and concentrated. Flash chromatography (silica, 30% EtOAc/hexanes) gave 6-7 as a colorless oil. R$_f$ 0.31 (silica, 30% EtOAc/hexanes).

$^1$H NMR (300 MHz, CD$_3$OD) δ 7.25–7.00 (m, 5H), 6.52 (d, J=9 Hz, 2H), 6.30 (d, J=9 Hz, 2H), 3.58 (m, 1H), 3.50 (t, 2H), 2.97 (s, 3H), 2.67 (t, 2H), 2.45 (dd, 1H), 2.32 (dd, 1H), 1.32 (m, 2H), 1.21 (m, 2H), 1.01 (s, 9H).

2(S)-Phenylsulfonylamino-3-[4-(4-N-Boc-aminobutyloxy)phenyl]-propionic acid (6-8)

A solution of 6-7 (350 mg, 0.69 mmol), 1N NaOH (1.5 mL), and ethanol (3.5 mL) was stirred at ambient temperature for 1.0 h. The solution was then acidified with 10% KHSO$_4$ and extracted with EtOAc. The EtOAc portion was washed with brine, dried (MgSO$_4$) and concentrated to give 6-8 as a white solid. R$_f$ 0.71 (silica, 10:1:1 CH$_2$Cl$_2$/CH$_3$OH/AcOH).

$^1$H NMR (300 MHz, CD$_3$OD) δ 7.60–7.30 (m, 5H), 6.92 (d, J=9 Hz, 2H), 6.63 (d, J=9 Hz, 2H), 3.87 (m, 3H), 3.02 (t, 2H), 2.88 (dd, 1H), 2.68 (dd, 1H), 1.70 (m, 2H), 1.58 (m, 2H), 1.45 (s, 9H).

2(S)-Phenylsulfonylamino-3-[4-(4-guanidobutyloxy)phenyl]propionic acid (6-9)

A solution of 6-8 (300 mg, 0.60 mmol), TFA (3 mL), and CH$_2$Cl$_2$ (3 mL) was stirred at ambient temperature for 1.0 h. The solution was concentrated followed by azeotropic removal of the residual TFA with toluene. The residue was dissolved in 1:1 DMF/H$_2$O (3.0 mL) and then treated with N(i-Pr)$_2$Et (316 mL, 1.8 mmol) and DPFN (1.33 mg, 0.91 mmol). After heating at 40° C. for 2.0 h the reaction mixture was concentrated. Flash chromatography (silica, 10/0.1/0.1 to 10/1/1 ethanol/NH$_4$OH/H$_2$O) gave 6-9 as a white solid. R$_f$ 0.33 (silica, 10:1:1 ethanol/NH$_4$OH/H$_2$O).

$^1$H NMR (400 MHz, CD$_3$OD) δ 7.75–7.45 (m, 5H), 7.06 (d, J=9 Hz, 2H), 6.78 (d, J=9 Hz, 2H), 4.02 (m, 3H), 3.30 (m, 2H), 3.00 (dd, 1H), 2.79 (dd, 1H), 1.77 (m, 4H).

SCHEME 7

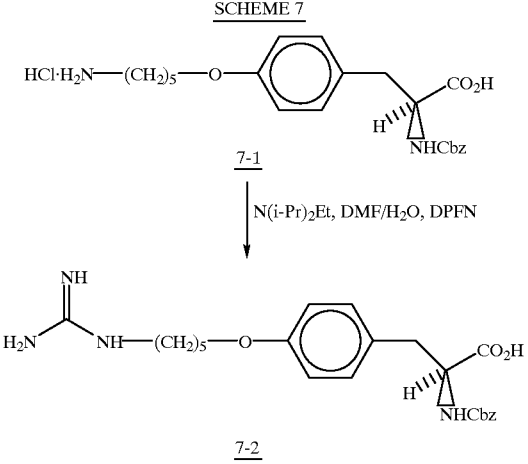

2-S-(N-Benzyloxycarbonylamino)-3-[4-(5-guanidopentyloxy)-phenyl]propionic acid (7-2)

A stirred solution of 7-1 (225 mg, 0.56 mmol; for preparation see Duggan, et al, European Publication 478362), diisopropylethylamine (0.6 mL, 3.4 mmol), DMF (4 mL), and H$_2$O (1 mL) was treated with 3,5-dimethyl-1-pyrazolylformaminidium nitrate (DPFN) (0.68 g, 3.4 mmol) then heated at 60° C. for 20 h. Concentration followed by flash chromatography (silica, ethanol/NH$_4$OH/H$_2$O 10:0.3:0.3) gave 7-2 as a white solid. R$_f$ 0.59 (silica, 10:1:1 ethanol/NH$_4$OH/H$_2$O).

$^1$H NMR (400 MHz, CD$_3$OD) δ 7.30 (m, 5H), 7.07 (d, 2H), 6.73 (d, 2H), 5.07 (d, 1H), 4.98 (d, 1H), 4.21 (m, 1H), 3.96 (t, 2H), 3.16 (t, 2H), 3.08 (dd, 1H), 2.89 (dd, 1H), 1.80–1.50 (m, 6H).

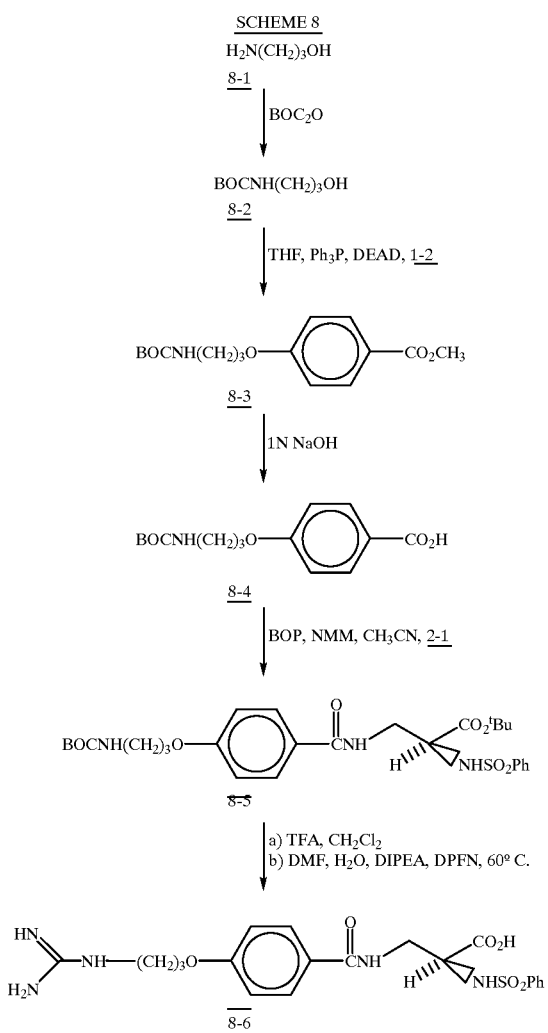

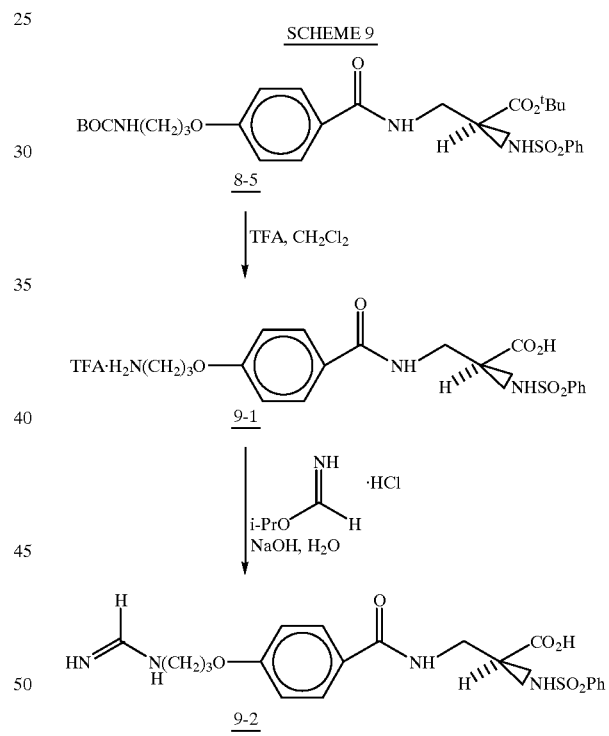

3-(N-BOC-Amino)propanol (8-2)

To a stirred solution of 3-aminopropanol 8-1 (Aldrich) (15 g, 0.2 mol), NEt$_3$ (42 mL, 0.3 mol) and DMF (400 mL) at 0° C. was added BOC$_2$O (52 g, 0.24 mol). After stirring at 0° C. for 6 h the reaction mixture was diluted with ether and then washed with H$_2$O (2×), sat. NaHCO$_3$, 5% KHSO$_4$ and brine, dried (MgSO$_4$) and concentrated to give 8-2 as a colorless oil.

TLC R$_f$ 0.42 (silica, 20% EtOAc/hexanes); $^1$H NMR (300 MHz, CDCl$_3$) δ 3.68 (t, J=7 Hz, 2H), 3.30 (t, J=7 Hz, 2H), 1.69 (m, 2H), 1.45 (s, 9H).

Methyl 4-(3-N-BOC-Amninopropyloxy)benzoate (8-3)

Following the procedure for coupling 1-1 to 1-2, 8-2 (13.8 g, 79 mmol) was coupled to 1-2 (8.0 g, 53 mmol) to give 8-3 as a yellow oil after flash chromatography (silica, 5% EtOAc/hexanes).

TLC R$_f$=0.38 (silica, 20% EtOAc/hexanes); $^1$H NMR (300 MHz, CDCl$_3$) δ 8.00 (d, J=9 Hz, 2H), 6.92 (d, J=9 Hz, 2H), 4.70 (m, 1H), 4.08 (m, 2H), 3.88 (s, 3H), 3.33 (m, 2H), 2.00 (m, 2H), 1.46 (s, 9H).

4-(3-N-BOC-Aminopropyloxy)benzoic acid (8-4)

A solution of 8-3 (16 g, 52 mmol), 1N NaOH (100 mL), and ethanol (150 mL) was stirred at ambient temperature for 20 h. The reaction mixture was acidified with 10% KHSO$_4$ and then extracted with EtOAc. The EtOAc portion was washed with brine, dried (MgSO$_4$) and concentrated. Trituration of the residue with ether gave 8-4 as a white solid.

$^1$H NMR (300 MHz, CD$_3$OD) δ 7.87 (d, J=9 Hz, 2H), 6.88 (d, J=9 Hz, 2H), 3.98 (t, J=6 Hz, 2H), 3.15 (t, J=6 Hz, 2H), 1.86 (m, 2H), 1.33 (s, 9H).

4-[3-(N-BOC-Amino)propyloxy]benzoyl-2(S)-phenylsulfonylamino-β-alanine tert-butyl ester (8-5)

Following the procedure for coupling 1-4 to 2-1, 8-4 (300 mg, 1.0 mmol) was coupled to 2-1 (372 mg, 1.2 mmol) to furnish 8-5 as a colorless oil after flash chromatography (silica, 50% EtOAc/hexanes).

TLC R$_f$ 0.33 (silica, 50% EtOAc/hexanes); $^1$H NMR (300 MHz, 10% CD$_3$OD/CDCl$_3$) δ 7.8 (m, 2H), 7.76 (d, J=9 Hz, 2H), 7.51 (m, 3H), 6.92 (d, J=9 Hz, 2H), 4.10 (m, 2H), 4.00–3.60 (m, 3H), 3.32 (m, 2H), 2.00 (m, 2H), 1.45 (s, 9H), 1.28 (s, 9H).

4-(3-Guanidopropyloxy)benzoyl-2(S)-phenylsulfonylamino-β-alanine (8-6)

Following the procedure for converting 2-3 to 2-4, 8-5 (300 mg, 0.55 mmol) furnished 8-6 as a white solid after flash chromatography (silica, 10:1:1 ethanol/H$_2$O/NH$_4$OH).

TLC R$_f$ 0.28 (silica, 10:1:1 ethanol/H$_2$O/NH$_4$OH); $^1$H NMR (400 MHz, D$_2$O) δ 7.65 (m, 2H), 7.43 (d, J=9 Hz, 2H), 7.24 (m, 3), 6.90 (d, J=9 Hz, 2H), 4.13 (m, 1H), 4.10 (m, 2H), 3.68 (m, 1H), 3.52 (m, 1H), 3.40–3.25 (m, 3H), 2.00 (m, 2H).

4-(3-Aminopropyloxy)benzoyl-2(S)-phenylsulfonylamino-β-alanine trifluoroacetate (9-1)

8-5 (497 mg, 1.04 mmol) in 5 mL CH$_2$Cl$_2$ was treated with 5 mL TFA at 0° for 30 min then RT for 10 min. Concentration provided 9-1 as a yellow oil. R$_f$ 0.52 (silica, 10:1:1 ethanol/NH$_4$OH/H$_2$O).

$^1$H NMR (400 MHz, CD$_3$OD) δ 7.9–7.6 (m, 4H) 7.55–7.45 (m, 3H), 7.02 (d, 2H), 4.18 (t, 2H), 3.70 (m, 1H), 3.48 (m, 1H), 3.16 (t, 2H), 3.05, (m, 1H), 2.16 (qn, 2H).

4-[3-(Formamidino)propyloxy]benzoyl-2(S)-phenylsulfonylamino-β-alanine (9-2)

The TFA salt 9-1 (80 mg, 0.19 mmol) was dissolved in water at 0° and the pH of the solution was adjusted to 9 by addition of 1N NaOH. Isopropyl formimidate hydrochloride (130 mg, 0.95 mmol) was added in two portions 10 min apart maintaining pH 9 with additional 1N NaOH. After 60 min at 0° the reaction was warmed to RT for 90 min, then lyophylized. Preparative HPLC (C-18, 0.1% TFA $H_2O$/$CH_3CN$) provided 9-2 as a white solid.

$^1$H NMR (400 MHz, $D_2O$) 7.81 (s, 1H), 7.77 (d, J=7 Hz, 2H), 7.60 (d, J=9 Hz, 2H), 7.46–7.35 (m, 3H), 7.05 (d, J=9 Hz, 2H), 4.23 (t, J=6 Hz, 2H), 3.91 (dd, J=10, 4 Hz, 1H), 3.68 (dd, J=14, 4 Hz, 1H), 3.56 (t, J=6 Hz, 2H), 3.40 (dd, J=14, 10, 1H), 2.19 (qn, J=6 Hz, 2H).

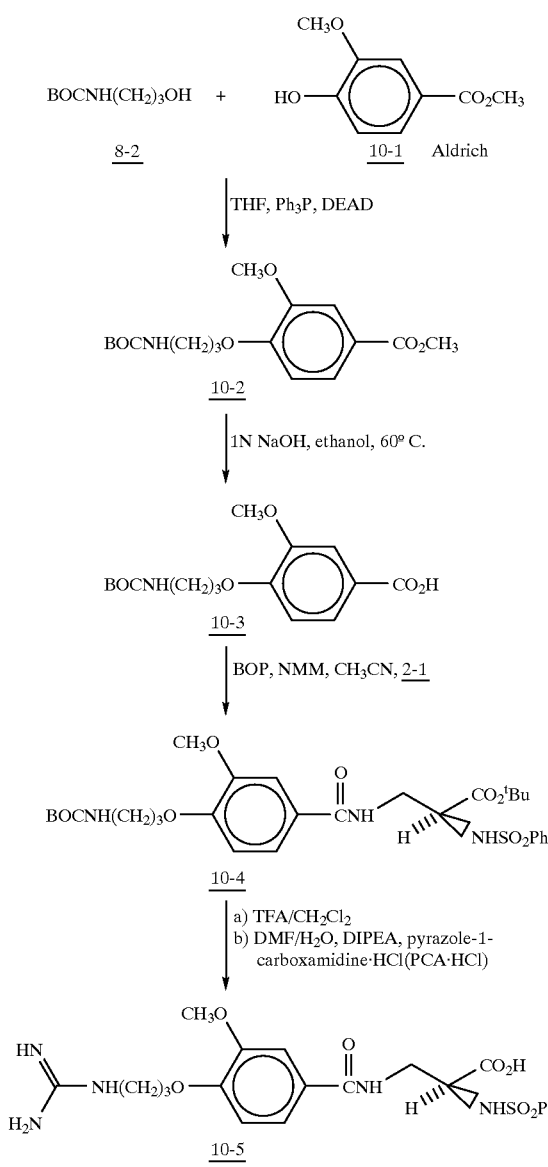

Methyl 3-methoxy-4-(3-N-BOC-aminopropyloxy)benzoate (10-2)

Following the procedure for coupling 1-1 to 1-2, 8-2 (2.8 g, 16.1 mmol) was coupled to 10-1 (Aldrich) (1.9 g, 10.7 mmol) to give 10-2 as a colorless oil after flash chromatography (silica, 20% EtOAc/hexanes).

TLC $R_f$ 0.18 (silica, 20% EtOAc/hexanes); $^1$H NMR (300 MHz, $CDCl_3$) δ 7.70 (dd, J=9 and 2 Hz, 1H), 7.57 (d, J=2 Hz, 1H), 6.89 (d, J=9 Hz, 1H), 5.52 (m, 1H), 4.17 (m, 2H), 3.96 (s, 3H), 3.92 (s, 3H), 3.40 (m, 2H), 2.08 (m, 2H), 1.48 (s, 9H).

3-Methoxy-4-(3-N-BOC-aminopropyloxy)benzoic acid (10-3)

A solution of 10-2 (3.5 g, 10.2 mmol), 1N NaOH (20 mL) and ethanol (30 mL) was heated at 60° C. for 2.0 h. The cooled reaction mixture was acidified with 10% $KHSO_4$ and extracted with EtOAc. The organic portion was washed with brine, dried ($MgSO_4$) and concentrated. The residue was triturated with $Et_2O$ and filtered to give 10-3 as a white solid.

$^1$H NMR (400 MHz, $CD_3OD$) δ 7.68 (dd, J=9, 2 Hz, 1H), 7.60 (d, J=2 Hz, 1H), 7.02 (d, J=9 Hz, 1H), 4.15 (m, 2H), 3.92 (s, 3H), 3.30 (m, 2H), 2.03 (m, 2H), 1.47 (s, 9H).

3-Methoxy-4-[3-(N-BOC-amino)propyloxy]benzoyl-2(S)-phenylsulfonylamino-β-alaninetert-butyl ester (10-4)

Following the procedure for coupling 1-4 to 2-1, 10-3 (230 mg, 0.71 mmol) was coupled to 2-1 (215 mg, 0.71 mmol) to give 10-4 as a white solid after flash chromatography (silica, 50% EtOAc/hexanes).

TLC $R_f$ 0.31 (silica, 50% EtOAc/hexanes); $^1$H NMR (300 MHz, $CD_3OD$) δ 7.80–7.30 (m, 7H), 6.93 (d, J=9 Hz, 1H), 6.61 (m, 1H), 4.05 (m, 3H), 3.82 (s, 3H), 3.61 (m, 1H), 3.43 (m, 1H), 3.22 (m, 2H), 1.92 (m, 2H), 1.47 (s, 9H), 1.18 (s, 9H).

3-Methoxy-4-[3-guanidinopropyloxy]benzoyl-2(S)-phenylsulfonylamino-β-alanine (10-5)

A solution of 10-4 (350 mg, 0.61 mmol), TFA (3 mL) and $CH_2Cl_2$ (3 mL) was stirred at ambient temperature for 3.0 h. The reaction mixture was concentrated and the residual TFA removed azeotropically with toluene. The residue was dissolved in DMF (1.5 mL) and $H_2O$ (1.5 mL) and treated sequentially with DIPEA (317 μl, 1.8 mmol) and pyrazole-1-carboxamidine-HCl (PCA-HCl) (134 mg, 0.92 mmol). After 20 h at ambient temperature the reaction mixture was concentrated. Flash chromatography (silica, 10:1:1 ethanol/$NH_4OH$/$H_2O$) gave 10-5 as a white solid.

TLC $R_f$=0.18 (silica, 10:1:1 ethanol/$NH_4OH$/$H_2O$); $^1$H NMR (400 MHz, $CD_3OD$) δ 7.90–7.40 (m, 7H), 7.08 (d, J=9 Hz, 1H), 4.27 (m, 1H), 4.22 (m, 2H), 3.96 (s, 3H), 3.82–3.45 (m, 4H), 2.15 (m, 2H).

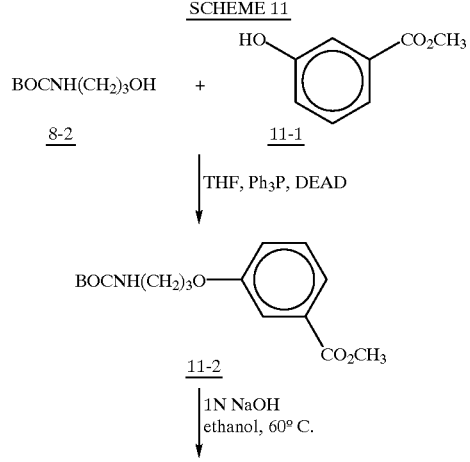

6H), 7.18 (m, 1H), 4.28 (m, 1H), 4.18 (m, 2H), 3.73 (m, 1H), 3.56 (m, 1H), 3.47 (m, 2H), 2.13 (m, 2).

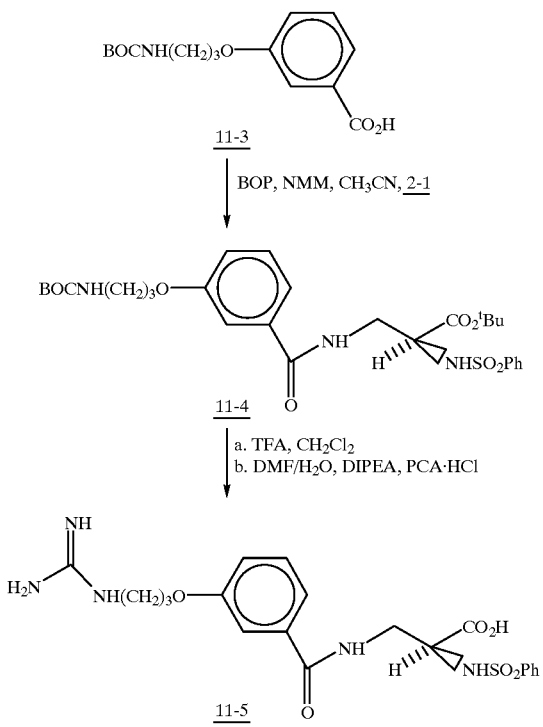

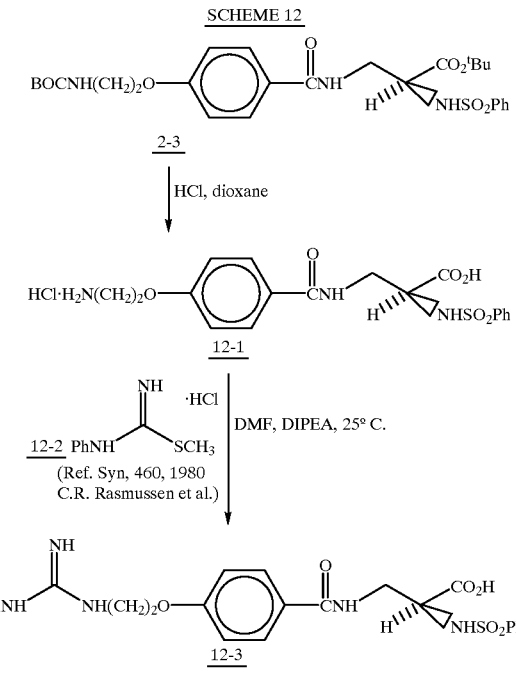

Methyl 3-(3-N-BOC-Aminopropyloxy)benzoate (11-2)

Following the procedure for coupling 1-1 to 1-2, 8-2 (2.8 g, 16.1 mmol) was coupled to 11-1 (Aldrich) (1.6 g, 10.7 mmol) to give 11-2 as a colorless oil after flash chromatography (silica, 15% EtOAc/hexanes).

TLC R$_f$ 0.28 (silica, 15% EtOAc/hexanes); $^1$H NMR (400 MHz, CD$_3$OD) δ 7.62 (m, 1H), 7.56 (m, 1H), 7.40 (m, 1H), 7.19 (m, 1H), 4.09 (m, 2H), 3.93 (s, 3H), 3.27 (m, 2H), 1.99 (m, 2H), 1.47 (s, 9H).

3-(3-N-BOC-Aminopropyloxy)benzoic acid (11-3)

A solution of 11-2 (3.3 g, 10.7 mmol), 1N NaOH (30 mL) and ethanol (50 mL) was heated at 60° C. for 20 h. The cooled reaction mixture was acidified with 10% KHSO$_4$ and then extracted with EtOAc. The organic portion was washed with brine, dried (MgSO$_4$) and concentrated to give 11-3 as a white solid.

$^1$H NMR (300 MHz, CD$_3$OD) δ 7.63 (m, 1H), 7.58 (m, 1H), 7.40 (m, 1H), 7.18 (m, 1H), 4.08 (m, 2H), 3.27 (m, 2H), 2.00 (m, 2H), 1.47 (s, 9H).

3-[3-(N-BOC-Aminopropyloxy)]benzoyl-2(S)-phenylsulfonylamino-β-alanine tert-butyl ester (11-4)

Following the procedure for coupling 1-4 to 2-1, 11-3 (2.86 mg, 1.0 mmol) was coupled to 2-1 (296 mg, 1.0 mmol) to give 11-4 as a colorless oil after flash chromatography (silica, 50% EtOAc/hexanes).

TLC R$_f$=0.27 (silica, 50% EtOAc/hexanes); $^1$H NMR (300 MHz, CD$_3$OD) δ 7.67 (m, 2H), 7.32 (m, 3H), 7.13 (m, 3H), 6.91 (m, 1H), 4.03 (m, 1H), 3.95 (m, 2H), 3.55 (m, 1H), 3.39 (m, 1H), 3.12 (m, 2H), 1.88 (m, 2H), 1.32 (s, 9H), 1.16 (s, 9H).

3-[3-(Guanidino)propyloxy]benzoyl-2(S)-phenylsulfonylamino-β-alanine (11-5)

Following the procedure for converting 10-4 to 10-1, 11-4 (350 mg, 0.64 mmol) was heated at 40° C. for 3.0 h to give 11-5 as a white solid after flash chromatography (silica, 10:1:1 ethanol/NH$_4$OH/H$_2$O).

TLC R$_f$=0.28 (silica, 10:1:1 ethanol/NH$_4$OH/H$_2$O); $^1$H NMR (400 MHz, CD$_3$OD) δ 7.77 (m, 2H), 7.60–7.25 (m, 4-(2-Aminoethyloxy)benzoyl-2(S)-phenylsulfonylamino-β-alanine-HCl (12-1)

A suspension of 2-3 (105 mg, 0.19 mmol) in 6N HCl (5 mL) was treated with dioxane (5 mL) to effect a homogeneous solution. After stirring for 20 h at ambient temperature, the solvents were evaporated and the resulting residue azeotroped with toluene to afford 12-1 as a colorless solid.

TLC R$_f$ 0.48 (silica, 9:0.5:0.5 ethanol/H$_2$O/NH$_4$OH). $^1$H NMR (300 MHz, CD$_3$OD) δ 7.82 (m, 2H), 7.78 (d, J=9H, 2H), 7.48 (m, 3H), 7.07 (d, J=9 Hz, 2H), 4.30 (m, 2H), 4.19 (m, 1H), 3.73 (m, 1H), 3.48 (m, 1H), 3.40 (m, 2H).

4-[2-(N-Phenylguanidino)ethyloxy]benzoyl-2(S)-phenylsulfonylamino-β-alanine (12-3)

A mixture of 12-1 (110 mg, 0.25 mmol), 12-2 (147 mg, 0.50 mmol), DIPEA (174 μL, 1.0 mmol) and DMF (5 mL) was stirred for 24 h at ambient temperature. Concentration and flash chromatography (silica, 9.5:0.25:0.25 ethanol/NH$_4$OH/H$_2$O) gave 12-3 as a colorless solid.

TLC R$_f$ 0.50 (silica, 9.5:0.25:0.25 ethanol/NH$_4$OH/H$_2$O); $^1$H NMR (400 MHz, CD$_3$OD) δ 7.77 (m, 2H), 7.72 (d, J=9 Hz, 2H), 7.60–7.20 (m, 8H), 7.02 (d, J=9 Hz, 2H), 4.70 (m, 1H), 4.22 (m, 2H), 3.73 (m, 2H), 3.67 (m, 1H), 3.56 (m, 1H).

SCHEME 13

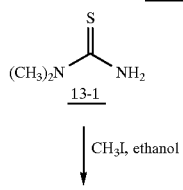

| CH$_3$I, ethanol

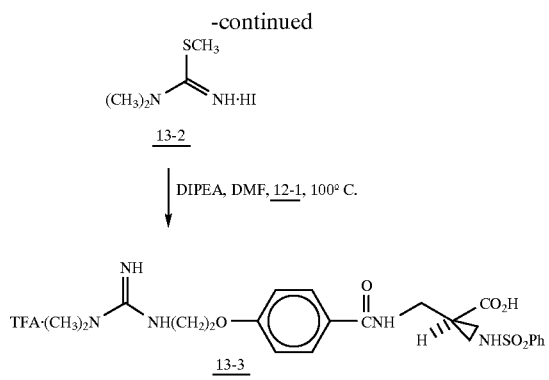

N,N-Dimethylthiomethyl amidine.HI (13-2)

The thiourea 13-1 (TransWorld) (5.0 g, 48 mmol) was suspended in ethanol (50 mL) at ambient temperature and treated with methyl iodide (4.5 mL, 72 mmol). After 2.0 h the reaction mixture was concentrated and the residue triturated with ether to give 13-2 as a pale yellow solid. mp=97–100° C.

$^1$H NMR (300 MHz, CD$_3$OD) δ 3.31 (s, 3H), 3.27 (s, 3H), 2.68 (s, 3H).

4-[2-(N,N-Dimethylguanidino)ethyloxy]benzoyl-2(S)-phenylsulfonylamino-β-alanine.TFA salt (13-3)

A solution of 13-2 (246 mg, 1.0 mmol), 12-1 (222 mg, 0.5 mmol), DIPEA (261 µL, 1.5 mmol) and DMF (5 mL) was heated at 100° C. for 18 h. The reaction mixture was then concentrated. Flash chromatography (silica, 9:0.5:0.5 to 9:1:1 ethanol/H$_2$O/NH$_4$OH) gave 13-3 as a colorless solid after lyophilization.

TLC R$_f$ 0.22 (silica, 9:1:1 ethanol/NH$_4$OH/H$_2$O); $^1$H NMR (300 MHz, CD$_3$OD) δ 7.88 (m, 2H), 7.80 (m, 2H), 7.52 (m, 3H), 7.00 (d, J=9 Hz, 2H), 4.20 (m, 2H), 3.80–3.50 (m, 4H), 3.30 (bs, 6H), 3.03 (s, 3H).

SCHEME 14

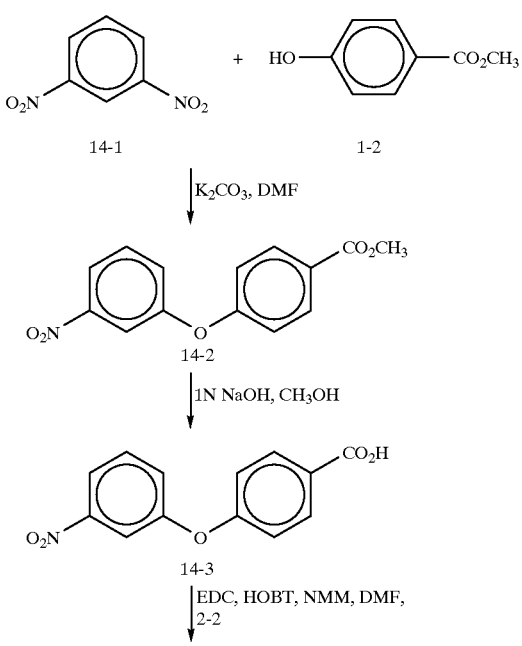

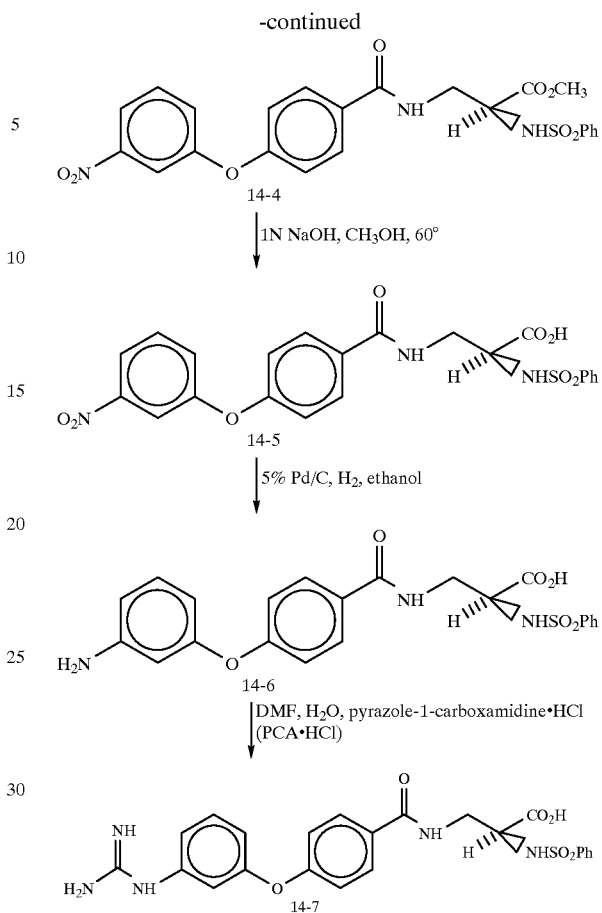

Methyl 4-(nitrophen-3-yloxy)benzoate (14-2)

A mixture of 14-1 (Aldrich) (1.6 g, 10 mmol), 1-2 (1.5 g, 10 mmol), K$_2$CO$_3$ (1.4 g, 10 mmol) and DMF (20 mL) was refluxed for 7.0 h. After cooling most of the DMF was removed in vacuo. The dark residue was diluted with ether and then washed with H$_2$O and brine, dried (MgSO$_4$) and concentrated. Flash chromatography (silica, 20% ether/hexanes) gave 14-2 as a yellow solid.

TLC R$_f$ 0.16 (silica, 20% ether/hexanes); $^1$H NMR (300 MHz, CDCl$_3$) δ 8.10 (d, J=9 Hz, 2H), 8.03 (m, 1H), 7.87 (m, 1H), 7.55 (m, 114), 7.40 (m, 1H), 7.06 (d, J=9 Hz, 2H), 3.93 (s, 3H).

4-(Nitrophen-3-yloxy)benzoic acid (14-3)

A solution of 14-2 (160 mg, 0.58 mmol), 1N NaOH (5.8 mL) and CH$_3$OH (10 mL) was stirred at ambient temperature for 24 h. The reaction mixture was concentrated and the residue dissolved in H$_2$O and washed with ether. The aqueous portion was then acidified with NaHSO$_4$ and extracted with EtOAc (2x). The combined EtOAc portions were dried (MgSO$_4$) and then concentrated to give 14-3 as a pale yellow solid.

$^1$H NMR (300 MHz, CDCl$_3$) δ 8.18 (d, J=9 Hz, 2H), 8.07 (m, 1H), 7.91 (m, 1H), 7.58 (m, 1H), 7.42 (m, 1H), 7.10 (d, J=9 Hz, 2H).

4-(Nitrophen-3-yloxy)benzoyl-2(S)-phenylsulfonylamino-β-alanine methyl ester (14-4)

A solution of 14-3 (340 mg, 1.3 mmol), 2-2 (386 mg, 1.3 mmol), HOBT (271 mg, 1.8 mmol), and DMF (6 mL) at −15° C. was treated with EDC (339 mg, 1.8 mmol). The pH of the solution was adjusted to about 8.0 with NMM followed by removal of the cooling bath. After 20 h the reaction mixture was concentrated and the residue dissolved in EtOAc. The EtOAc solution was washed with H₂O, sat. NaHCO₃ and brine, dried (MgSO₄) and concentrated. Flash chromatography (silica, 5% to 10% acetone/CH₂Cl₂) gave 14-4 as a colorless foam.

TLC R_f 0.14 (silica, 5% acetone/CH₂Cl₂); ¹H NMR (300 MHz, CDCl₃) δ 8.01 (m, 1H), 7.85 (m, 5H), 7.53 (m, 4H), 7.36 (m, 1H), 7.08 (d, J=9 Hz, 2H), 6.80 (m, 1H), 5.80 (m, 1H), 4.10 (m, 1H), 3.93 (m, 1H), 3.69 (m, 1H), 3.67 (s, 3H).

4-(Nitrophen-3-yloxy)benzoyl-2(S)-phenylsulfonylamino-β-alanine (14-5)

Following the procedure for converting 14-2 to 14-3, 14-4 (608 mg, 1.2 mmol) was saponified at 60° C. to give 14-5 as a pale yellow solid.

¹H NMR (300 MHz, CD₃OD) δ 8.05 (m, 1H), 7.85 (m, 5H), 7.65 (m, 1H), 7.48 (m, 4H), 7.12 (d, J=9 Hz, 2H), 4.21 (m, 1H), 3.75 (m, 1H), 3.52 (m, 1H).

4-(Aminophen-3-yloxy)benzoyl-2(S)-phenylsulfonylamino-β-alanine (14-6)

A mixture of 14-5 (560 mg, 1.2 mmol), 5% Pd/C (110 mg), and ethanol (50 mL) was stirred under a hydrogen atmosphere (1 atm) at ambient temperature for 8 h. Some precipitate had formed so the mixture was heated to dissolve the solid and then filtered hot through a celite pad to remove the catalyst. Concentration of the filtrate gave 14-6 as a colorless solid.

TLC R_f 0.85 (silica, 9:0.5:0.5 ethanol/NH₄OH/H₂O; ¹H NMR (300 MHz, CD₃OD) δ 7.83 (d, J=7 Hz, 2H), 7.72 (d, J=9 Hz, 2H), 7.46 (m, 3H), 7.10 (m, 1H), 6.98 (d, J=9 Hz, 2H), 6.55 (m, 1H), 6.42 (m, 1H), 6.35 (m, 1H), 4.17 (m, 1H), 3.72 (m, 1H), 3.50 (m, 1H).

4-(Guanidinophen-3-yloxy)benzoyl-2(S)-phenylsulfonylamino-β-alanine (14-7)

A solution of 14-6 (45 mg, 0.10 mmol), PCA.HCl (14 mg, 0.1 mmol) and DMF/H₂O (1:1; 1 mL) was heated at 120° C. for 20 h. Concentration and flash chromatography (silica, 9:0.5:0.5 ethanol/NH₄OH/H₂O) gave 14-7 as a colorless solid.

TLC R_f 0.20 (silica, 9:0.5:0.5 ethanol/NH₄OH/H₂O); ¹H NMR (300 MHz, CD₃OD/40% NaOD/D₂O) δ 7.80 (m, 4H), 7.31 (m, 4H), 7.00 (d, J=9 Hz, 2H), 6.79 (m, 1H), 6.68 (m, 1H), 6.60 (m, 1H), 3.67 (m, 2H), 3.35 (m, 1H).

SCHEME 15

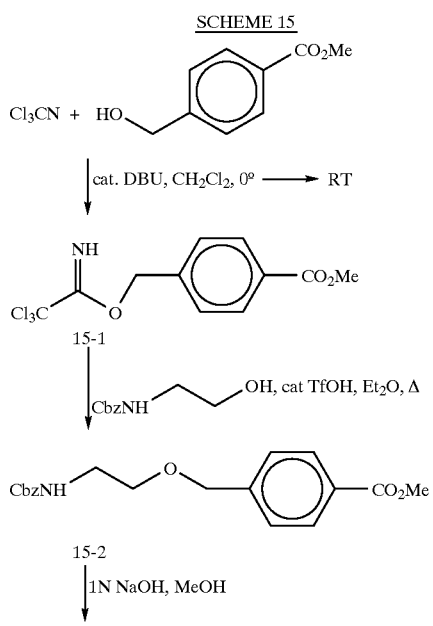

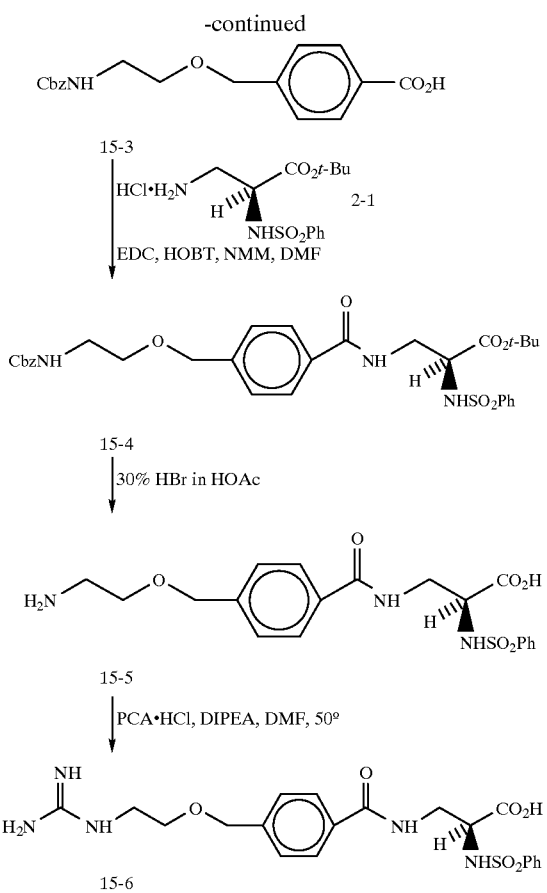

Methyl 4-(trichloromethyliminooxymethyl)benzoate (15-1)

Methyl 4-hydroxmethylbenzoate (Aldrich), (1.22 g, 7.35 mmol), trichloroacetonitrile (0.81 mL, 8.1 mmol), and DBU (0.11 mL, 0.74 mmol) were combined in CH₂Cl₂ at 0°. After warming to RT for 3 h the reaction mixture was concentrated and purified by flash chromatography (silica, 40% EtOAc/hex) providing 15-1.

R_f 0.77 (silica, 50% EtOAc/hexane); ¹H NMR (300 MHz, CDCl₃) δ 8.42 (s, 1H), 8.06 (d, J=8 Hz, 2H), 7.50 (d, J=9 Hz, 2H), 5.40 (s, 2H), 3.92 (s, 3H).

Methyl 4-[2-(N-Cbz-amino)ethyloxymethyl]benzoate (15-2)

Imidate 15-1 (1.5 g, 4.8 mmol) and N-Cbz-aminoethanol (1.0 g, 5.1 mmol) were combined with Et₂O (50 ml), then TfOH (100 μL, 1.1 mmol) was added (exothermic). The reaction mixture was stirred at RT for 24 h, then heated at reflux for 16 h before diluting with EtOAc, washing with water, 10% KHSO₄, 1N NaOH, and brine, drying (MgSO₄) and concentration. Flash chromatography (silica, 20% then 40% EtOAc/hexane) provided 15-2 as a clear oil.

R_f 0.53 (silica, 50% EtOAc/hexane). ¹H NMR (300 MHz, CDCl₃) δ 8.0 (d, J=8 Hz, 2H), 7.50–7.30 (m, 7H), 5.18 (br m, 1H), 5.10 (s, 2H), 4.56 (s, 2H), 3.92 (s, 3H), 3.58 (br m, 2H), 3.45 (br m, 2H).

4-[2-(N-Cbz-amino)ethoxymethyl]benzoic acid (15-3)

Ester 15-2 (500 mg, 1.46 mmol) and 1N NaOH (3.6 mL, 3.6 mmol) were combined in 14 mL MeOH. After 3 h the mixture was concentrated, diluted with EtOAc, and extracted with H₂O. The aqueous layer was acidified with 10% KHSO₄ and extracted with EtOAc, and this organic layer was washed with brine, dried (MgSO₄), and concentrated, providing 15-3 as a white solid.

$R_f$ 0.62 (silica, 19:1:1 $CH_2Cl_2$/MeOH/HOAc). $^1$H NMR (300 MHz, $CD_3OD$) δ 8.0 (d, J=8 Hz, 2H), 7.5–7.3 (m, 7H), 5.07 (s, 2H), 4.59.(s, 2H), 3.56 (t, J=5 Hz, 2H), 3.34 (t, J=5 Hz, 2H).

4-[2-(N-Cbz-Amino)ethyloxymethyl]benzoyl-2(S)-phenylsulfonylamino-β-alanine t-butyl ester (15-4)

Acid 15-3 (300 mg, 0.91 mmol), amine 2-1 (325 mg, 0.91 mmol), EDC (209 mg, 1.09 mmol), HOBT (148 mg, 1.10 mmol), and NMM (300 μL, 2.7 mmol) were combined in 4.5 mL DMF. After 16 h the mixture was diluted with EtOAc, washed with water, 10% $KHSO_4$, sat $NaHCO_3$, and brine, dried ($MgSO_4$), and concentrated. Flash chromatography (silica, 70% EtOAc/hexane) provided 15-4 as an off-white solid.

$R_f$ 0.77 (silica, EtOAc). $^1$H NMR (400 MHz, $CDCl_3$) δ 7.79 (d, J=7 Hz, 2H), 7.72 (d, J=8 Hz, 2H), 7.40–7.20 (m, 10H), 7.0 (br s, 1H), 5.26 (br m, 1H), 5.09 (s, 2H), 4.49 (s, 2H), 3.80–3.70 (m, 2H), 3.5–3.45 (m, 3H), 3.41 (m, 2H), 1.24 (s, 9H).

4-(2-Aminoethyloxymethyl)benzoyl-2(S)-phenylsulfonylamino-β-alanine (15-5)

Cbz-ester 15-4 (200 mg, 0.33 mmol) was treated with 4 mL 30% HBr in HOAc for 2 h then concentrated and purified by flash chromatography (silica, 50:1:1 EtOH/$NH_4OH$/$H_2O$) providing 15-5 as a white solid.

$R_f$ 0.42 (silica, 20:1:1. EtOH/$NH_4OH$/$H_2O$). 1H NMR (400 MHz, $D_2O$) δ 7.66 (d, J=9 Hz, 2H) 7.52 (d, J=8 Hz, 2H), 7.38 (d, J=8 Hz, 2H), 7.33–7.25 (m, 3H), 7.58 (s, 2H), 3.80 (dd, J=10, 4 Hz, 1H), 3.66 (br t, J=5 Hz, 2H), 3.58 (dd, J=14, 4 Hz, 1H), 3.31 (dd, J=14, 10 Hz, 1H), 3.07 (br m, 2H).

4-[2-(Guanidino)ethyloxymethyl]benzoyl-2(S)-phenylsulfonylamino-β-alanine (15-6)

Amine 15-5 (40 mg, 0.095 mmol), PCA.HCl (15 mg, 0.10 mmol), and DIPEA (35 mL, 0.20 mmol) were combined in 1 mL DMF and heated at 50° for 16 h. Concentration, and flash chromatography (silica, 20:1:1 EtOH/$NH_4OH$/$H_2O$) provided 15-6 as a white solid.

$R_f$ 0.19 (silica, 20:1:1 EtOH/$NH_4OH$/$H_2O$). $^1$H NMR (400 MHz, $D_2O$) δ 7.61 (d,J=8 Hz, 2H), 7.46 (d, J=7 Hz, 2H), 7.31 (d, J=8 Hz, 2H), 7.28–7.18 (m, 3H), 4.51 (s, 2H), 3.75 (m, 1H), 3.56 (m, 2H), 3.54–3.44 (m, 2H), 3.25 (m, 2H).

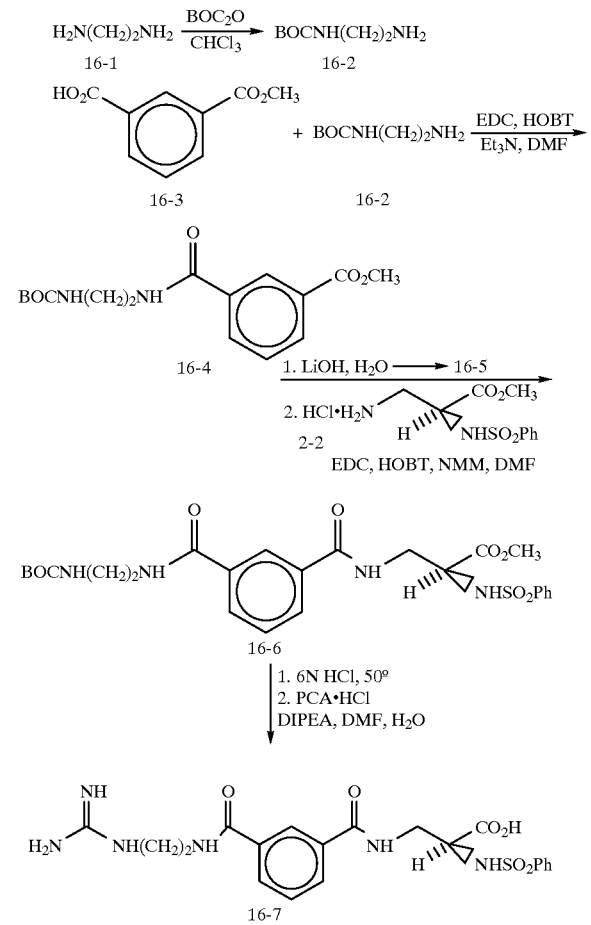

SCHEME 16

2-(N-BOC-Amino)ethylamine (16-2)

Ethylenediamine (16-1) (Aldrich) (18.04 g, 0.50 mol) in $CHCl_3$ (200 ml) was treated with a solution of $BOC_2O$ (13.1 g, 0.06 moles) in $CHCl_3$ (100 ml) at room temperature over 1 h. This was stirred for 16 h, filtered, and concentrated to give 16-2 as a clear oil.

Methyl 3-[2-(N-BOC-amino)ethylaminocarbonyl]benzoate (16-4)

A solution of methyl 3-carboxybenzoate (16-3) (Aldrich) (0.9 g, 5 mmol), 16-2 (0.8 g, 5 mmol), and HOBT (0.74 g, 5.5 mmol) in DMF (20 ml) was treated with Et₃N (1.0 g, 10 mmol) followed by EDC (1.15 g, 6.0 mmol). After stirring for 16 h the solvent was removed, the residue was taken up in H₂O (100 mL), and extracted with 3×75 ml portions of EtOAc. The organic extract was washed consecutively with 10% KHSO₄, brine, satd. NaHCO₃, brine, and dried (Na₂SO₄). Solvent removal gave a residue that was purified by flash chromatography (silica, 95% hexanes/EtOAc) to give crude 16-4. This was further purified by chromatography (silica, 70%/acetone/hexanes) to give pure 16-4.

R$_f$ 0.3 (silica, 70% hexanes/acetone). ¹H NMR (300 MHz, CDCl₃) δ 8.46 (s, 1H), 8.13-8.20 (dd, 1H), 8.03–8.10 (dd, 1H), 7.48–7.57 (t, 1H), 7.30–7.45 (m, IH), 4.95–5.08 (m, 1H), 3.95 (s, 3H), 3.52–3.62 (m, 2H), 3.38–3.48 (m, 2H), 1.42 (s, 9H).

3-[2-(N-BOC-Amino)ethylaminocarbonyl]benzoyl-2(S)-phenylsulfonyl-amino-β-alanine methyl ester (16-6)

16-4 (0.98 g, 3.03 mmoles) was dissolved in THF(1)/MeOH(1)/H₂O (1) (30 ml) and treated with LiOH (0.38 g, 9.1 mmoles). After 10 h, the solvent was removed, the residue acidified to pH 2–3 with 10% KHSO₄ solution, and extracted with EtOAc. The organic extract was dried (Na₂SO₄), concentrated, and the residue was purified by flash chromatography (silica, 95% hexanes/EtOAc) to give the desired acid 16-5.

This acid (0.46 g, 1.5 mmoles) was dissolved in DMF (20 ml) and treated with 2-2 (0.44 g, 1.5 mmoles), HOBT (0.22 g, .1.65 mmoles), NMM (0.45 g, 4.5 moles) followed by EDC (0.34 g, 1.8 mmoles). After stirring at room temperature for 16 h, the solvent was removed and the residue was taken up in H₂O (75 ml), and extracted with EtOAc. The organic extract was washed with 10% KHSO₄, brine, dried (Na₂SO₄) and concentrated to give 16-6 as a white solid.

¹H NMR (300 MHz, CDCl₃) δ 8.17 (s, H), 7.78–7.97 (dd, 4H), 7.20–7.65 (m, 6H), 6.40–6.65 (b, 1H), 5.00–5.55 (b, 1H), 4.13–4.24 (m, 1H 3.68–3.88 (m, 2H), 3.55 (s, 3H), 3.45–3.60 (bt, 2H), 3.30–3.44 (bt, 2H), 1.42 (s, 9H).

3-[2-(Guanidino)ethylaminocarbonyl]benzoyl-2(S)-phenylsulfonyl-amino-β-alanine (16-7)

A suspension of 16-6 in 6N HCl was stirred at room temperature while the ester gradually dissolved over 1 h. After 24 h the reaction was heated at 50° for 5 h, cooled and filtered. This solid was triturated with EtOAc and filtered to provide the desired acid.

This acid was treated with PCA.HCl as described for 1-8 to provide crude product. This was purified by flash chromatography on silica gel eluting with EtOH(10)/NH₄OH (0.5)/H₂O (0.5) to give 16-7.

¹H NMR (300 MHz, CD₃OD) δ 8.24 (s, 1H), 7.77–8.03 (m, 4H), 7.36–7.60 (m, 4H), 3.78–3.87 (dd, 1H), 3.50–3.72 (m, 4H), 3.32–3.47 (t, 2H).

SCHEME 17

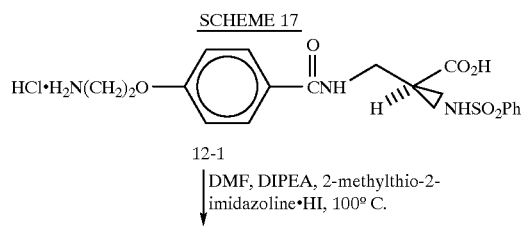

DMF, DIPEA, 2-methylthio-2-imidazoline•HI, 100° C.

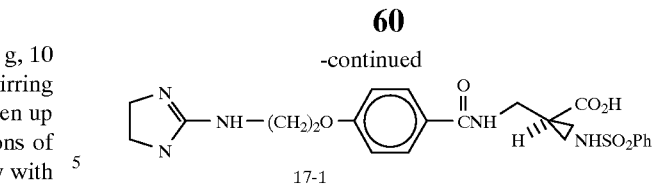

17-1

4-[2-(N-(2-Imidazolin-2-yl)amino)ethyloxy]benzoyl-2(S)-phenyl-sulfonylamino-β-alanine (17-1)

A solution of 12-1 (89 mg, 0.2 mmol), 2-methylthio-2-imidazoline.HI (98 mg, 0.4 mmol), DIPEA (139 μL, 0.8 mmol) and DMF was stirred at 100° C. for 20 h. Concentration of ffie cooled reaction mixture followed by chromatography (silica, 9:0.5:0.5 ethanol/NH₄OH/H₂O) gave 17-1 as a colorless lyophilozite.

TLC R$_f$ 0.21 (silica, 9:0.5:0.5 ethanol/NH₄OH/H₂O); ¹H NMR (400 MHz, CD₃D) δ 7.87 (m, 2H), 7.80 (d, J=9Hz, 2H), 7.50 (m, 3H), 6.98 (d, J=9 Hz, 2H), 4.17 (m, 2H), 3.80–3.50 (m, 5H), 3.73 (bs, 4H).

SCHEME 18

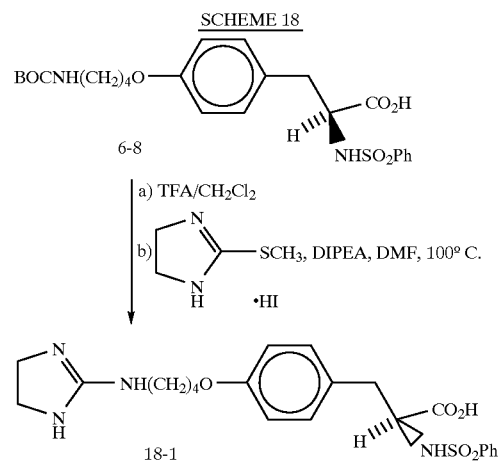

2(S)-Phenylsulfonylamino-3-[(4-(N-(imidazolin-2-yl)aminobutyloxy)-phenyl]propionic acid (18-1)

A solution of 6-8 (200 mg, 0.41 mmol), TFA (2 mL), and CH₂Cl₂ (2 mL) was stirred at ambient temperature for 1.0 h. The solution was concentrated and the residual TFA removed azeotropically with toluene. The resulting oil was dissolved in DMF (2 mL) and then treated with DIPEA (211 μL, 1.6 mmol) and 2-methylthio-2-imidazoline.HI (198 mg, 0.82 mmol). The resulting solution was heated at 100° C. for 20 h. Concentration of the cooled reaction mixture followed by flash chromatography (silica, 10:0.2:0.2→10:1:1 ethanol/NH₄OH/H₂O) gave 18-1 as a white solid.

TLC R$_f$ 0.38 (silica, 10:1:1 ethanol/NH₄OH/H₂O). ¹H NMR (400 MHz, D₂O) δ 7.45–7.20 (m, 5H), 6.83 (d, J=9 Hz, 2H), 6.56 (d, J=9 Hz, 2H), 3.87 (m, 3H), 3.48 (m, 4H), 3.09 (m, 2H), 2.90 (m, 1H), 3.57 (m, 1H), 1.60 (m, 4H).

SCHEME 19

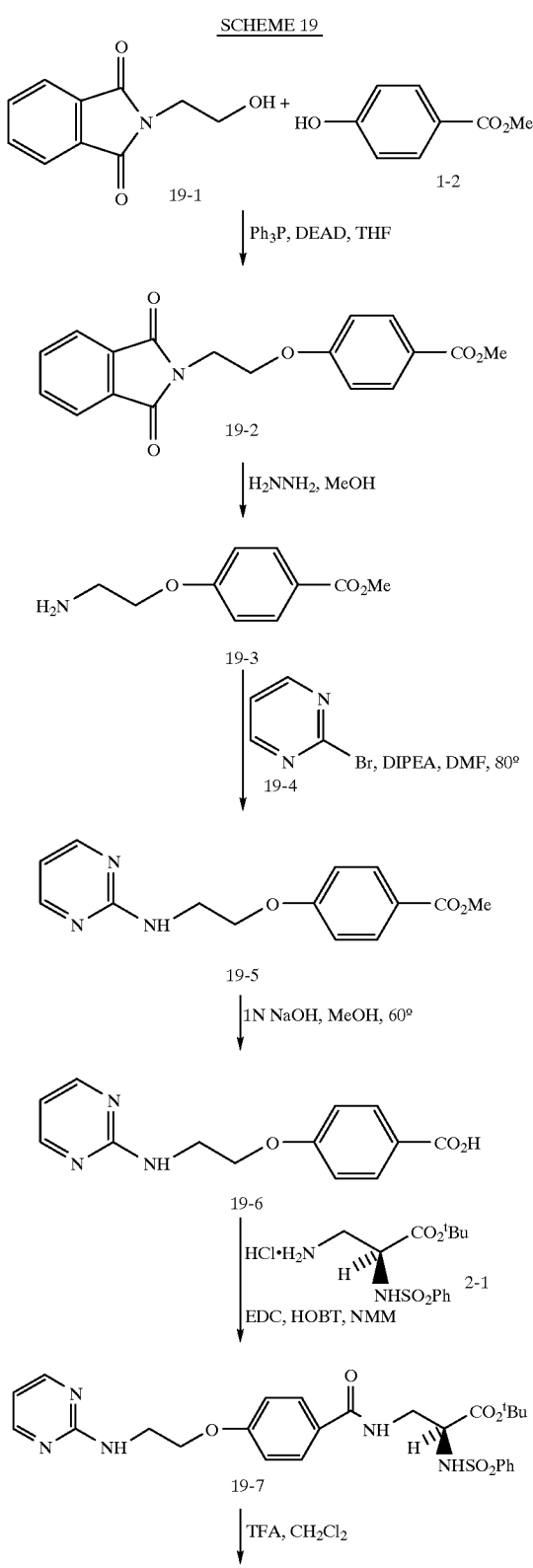

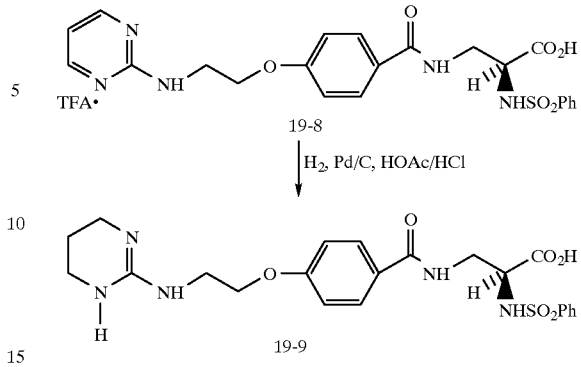

Methyl 4-(2-Phthalimidoethyloxy)benzoate (19-2)

A solution of N-(2-hydroxyethyl)phthalimide (Aldrich, 19-1, 6.36 g, 33 mmol) and DEAD (5.7 mL, 36 mmol) in 25 mL THF and 10 mL DMF was added to a solution of methyl 4-hydroxybenzoate (1-2, 5.00 g, 33 mmol) and Ph$_3$P (9.53 g, 36 mmol) in 100 mL THF during 1 h. After an additional hour the reaction was diluted with ether, washed twice with water, then 1N NaOH and brine, dried (MgSO$_4$), filtered and concentrated. Flash chromatography (silica gel, CH$_2$Cl$_2$) provided 19-2 as a white solid.

R$_f$ 0.18 (silica, CH$_2$Cl$_2$). $^1$H NMR (300 MHz, CDCl$_3$) δ 7.95 (d, J=9 Hz, 2H), 7.87 (m, 2H), 7.74 (m, 2H), 6.84 (d, J=9 Hz, 2H), 4.28 (t, J=6 Hz, 2H), 4.14 (t, J=6 Hz, 2H), 3.87 (s, 3H).

Methyl 4-(2-Aminoethyloxy)benzoate (19-3)

19-2 (1.59 g, 4.89 mmol) was suspended in 25 mL MeOH. Upon addition of hydrazine (2.0 mL, 64 mmol) the reaction became homogeneous. After 20 h a heavy precipitate had formed. The pH was adjusted to 1 by addition of 6N HCl, MeOH evaporated, and the solid suspended in 1N HCl. After filtering through Celite, the filtrate was washed with CH$_2$Cl$_2$, the pH was adjusted to 12 with 6N NaOH. The aqueous layer was extracted with fresh CH$_2$Cl$_2$. This organic phase was dried (Na$_2$SO$_4$) and concentrated providing 19-3 as a white solid.

R$_f$ 0.22 (silica, 9:1:1 CH$_2$Cl$_2$/MeOH/HOAc). $^1$H NMR (300 MHz, CDCl$_3$) δ 7.99 (d, J=9 Hz, 2H), 6.93 (d, J=9 Hz, 2H), 4.04 (t, J=5 Hz, 2H), 3.89 (s, 3H), 3.11 (t, J=5 Hz, 3H), 1.35 (br s, 2H).

Methyl 4-[2-(Pyrimidin-2-yl)amino)ethyloxy]benzoate (19-5)

Amine 19-3 (4.30 g, 22 mmol), 19-4 (3.51 g, 22 mmol) and DIPEA (3.8 mL, 22 mmol) were heated in 50 mL DMF at 80° for 16 h. The cooled mixture was concentrated, then diluted with EtOAc, washed with 1N NaOH and brine, dried (MgSO$_4$), and concentrated. Flash chromatography (silica, 10% acetone/CH$_2$Cl$_2$) provided white crystalline 19-5.

R$_f$ 0.42 (silica, 10% acetone/CH$_2$Cl$_2$). $^1$H NMR (300 MHz, CDCl$_3$) δ 8.29 (d, J=5 Hz, 2H), 7.99 (d, J=9 Hz, 2H), 6.93 (d, J=9 Hz, 2H), 6.57 (t, J=5 Hz, 1H), 5.53 (br m, 1H), 4.20 (t, J=5 Hz, 2H), 3.88 (s, 3H) 3.88 (overlapped t, 2H).

4-[2-(Pyrimidin-2-ylamino)ethyloxy]benzoic acid (19-6)

Pyrimidine ester 19-5 (3.31 g, 12.1 mmol) was combined with 1N NaOH (30 mL, 30 mmol) in 50 mL EtOH. After 2 h at 60° the mixture was cooled and 30 mL 1N HCl was added (final pH 5). The resulting white precipitate was collected on a frit, washed with water, and dried providing 19-6.

$R_f$ 0.67 (silica, 10:1:1 EtOH/NH$_4$OH/H$_2$O). $^1$H NMR (300 MHz, DMSO) δ 9.02 (d, J=5 Hz, 2H), 8.60 (d, J=9 Hz, 2H), 8.05 (t, J=6 Hz, 1H), 7.76 (d, J=9 Hz, 2H), 7.32 (t, J=5 Hz, 1H), 4.89 (t, J=6 Hz, 2H), 4.38 (q, J=6 Hz, 2H), 4.06 (s, 1H).

4-[2-(Pyrimidin-2-ylamino)ethyloxy]benzoyl-2(S)-phenylsulfonylamino-β-alanine tert-butyl ester (19-7)

Acid 19-6 (0.770 g, 2.97 mmol), amine 2-1 (1.0 g, 2.97 mmol), NMM (1.14 μL, 10.4 mmol) and HOBT (0.522 g, 3.86 mmol) were combined in 30 mL DMF, cooled to 0°, and EDC (0.740 g, 3.86 mmol) was added. The mixture was stirred at RT for 3 days, diluted with ethyl acetate, washed twice with water, sat. NaHCO$_3$, and brine, dried (MgSO$_4$), and concentrated. Flash chromatography (silica, 80% EtOAc/hexanes) provided 19-7 as a waxy solid.

$R_f$ 0.23 (silica, 80% EtOAc/hexane). $^1$H NMR (300 MHz, CDCl$_3$) δ 8.31 (d, J=5 Hz, 2H), 7.85 (d, J=7 Hz, 2H), 7.73 (d, J=9 Hz, 2H), 7.60–7.45 (m, 3H), 6.90 (d, J=9 Hz, 2H), 6.67 (br m, 1H), 6.57 (t, J=5 Hz, 1H), 5.94 (d, J=8 Hz, 1H), 5.68 (br m, 1H), 4.17 (t, J=5 Hz, 2H), 4.00–3.83 (m, 4H), 3.59 (m, 1H), 1.28 (s, 9H).

4-[2-(Pyrimidin-2-ylamino)ethyloxy]benzoyl-2(S)-phenylsulfonylamino-β-alanine trifluoroacetate (19-8)

Ester 19-7 (1.05 g, 1.86 mmol) and anisole (0.40 mL, 3.7 mmol) were dissolved in CH$_2$Cl$_2$ (9 mL), cooled to 0°, and TFA (9 mL) was added. After 2 h at 0° and 16 h at 20°, the reaction was concentrated, azeotroped with toluene, and triturated with Et$_2$O providing 19-8 as a white solid.

$R_f$ 0.30 (silica, 22:20:1:1 EtOAc/EtOH/NH$_4$OH/H$_2$O). $^1$H NMR (400 MHz, CD$_3$OD) 8.45 (br, 2H), 7.82 (dt, J=7, 2 Hz, 2H), 7.72 (d, J=9 Hz, 2H), 7.50 (tm, J=7 Hz, 1H), 7.42 (tm, J=8 Hz, 2H), 6.99 (d, J=9 Hz, 2H), 6.82 (t, J=5 Hz, 1H), 4.25 (t, J=5 Hz, 2H), 4.18 (dd, J=9, 5 Hz, 1H), 3.88 (t, J=5 Hz, 2H), 3.71 (dd, J=14, 5 Hz, 1H), 3.48 (m, 1H).

4-[2-(3,4,5,6-Tetrahydropyrimidin-2-ylamino)ethyloxy]benzoyl-2(S)-phenylsulfonylamino-β-alanine (19-9)

Pyrimidine 19-8 (1.05 g, 1.75 mmol) was dissolved in a mixture of acetic acid (50 mL) and conc HCl (4.5 mL). After addition of 10% Pd/C (450 mg) the mixture was shaken on a Parr hydrogenator under 45 psi H$_2$ pressure for 2 h. The reaction mixture was filtered, concentrated, azeotroped with toluene, and purified by flash chromatography (silica 20:1:1 then 8:1:1 EtOH/NH$_4$OH/H$_2$O) providing 19-9 as a white solid.

$R_f$ 0.35 (8:1:1, EtOH/NH$_4$OH/H$_2$O). $^1$H NMR (300 MHz, CD$_{3\text{O}}$D+DCl) δ 7.84 (d m, J=7 Hz, 2H), 7.74 (d, J=9 Hz, 2H), 7.50–7.40 (m, 3H), 7.02 (d, J=9 Hz, 2H), 4.22–4.17 (m, 3H), 3.72 (dd, J=14, 5 Hz, 1H), 3.60 (t, J=5 Hz, 2H), 3.49 (dd, J=14, 9 Hz, 1H), 3.38 (t, J=5 Hz, 4H), 1.95 (qn, J=6 Hz, 2H).

SCHEME 20

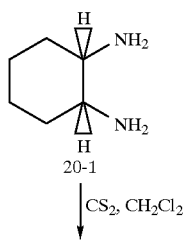

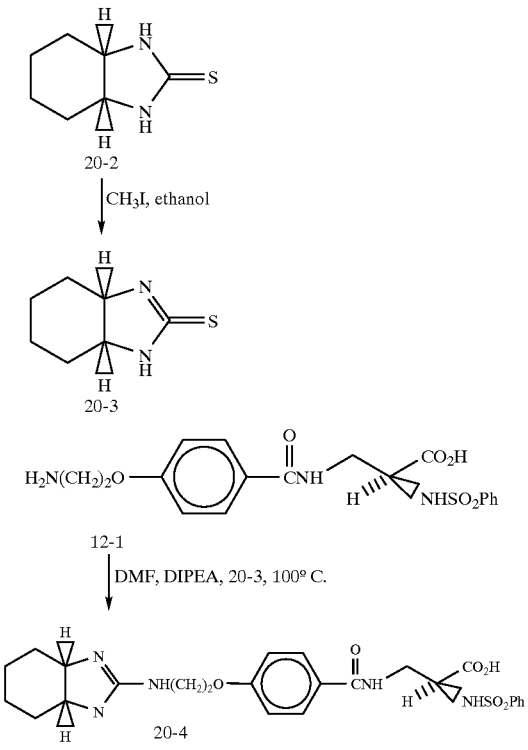

Cis-3a,4,5,6,7,7a-Hexahydro-1H-benzimidazol-2-thione (20-2)

A solution of carbon disulfide (1.1 mL, 17.9 mmol) and CH$_2$Cl$_2$ (10 mL) was treated dropwise with cis-1,2-diaminocyclohexane 20-1 (Aldrich) (2.0 g, 17.5 mmol) while maintaining the reaction mixture temperature below 20° C. with an ice bath. The reaction mixture was stirred at ambient temperature for 2.0 h after the addition was complete. Concentration followed by refluxing the resulting solid in H$_2$O (20 mL) for 20 h gave a yellow solution. The cooled solution was extracted with CH$_2$Cl$_2$ and the CH$_2$Cl$_2$ portion was dried (MgSO$_4$) and concentrated. The pale yellow solid was recrystallized from CH$_2$Cl$_2$/ether to give 20-2 as a pale yellow solid. mp=164–166° C.

$^1$H NMR (300 MHz, CDCl$_3$) δ 6.30 (bs, 2H), 3.90 (m, 2H), 1.80–1.30 (m, 8H).

2-[Cis-3a,4,5,6,7,7a-Hexahydro-1H-benzimidazol-2-yl] methylsulfide (20-3)

A suspension of 20-2 (1.3 g, 8.3 mmol) in ethanol (5 mL) at ambient temperature was treated with iodomethane (0.8 mL, 12.5 mmol). After 20 h the ethanol was evaporated and the resulting solid triturated with acetone to give 20-3 as a solid.

$^1$H NMR (300 MHz, CD$_3$OD) δ 4.22 (m, 2H), 2.67 (s, 3H), 2.00–1.40 (m, 8H).

4-[2-[N-[Cis-3a,4,5,6,7,7a-Hexahydro-1H-benzimidazol-2-yl]amino]-ethyloxy]benzoyl-2(S)-phenylsulfonylamino-β-alanine (20-4)

A solution of 20-3 (298 mg, 1.0 mmol), 12-1 (222 mg, 0.5 mmol), DIPEA (261 μL, 1.5 mmol), H$_2$O (6 drops) and DMF (6 mL) was heated at 100° C. for 24 h. The cooled solution was concentrated at 50° C. and the residue chromatographed (silica, 9:0.5:0.5 ethanol/H$_2$O/NH$_4$OH) to give 20-4 as a colorless solid after lyophilization.

TLC $R_f$=0.16 (silica, 9:0.5:0.5 ethanol/NH$_4$OH/H$_2$O); $^1$H NMR (300 MHz, CD$_3$OD) δ 7.83 (m, 2H), 7.77 (d, J=9 Hz, 2H), 7.48 (m, 3H), 7.01 (d, J=9 Hz, 2H), 4.19 (m, 3H), 3.91 (bs, 2H), 3.75–3.40 (m, 4H), 1.90–1.35 (m, 8H).

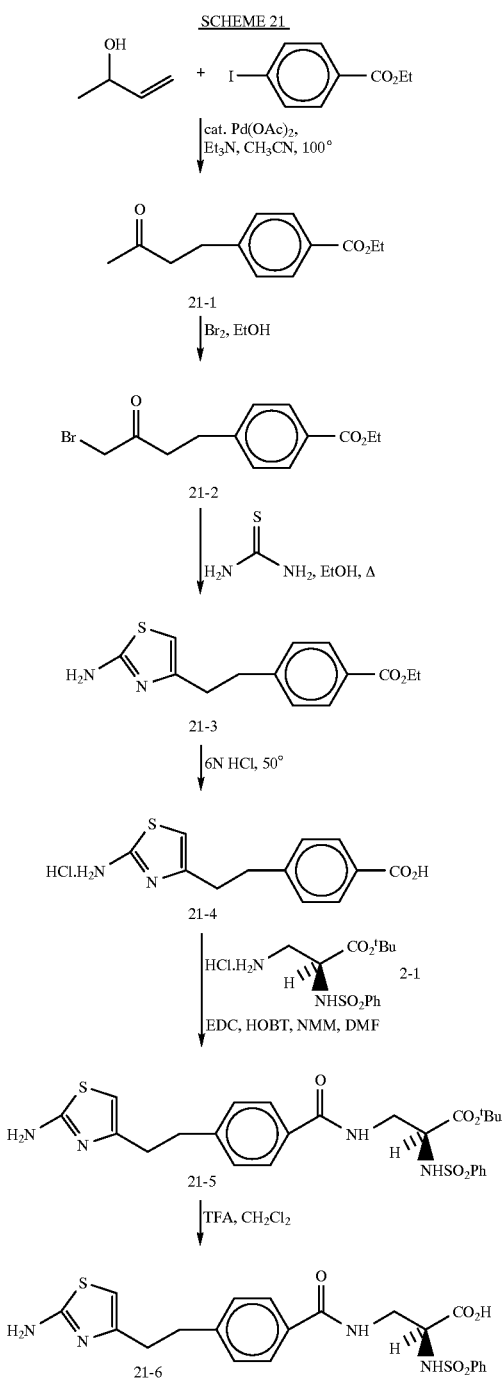

SCHEME 21

5 Ethyl 4-(3-oxobut-1-yl)benzoate (21-1)

3-Hydroxy-1-butene (Aldrich) (2.15 mL, 25 mmol), ethyl 4-iodobenzoate (5.52 g, 20 mmol), Et$_3$N (3.5 mL, 25 mmol) and Pd(OAc)2 (19 mg, 0.08 mmol) were combined in 6 mL CH$_3$CN, sealed in a glass pressure tube and heated at 100° for 3 h. The mixture was cooled, diluted with Et$_2$O, washed with water, 1N NaOH, 5% KHSO$_4$, and brine, dried (MgSO$_4$), and concentrated. Flash chromatography (silica, 10% EtOAc/hexanes) provided 21-1 as a white crystalline solid.

R$_f$ 0.41 (silica, 30% EtOAc/hexane). $^1$H NMR (300 MHz, CDCl$_3$) δ 7.96 (d, J=8 Hz, 2H), 7.25 (d, J=8 Hz, 2H), 4.36 (q, J=7 Hz, 2H), 2.95 (t, J=7 Hz, 2H), 2.78 (t, J=7 Hz, 2H), 2.15 (s, 3H), 1.38 (t, J=7 Hz, 3H).

Ethyl 4-(4-bromo-3-oxobut-1-yl)benzoate (21-2)

21-1 (3.13 g, 14.2 mmol) was dissolved in EtOH (30 mL) at 0°, and Br$_2$ (805 μL, 15.6 mmol) was added. After warming to RT for 16 h the reaction was concentrated, diluted with Et2O, washed with water and brine, dried (MgSO$_4$), and concentrated. Flash chromatography (silica, 10% EtOAc/hexane) provided 21-2 as a white solid.

R$_f$ 0.67 (silica, 30% EtOAc/hexane). $^1$H NMR (400 MHz, CDCl$_3$) δ 7.97 (d, J=8 Hz, 2H), 7.26 (d, J=8 Hz, 2H), 4.36.(q, J=7 Hz, 2H), 3.85 (s, 2H), 3.00 (s, 4H), 1.38 (t, J=7 Hz, 3H).

Ethyl 4-[2-(2-aminothiazol-4-yl)ethyl]benzoate (21-3)

Thiourea (374 mg, 4.9 mmol) and 21-2 (1.4 g, 4.7 mmol) were combined in 24 mL EtOH and heated to reflux for 1 h. Concentration and flash chromatography (silica, 80% EtOAc/hexane then 10% MeOH/EtOAc) provided 21-3 as a white solid.

R$_f$ 0.54 (silica, EtOAc). $^1$H NMR (300 MHz, DMSO) δ 7.86 (d, J=8 Hz, 2H), 7.35 (d, J=8 Hz, 2H), 6.18 (s, 1H), 4.29 (q, J=7 Hz, 2H), 3.4 (br s), 2.95 (t, J=7 Hz, 2H), 2.73 (t, J=8 Hz, 2H), 1.31 (t, J=7 Hz, 3H).

4-[2-(2-Aminothiazol-4-yl)ethyl)benzoic acid hydrochloride (21-4)

Ester 21-3 (1.5 g, 5.43 mmol) was treated with 6N HCl for 16 h at RT then 16 h at 50°. Concentration provided 21-4 as an off-white solid.

R$_f$ 0.74 (silica, 9:1:1 CH$_2$Cl$_2$/MeOH/HOAc). $^1$H NMR (300 MHz, DMSO) δ 9.45 (br s), 8.10 (d, J=8 Hz, 2H), 7.58 (d, J=8 Hz, 2H), 6.71 (s, 1H), 3.90 (br s), 3.20 (t, J=7 Hz, 2H), 3.07 (t, J=7 Hz, 2H).

4-[2-(2-Aminothiazol-4-yl)ethyl]benzoyl-2(S)-phenylsulfonylamino-β-alanine tert-butyl ester (21-5)

21-4 (150 mg, 0.53 mmol), amine hydrochloride 2-1 (0.53 mmol, 177 mg). HOBT (86 mg, 0.64 mmol), NMM (204 μL, 1.9 mmol), and EDC (122 mg, 0.64 mmol) were combined in 2.6 mL DMF at −15°, warmed to RT and stirred for 16 h. The reaction was diluted with EtOAc, washed with water, saturated NaHCO$_3$ and brine, dried (MgSO$_4$), and concentrated. Flash chromatography (silica, 70% EtOAc/hexane) provided 21-5 as a clear oil.

R$_f$ 0.48 (silica, EtOAc). $^1$H NMR (300 MHz, CDCl$_3$) δ 7.86 (d, J=8 Hz, 2H), 7.69 (d, J=8 Hz, 2H), 7.60–7.45 (m, 3H), 7.24 (d, J=8 Hz, 2H), 6.70 (br m, 1H), 6.05 (s, 1H), 5.90 (br m, 1H), 4.92 (br s, 2H), 3.85–4.00 (m, 2H), 3.62 (m, 1H), 2.99 (t, J=8 Hz, 2H); 2.88 (t, J=8 Hz, 2H), 1.29 (s, 9H).

4-[2-(2-Aminothiazol-4-yl)ethyl]benzoyl-2(S)-phenylsulfonylamino-β-alanine (21-6)

Ester 21-5 (200 mg, 0.377 mmol) was dissolved in 2 mL CH$_2$Cl$_2$, and 2 ml TFA was added. After 4 h at RT the mixture was concentrated, azeotroped with toluene, and purified by flash chromatography (silica, 28:10:1:1 EtOAc/EtOH/NH$_4$OH/H$_2$O) providing 21-6 as a white solid.

R$_f$ 0.39 (silica, 12:10:1:1 EtOAc/EtOH/NH$_4$OH/H$_2$O). $^1$H NMR (400 MHz, DMSO) δ 8.6 (br s), 7.77 (d, J=8 Hz, 2H), 7.65 (d, J=8 Hz, 2H), 7.58 (t, J=7 Hz, 1H), 7.51 (t, J=7 Hz, 2H), 7.27 (d, J=8 Hz, 2H), 6.84 (m, 1H), 6.11 (s, 1H), 3.50–3.40 (m, 2H), 3.32 (br s), 2.92 (t, J=8 Hz, 2H), 2.70 (t, J=8 Hz, 2H).

SCHEME 22

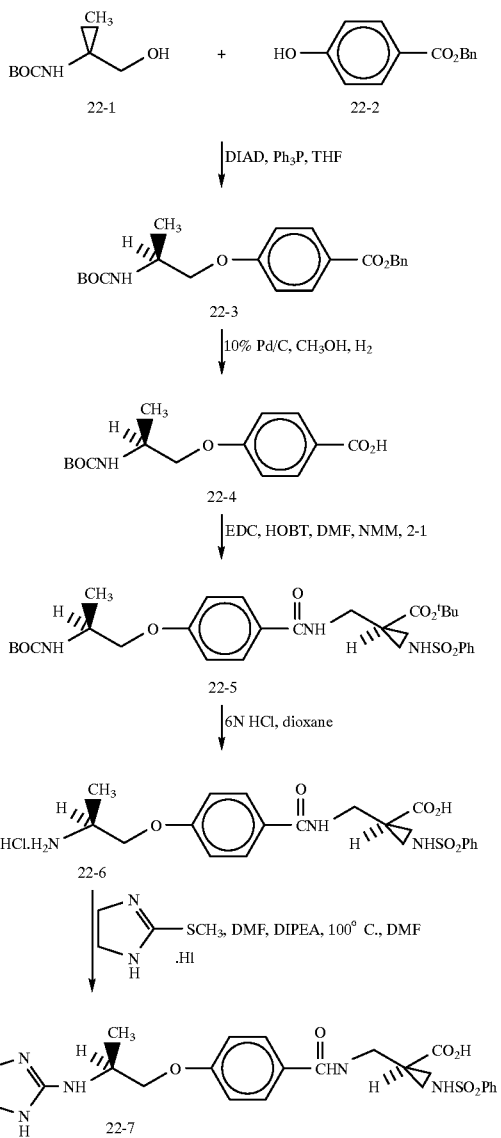

Benzyl 4-[2(S)-(N-BOC-amino)propyloxy]benzoate (22-3)

A THF (25 mL) solution of DIAD (2.9 mL, 14.8 mmol) and 22-1 (Fluka) (2.0 g, 11.4 mmol) was added dropwise to a stirred solution of THF (50 mL), 22-2 (Fluka) (2.6 g, 11.4 mmol) and Ph₃P (3.9 g, 14.8 mmol) over a 2 h period, followed by heating for 20 h at 70° C. The cooled reaction mixture was concentrated and purified by flash chromatography (silica, 20% EtOAc/hexanes) to give 22-3 as a colorless oil.

TLC $R_f$ 0.36 (silica, 5% acetone/$CH_2Cl_2$); $^1$H NMR (300 MHz, $CDCl_3$) δ 8.02 (d, J=9 Hz, 2H), 7.70–7.30 (m, 5H), 6.92 (d, J=9 Hz, 2H), 6.45 (m, 1H), 5.33 (s, 2H), 4.75 (m, 1H), 4.06 (m, 1H), 3.96 (m, 2H), 1.45 (s, 9H), 1.26 (d, 3H).

4-[2(S)-(N-BOC-Amino)propyloxy]benzoic acid (22-4)

A mixture of 22-3 (1.6 g, 4.3 mmol), 10% Pd/C (0.33 g) and ethanol (25 mL) was stirred under a hydrogen atmosphere (1 atm) for 20 h. Filtration through a celite pad followed by concentration of the filtrate gave 22-4 as a colorless solid.

$^1$H NMR (300 MHz, $CDCl_3$) δ 8.05 (d, J=9 Hz, 2H), 6.96 (d, J=9 Hz, 2H), 4.77 (m, 1H), 4.09 (m, 1H), 3.99 (m, 2H), 1.46 (s, 9H), 1.31 (d, J=7 Hz, 3H).

4-[2(S)-(N-BOC-Amino)propyloxy]benzoyl-2(S)-phenylsulfonylamino-β-alanine tert-butyl ester (22-5)

Following the procedure for coupling 19-6 to 2-1, 22-4 (295 mg, 1.0 mmol) was coupled to 2-1 (336 mg, 1.0 mmol) to give 22-5 as a beige solid.

TLC $R_f$ 0.28 (silica, 10% acetone/$CH_2Cl_2$); $^1$H NMR (300 MHz, CDCl3) δ 7.87 (m, 2H), 7.77 (d, J=9 Hz, 2H), 7.53 (m, 3H), 6.93 (d, J=9 Hz, 2H), 6.64 (m, 1H), 5.69 (m, 1H), 4.06 (m, 1H), 3.90 (m, 4H), 3.56 (m, 1H), 1.46 (s, 9H), 1.28 (s, 9H). 4-[2(S)-Aminopropyloxy]benzoyl-2(S)-phenylsulfonylamino-β-alanine HCl (22-6)

22-5 (545 mg, 0.94 mmol) in 6N HCl (25 mL) and dioxane (25 mL) was stirred overnight at ambient temperature. Concentration followed by trituration with ether gave 22-6 as a colorless solid.

TLC $R_f$ 0.62 (silica, 95% ethanol/$NH_4OH$); $^1$H NMR (300 MHz, $CD_3OD$) δ 7.83 (m, 2H), 7.79 (d, J=9 Hz, 2H), 7.48 (m, 3H), 7.08 (d, J=9 Hz, 2H), 4.3–3.3 (m, 6H), 1.43 (d, J=7 Hz, 3H).

4-[2(S)-(N-(2-Imidazolin-2-yl)amino)propyloxy]benzoyl-2(S)-phenyl-sulfonylamino-β-alanine trifluoroacetate (22-7)

A mixture of 22-6 (256 mg, 0.51 mmol), DIPEA (292 μL, 1.7 mmol), (2-methylthio-2-imidazoline.HI) (273 mg, 1.1 mmol) and DMF (2 mL) was heated at 100° C. for 24 h. Concentration followed by flash chromatography (silica, 9:1:1:1 ethanol/$NH_4OH/H_2O$) gave a beige solid. This solid was purified on an HPLC semiprep (C18 column, 95:5 to 5:95 $H_2O$ (0.1% TFA)/$CH_3CN$ gradient) followed by lyophilization to give 22-7 as a colorless solid.

TLC $R_f$ 0.33 (silica, 9:0.5:0.5 ethanol/$H_2O/NH_4OH$); $^1$H NMR (300 MHz, $CD_3OD$) δ 7.83 (m, 2H), 7.76 (d, J=(9 Hz, 2H), 7.47 (m, 3H), 7.00 (d, J=9 Hz, 2H), 4.20–3.40 (m, 6H), 3.73 (m, 4H), 1.37 (d, J=7 Hz, 3H).

SCHEME 23

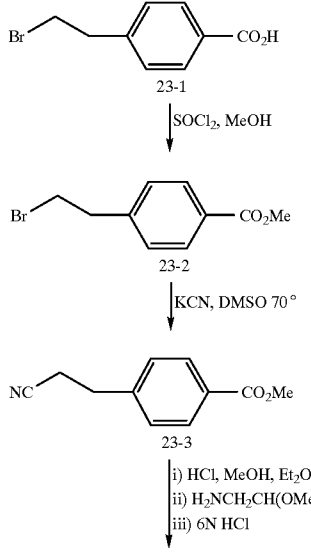

4-[2-(Imidazol-2-yl)ethyl]benzoic acid hydrochloride (23-5)

Ester 23-4 (450 mg; 1.77 mmol) was dissolved in 6N HCl and stirred for 16 h. Concentration provided 23-5 as dark oil. $R_f$ 0.28 (silica, 4:1:1 $CH_2Cl_2$/MeOH/HOAc).

$^1$H-NMR (400 MHz, DMSO) δ 7.84 (d, J=8 Hz, 2H), 7.51 (s, 2H), 7.32 (d, J=7 Hz, 2H), 3.27 (t, J=7 Hz, 2H), 3.19 (t, J=7, 2H).

4-[2-(Imidazol-2-yl)ethyl]benzoyl-2(S)-phenylsulfonylamino-β-alanine tert-butyl ester acetate (23-6)

Acid 23-5 (ca 2 mmol), amine 2-1 (700 mg, 2.0 mmol), HOBT (324 mg, 2.4 mmol), and NMM (0.77 mL, 7.0 mmol) were combined in 10 mL DMF at −15°, then EDC (364 mg, 1.9 mmol) was added The mixture was warmed to RT, stirred overnight, then concentrated. Flash chromatography (silica, 4:1:1 $CH_2Cl_2$/MeOH/HOAc) provided 23-6, $R_f$ 0.22 (silica, 4:1:1 $CH_2Cl_2$:MeOH:HOAc).

4-[2-(Imidazol-2-yl)ethyl]benzoyl-2(S)-phenylsulfonylamino-β-alanine trifluoroacetate (23-7)

Ester 23-6 (100 mg, 0.2 mmol) was dissolved in 5 mL $CH_2Cl_2$, and 5 mL TFA was added. After 1 h the reaction was concentrated and azeotroped with toluene. Flash chromatography (silica, 50:1:1 EtOH/$NH_4OH$/$H_2O$) and preparative HPLC ($C_{18}$, 0.1% TFA $H_2O$/$CH_3CN$) provided 23-7.

$^1$H-NMR (400 MHz, D20) δ 7.65 (d, J=7 Hz, 2H), 7.39 (d, J=8 Hz, 2H), 7.28–7.20 (m, 3H), 7.15 (s, 2H), 7.11 (d, J=9 Hz, 2H), 3.91 (dd, J=10, 4 Hz, 1H), 3.60 (dd, J=14, 4 Hz, 1H), 3.32 (dd, J=14, 10 Hz, 1H), 3.23 (t, J=7 Hz, 2H), 3.06 (t, J=7 Hz, 2H).

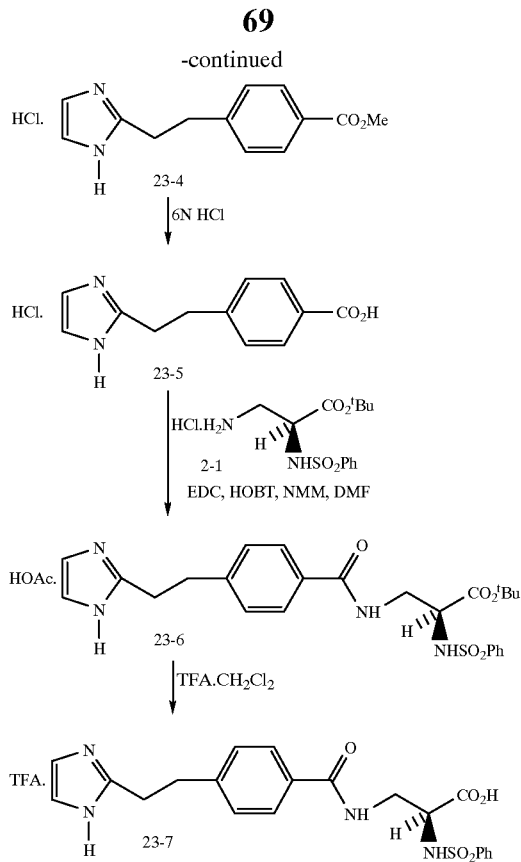

Methyl 4-(2-bromoethyl)benzoate (23-2)

23-1 (1.95 g, 8.60 mmol) (Aldrich) was suspended in 50 mL MeOH and $SOCl_2$ (5.0 mL, 69 mmol) was added dropwise. Following an exothermic reaction, the mixture was stirred at RT for 16 h, concentrated, and purified by flash filtration (silica, 5% EtOAc/hexanes) providing 23-2 as a colorless oil. $R_f$ 0.37 (silica, 10% EtOAc/hexanes).

$^1$H-NMR (300 MHz, $CDCl_3$) δ 8.00 (d, J=8 Hz, 2H), 7.29 (d, J=8 Hz, 2H), 3.91 (s, 3H), 3.59 (t, J=7 Hz, 2H), 3.22 (d, J=7 Hz, 2H).

Methyl 4-(2-cyanoethyl)benzoate (23-3)

Bromide 23-2 (0.52 g, 2.14 mmol) and KCN (167 mg, 2.57 mmol) were combined in 10 mL DMSO. After 20 h, at RT and 1.5 h at 70° the reaction mixture was diluted with EtOAc, washed with water, sat. $NaHCO_3$, 10% $KHSO_4$ and brine, dried ($MgSO_4$), and concentrated providing 23-3 as a yellow solid. $R_f$ 0.23 (30% EtOAc/hexanes).

$^1$H-NMR (300 MHz, $CDCl_3$) δ 8.02 (d, J=8 Hz, 2H), 7.32 (d, J=9 Hz, 2H), 3.92 (s, 3H), 3.02 (t, J=7 Hz, 2H), 2.66 (t, J=7 Hz, 2H).

Methyl 4-[2-(imidazol-2-yl)ethyl]benzoate hydrochloride (23-4)

Nitrile 23-3 (400 mg, 2.11 mmol) was dissolved in 10 mL $Et_2O$ at 0° MeOH (289 μL, 4.2 mmol) was added, the mixture was saturated with anhydrous HCl. Once the white ppt. formed, the solvent was evaporated and replaced with MeOH (5 mL), cooled to 0°, and aminoacetaldehyde dimethylacetal (250 μL, 2.3 mmol) was added. The reaction was heated to reflux for 3 days then concentrated, diluted in 10 mL 6N HCl and concentrated again providing 23-4 as a solid.

$R_f$ 0.16 (silica, 4:1:1 $CH_2Cl_2$/MeOH/HOAc). $^1$H-NMR (400 MHz, $D_2O$) δ 7.59 (d J=7 Hz, 2H), 7.04 (d, J=7 Hz, 2H), 6.77 (m, 2H), 3.74 (bs, 2H), 289 (br s, 5H).

SCHEME 24

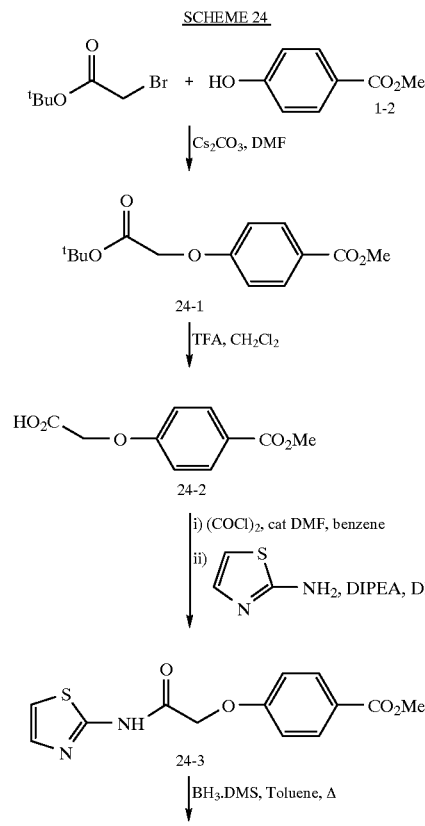

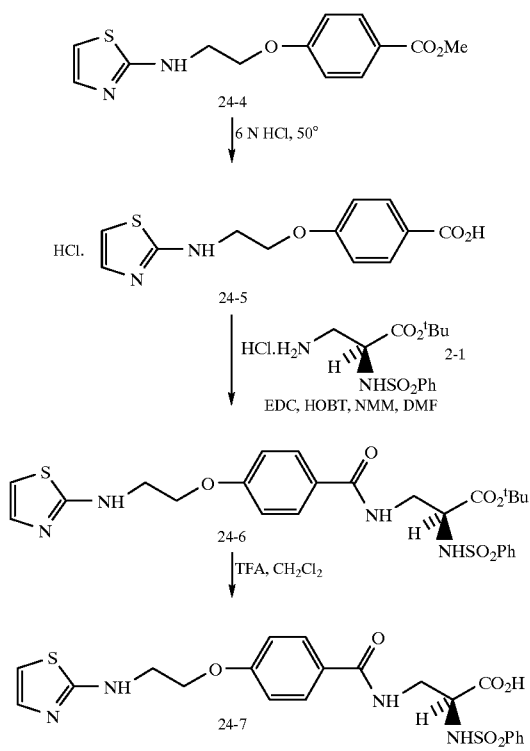

Methyl 4-(t-butyloxyacetyloxy)benzoate (24-1)

t-Butyl bromoacetate (0.83 mL, 5.1 mmol), methyl 4-hydroxybenzoate (780 mg, 5.1 mmol) and $Cs_2CO_3$ (1.83 g, 5.6 mmol) were combined in 25 mL DMF. After 16 h, the reaction was diluted with ethyl acetate, washed with water, saturated $NaHCO_3$, 10% $KHSO_4$ and brine, dried ($MgSO_4$) and concentrated providing 24-1 as a yellow oil. $R_f$ 0.84 (silica, 50% EtOAC/hexane).

$^1$H-NMR (300 MHz, $CDCl_3$) δ 7.96 (d, J=8 Hz, 2H), 6.88 (d, J=8 Hz, 2H), 4.55 (s, 2H), 3.86 (s, 3H), 1.46 (s, 9H).

Methyl 4-(carboxymethyloxy)benzoate (24-2)

Ester 24-1 was dissolved in 15 mL $CH_2Cl_2$, then 15 mL TFA was added. After 2 h, the mixture was concentrated providing 24-2 as a white solid.

$^1$H-NMR (300 MHz, DMSO) δ 7.91 (d, J=9 Hz, 2H), 7.03 (d, J=9 Hz, 2H), 4.79 (s, 2H), 3.82 (s, 3H).

Methyl 4-[(thiazol-2-ylamino)acetyloxy]benzoate (24-3)

Acid 24-2 (1.0 g, 5 mmol) was suspended in 25 mL benzene, a few drops of DMF were added, then oxalyl chloride (1.3 ml, 15 mmol) in two portions. Once the gas evolution stopped, the homogeneous solution was concentrated, diluted with 25 mL DMF, and treated with 2-aminothiazole (550 mg, 5.5 mmol) and DIPEA (1 mL, 5.7 mmol). This mixture was stirred for 16 h, diluted with EtOAc, washed with water, sat. $NaHCO_3$, and brine, dried ($MgSO_4$) and concentrated providing 24-3 as an orange solid.

$^1$H-NMR (400 MHz, $CDCl_3$) δ 8.06 (d, J=9 Hz, 2H), 7.50 (d, J=4 Hz, 1H), 7.05 (d, J=4 Hz, 1H), 7.00 (d, J=9 Hz), 4.80 (s, 2H), 3.91 (s, 3H).

Methyl 4-[2-(thiazol-2-ylamino)ethyloxy]benzoate (24-4)

Amide 24-3 (1.0 g, 3.4 mmol) was dissolved in 7 mL toluene at 0°, and $BH_3$.DMS (341 μL, 3.6 mmol) was added. After 15 min, the reaction was heated to reflux for 16 h, cooled to 0°, and quenched with 10% $Na_2CO_3$. The mixture was extracted with EtOAc, the organic phase was washed with water and brine, dried ($MgSO_4$), concentrated, and purified by flash chromatography (silica, 70% EtOAc/hexane) providing 24-4 as a white solid. $R_f$ 0.64 (silica, EtOAc).

$^1$H-NMR (400 MHz, $CDCl_3$) δ 7.99 (d, J=9 Hz, 2H), 7.14 (d, J=4 Hz, 1H), 6.92 (d, J=9 Hz, 2H), 6.53 (d, J=4 Hz, 1H), 4.24 (t, J=5 Hz, 2H), 3.89 (s, 3H), 3.79 (q, J=5 Hz, 2H).

4-[2-(Thiazol-2-ylamino)ethyloxy]benzoic acid hydrochloride (24-5)

Ester 24-4 (180 mg, 0.65 mmol) was heated at 50° in 6 mL 6N HCl for 16 h, then concentrated providing 24-5 as as yellow solid.

$R_f$ 0.68 (silica, 9:1:1 $CH_2Cl_2$/MeOH/HOAc). $^1$H-NMR (300 MHz, $CD_3OD$) δ 7.96 (d, J=9 Hz, 2H), 7.30 (d, J=4 Hz, 1H), 7.00 (d, J=9 Hz, 2H), 6.97 (d, J=4 Hz, 1H), 4.34 (t, J=5 Hz, 2H), 3.89 (t, J=5 Hz, 2H).

4-[2-(Thiazol-2-ylamino)ethyloxy]benzoyl-2(S)-phenylsulfonylamino-β-alanine tert-butyl ester (24-6)

Acid 24-5 (160 mg, 0.60 mmol), amine 2-1 (215 mg, 0.60 mmol), EDC (140 mg, 0.73 mmol), HOBT (98 mg, 0.73 mmol), and NMM (235 μL, 2.1 mmol) were combined in 3 miL DMF at −15°. After stirring at RT for 16 h, the reaction was diluted with EtOAc, washed with water, sat. $NaHCO_3$ and brine, dried, concentrated, and purified by flash chromatography (silica, 70% EtOAc/hexane) providing 24-6 as an off-white solid. $R_f$ 0.54 (silica, EtOAc).

$^1$H-NMR (400 MHz, CDCl3) δ 7.86 (d, J=8 Hz, 2H), 7.76 (d, J=9 Hz, 2H), 7.57 (t, J=8 Hz, 1H), 7.50 (t, J=8 Hz, 2H), 7.14 (d, J=4 Hz, 1H), 6.92 (d, J=9 Hz, 2H), 6.70 (br m, 1H), 6.53 (d, J=4 Hz, 1H), 4.21 (t, J=5 Hz, 2H), 3.95–3.85 (m, 2H), 3.77 (t, J=5Hz, 2H), 3.58 (m, 1H), 1.28 (s, 9H).

4-[2-(Thiazol-2-ylamino)ethyloxy]benzoyl-2(S)-phenylsulfonylamino-β-alanine (24-7)

Ester 24-6 (197 mg, 0.36 mmol) was dissolved in 1.8 mL $CH_2Cl_2$ and treated with 1.8 mL TFA. Once the starting material had disappeared, the reaction was concentrated, and flash chromatography (silica, 18:10:1:1 EtOAc/EtOH/$NH_4OH$/$H_2O$) provided 24-7 as a white solid. $R_f$ 0.26 (silica, 18:10:1:1 EtOAc/EtOH/$NH_4OH$/$H_2O$).

$^1$H-NMR (400 MHz, D20) δ 7.52 (dd, J=8, 2 Hz, 2H), 7.41 (d, J=9 Hz, 2H), 7.10–7.04 (m, 3H), 6.93 (d, J=4 Hz, 1H), 6.89 (d, J=9 Hz, 2H), 6.53 (d, J=4 Hz, 1H), 4.21 (t, J=5 Hz, 2H), 3.60 (t, J=5 Hz, 2H), 3.55–3.44 (m, 2H), 3.06 (dd, J=13, 9 Hz, 1H).

SCHEME 25
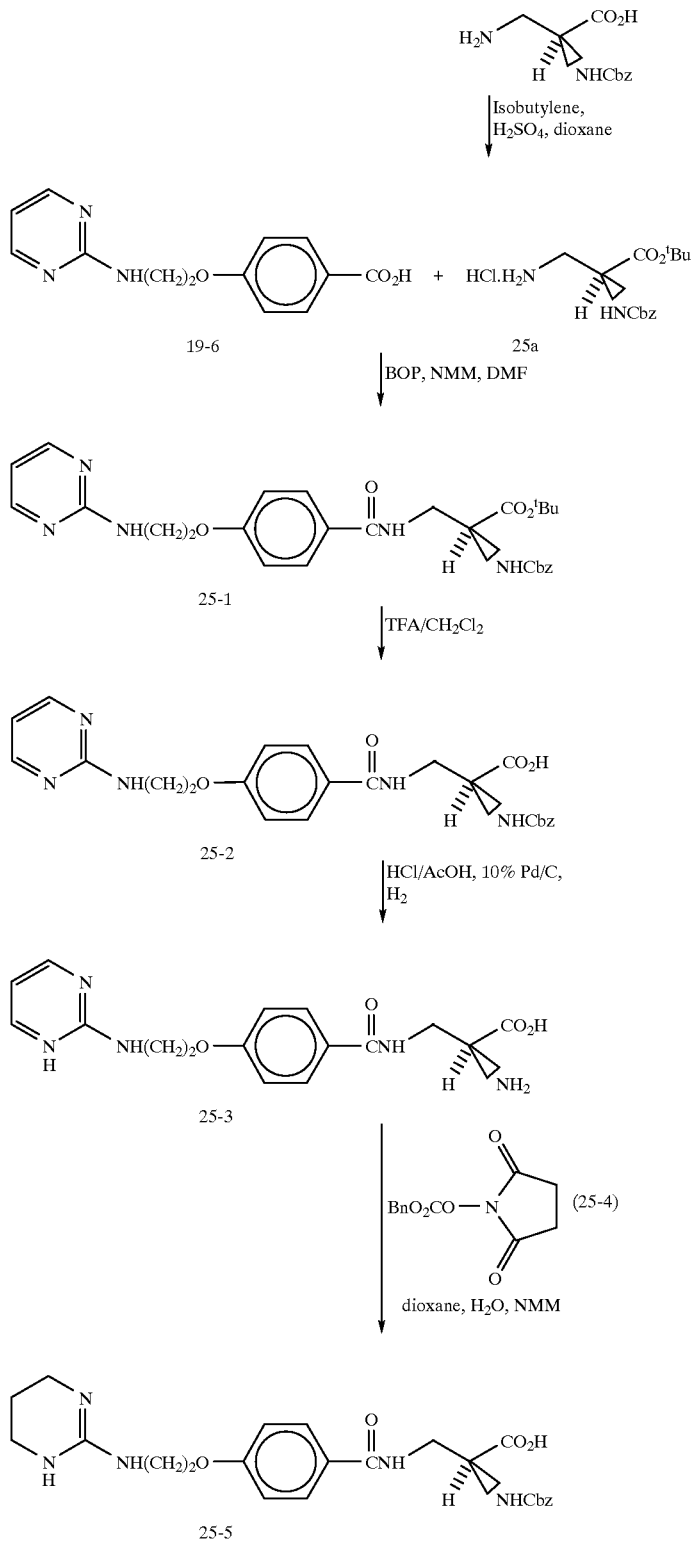

tert-Butyl 2(S)-Benzyloxycarbonylamino-3-aminopropionate hydrochloride (25-a)

Following the procedure for converting 2-1 b to 2-1,3-amino-2(S)-benzyloxycarbonylaminopropionic acid (230 mg, 1.0 mmol; Fluka) gave 25-a as a white solid.

$^1$H NMR (300 MHz, D$_2$O) δ 7.45 (br s, 5H), 5.18 (s, 2H), 4.35 (m, 1H), 3.35 (m, 1H), 3.05 (m, 1H), 1.45 (s, 9H).

4-[2-(Pyrimidin-2-ylamino)ethyloxy]benzoyl-2(S)-benzyloxycarbonyl-amino-β-alanine tert-butyl ester (25-1)

To a stirred solution of 19-6 (400 mg, 1.5 mmol), 25-a (538, 1.6 mmol), DMF (10 mL), and NMM (6.27 mg, 6.0 mmol) at ambient temperature was added BOP reagent (717 mg, 1.6 mmol). After 24 h, the reaction mixture was diluted with EtOAc and then washed with H$_2$O and brine, dried (MgSO$_4$) and concentrated. Flash chromatograpy (silica, 60% EtOAc/hexanes) gave 25-1 as a yellow oil. TLC R$_f$ 0.14 (silica, 60% EtOAc/hexanes);

$^1$H NMR (300 MHz, CD$_3$OD) δ 8.22 (m, 2H), 7.68 (m, 2H), 7.24 (m, 5H), 6.92 (m, 2H), 6.06 (m, 1H), 5.00 (m, 2H), 4.30 (m, 1H), 4.13 (m, 2H), 3.72 (m, 2H), 3.67 (m, 2H), 1.32 (s, 9H).

4-[2-(Pyrimidin-2-ylamino)ethyloxy]benzoyl-2(S)-benzyloxycarbonyl-amino-β-alanine (25-2)

A solution of 25-1 (840 mg, 1.6 mmol) and CH$_2$Cl$_2$ (10 ml) at ambient temperature was treated with TFA (10 ml). After stirring for 4.0 h, the reaction mixture was concentrated and the residual TFA removed azeotropically with toluene. Trituration of the resulting waxy solid with ether provided 25-2 as a white solid.

1H NMR (300 MHz, CD$_3$OD) δ 8.41 (m ,2H), 7.67 (m, 2H), 7.22 (m, 5H), 6.91 (m, 2H), 6.82 (m, 2H), 4.98 (m, 2H), 4.38 (m, 1H), 4.20 (m, 2H), 3.83 (m, 2H), 3.72 (m, 1H), 3.62 (m, 1H).

4-[2-(3,4,5,6-Tetrahydropyrimidin-2-ylamino)ethyloxy]benzoyl-2(S)-amino-β-alanine (25-3)

A mixture of 25-2 (500 mg, 1.0 mmol), conc. HCl (6 mL), AcOH (30 mL) and 10% Pd/C (300 mg) was shaken on a Parr apparatus under a hydrogen atmosphere (70 psi) at ambient temperature for 3.0 h. The mixture was then filtered through a celite pad, the filtrate concentrated and the residual AcOH removed azeotropically with toluene. The residue was triturated with 8:1:1 ethanol/NH$_4$OH/H$_2$O. The solid was collected by filtration, washed with ether and dried in vacuo to give 25-3 as a yellow solid. TLC R$_f$ 0.17 (silica, 8:1:1 ethanol/NH$_4$OH/H$_2$O);

$^1$H NMR (300 MHz, CD$_3$OD) δ 7.84 (d, J=9 Hz, 2H), 7.02 (d, J=9 Hz, 2H), 4.22 (m, 1H), 4.12 (m, 2H), 4.00–3.30 (m, 8H), 1.92 (m, 2H).

4-[2-(3,4,5,6-Tetrahydropyrimidin-2-ylamino)ethyloxy]benzoyl-2(S)-benzyloxycarbonylamino-β-alanine (25-5)

A stirred solution of 25-3 (360 mg, 1.0 mmol), dioxane (5 mL), H$_2$O (5 mL) and NMM (453 μL, 4.0 mmol) at ambient temperature was treated with 25-4 (Aldrich) (257 mg, 1.0 mmol). After 1.0 h the solution was concentrated. Flash chromatography (silica, 10:1:1 ethanol/NH$_4$OH/H$_2$O) gave 25-5 as a white solid. TLC R$_f$ 0.34 (silica, 10; 1:1 ethanol/NH$_4$OH/H$_2$O); $^1$H NMR (300 MHz, DCl/CD$_3$OD) δ 7.80 (d, J=9 Hz, 2H), 7.31 (m, 5H), 7.02 (d, J=9 Hz, 2H), 5.07 (m, 2H), 4.50 (m, 1H), 4.19 (m, 2H), 3.77 (m, 2H), 3.62 (m, 2H), 3.38 (m, 4H), 1.97 (m, 2H).

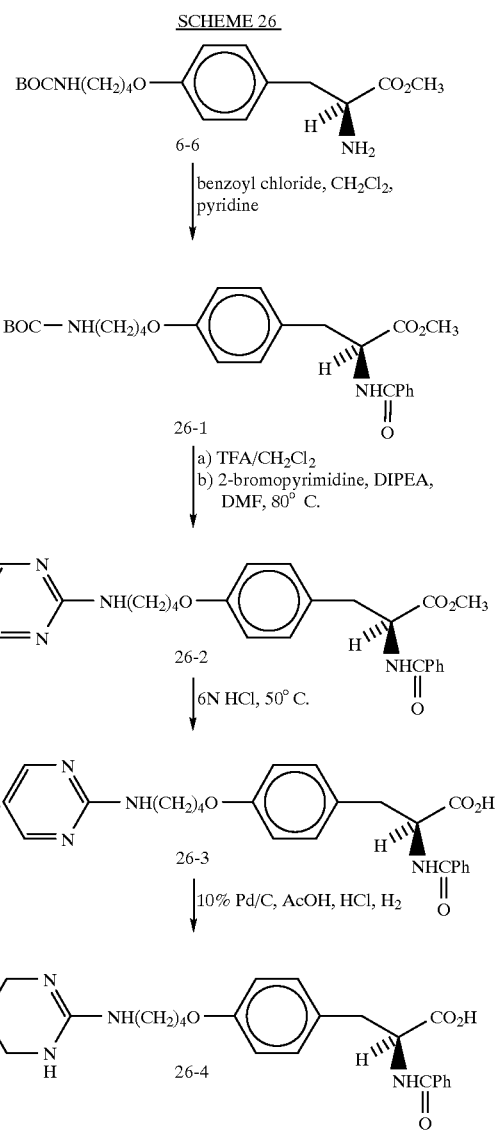

SCHEME 26 a) TFA/CH$_2$Cl$_2$
b) 2-bromopyrimidine, DIPEA, DMF, 80° C.

6N HCl, 50° C.

10% Pd/C, AcOH, HCl, H$_2$

Methyl 2(S)-benzoylanino-3-[4-(4-N-Boc-aminobutyloxy)phenyl]-propionate (26-1)

A solution of 6-6 (600 mg, 1.6 mmol), pyridine (265 μL, 3.3 mmol) and CH$_2$Cl$_2$ (10 mL) at ambient temperature was treated with benzoyl chloride (228 μL, 2.0 mmol). After 24 h the solution was diluted with EtOAc and washed with H$_2$O, sat. NaHCO$_3$, 10% KHSO$_4$ and brine, dried (MgSO$_4$) and concentrated. Flash chromatography (silica, 30% EtOAc/hexanes) gave 26-1 as a white solid.

TLC R$_f$ 0.15 (silica, 30% EtOAc/hexanes); $^1$H NMR (300 MHz, CD$_3$OD) δ 7.65 (m, 2H), 7.39 (m, 3H), 7.07 (m, 2H), 6.76 (m, 2H), 4.05 (m, 1H), 3.88 (m, 2H), 3.66 (s, 3H), 3.20–2.90 (m, 4H), 1.80–1.50 (m, 4H), 1.39 (s, 9 h).

Methyl 2(S)-benzoylamino-3-[4-(4-pyrimidin-2-ylaminobutyloxy)-phenyl]propionate (26-2)

A solution of 26-1 (375 mg, 0.8 mmol), CH$_2$Cl$_2$ (4 mL) and TFA (4 mL) was stirred at ambient temperature for 2.0 h. The solution was concentrated and the residual TFA removed azeotropically with toluene. The residue was dissolved in DMF (4 mL) then treated sequentially with DIPEA (414 μL, 3.2 mmol) and 2-bromopyrimidine (152 mg, 0.95 mmol) and then heated at 80° C. for 20 h. The cooled reaction mixture was diluted with EtOAc and then washed with H$_2$O and brine, dried (MgSO$_4$) and concentrated. Flash chromatography (silica, 50% to 80% EtOAc/hexanes) gave 26-2 as a brown oil.

TLC R$_f$ 0.34 (silica, 80% EtOAc/hexanes); $^1$H NMR (300 MHz, CD$_3$OD) δ 8.17 (m, 2H), 7.68 (d, J=9 Hz, 2H), 7.40 (m, 3H), 7.09 (m, 2H), 6.76 (d, J=9 Hz, 2H), 6.49 (m, 1H), 4.05 (m, 1H), 3.90 (m, 3H), 3.68 (s, 3H), 3.40, 2.90 (m, 4H), 1.72 (m, 4H).

2(S)-Benzoylamino-3-[4-(4-pyrimidin-2-ylaminobutyloxy) phenyl]-propionic acid hydrochloride (26-3)

A solution of 26-2 (250 mg, 0.56 mmol), in 6N HCl (6 mL) was heated at 60° C. for 2.0 h. The solution was concentrated to give 26-3 as a solid, which was used directly in the next step.

2(S)-Benzoylamino-3-[4-(4-(3,4,5,6-tetrahydropyrimidin-2-ylamino)-butyloxy)phenyl]propionic acid (26-4)

A mixture of 26-3 (250 mg, 0.56 mmol), AcOH (20 mL), conc. HCl (3 mL) and 10% Pd/C (150 mg) was shaken on the Parr apparatus (60 psi) at ambient temperature for 2.5 h. The reaction mixture was then filtered through a celite pad and the filtrate concentrated. Flash chromatography (silica, 10:1:1 to 9:1:1 ethanol/NH$_4$OH/H$_2$O) gave 26-4 as a white solid.

TLC R$_f$ (silica, 9:1:1 ethanol/NH$_4$OH/H$_2$O); $^1$H NMR (400 MHz, CD$_3$OD) δ 7.78 (m, 2H), 7.60–7.40 (m, 3H), 7.17 (d, J=9 Hz, 2H), 6.79 (d, J=9 Hz, 2H), 4.70 (m, 1H), 3.96 (m, 2H), 3.33 (m, 4H), 3.30 (m, 1H), 3.16 (m, 2H), 3.11 (m, 1H), 1.95 (m, 2H), 1.80 (m, 2H), 1.73 (m, 2H).

SCHEME 27

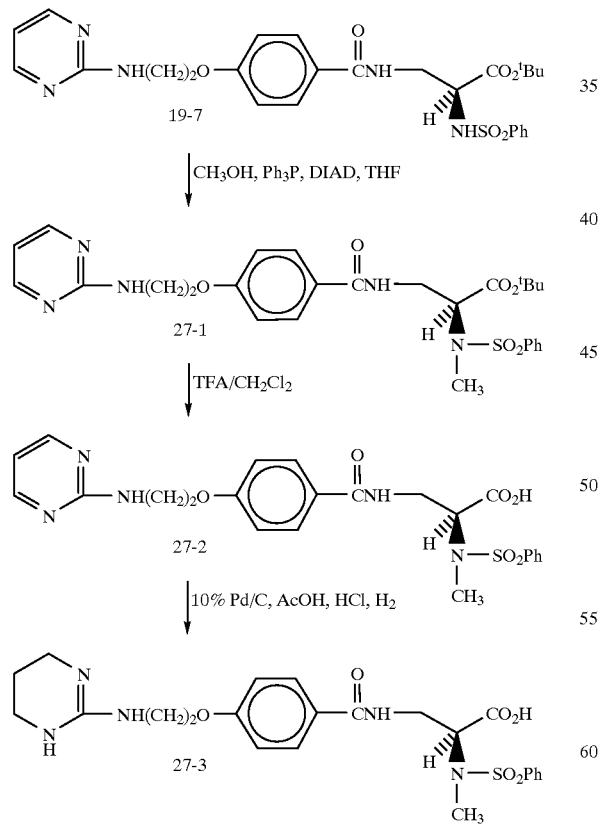

4-[2-(Pyrimidin-2-ylamino)ethyloxy]benzoyl-2(S)-(N-methyl)-phenylsulfonylamino-β-alanine tert-butyl ester (27-1)

A solution of 19-7 (190 mg, 0.35 mmol), CH$_3$OH (28 µL, 0.7 mmol), Ph$_3$P (101 mg, 0.39 mmol), DIAD (758 µL, 0.9 mmol) and THF (10 mL) was stirred for 24 h at ambient temperature. The reaction mixture was then diluted with EtOAc and washed with H$_2$O and brine, dried (MgSO$_4$) and concentrated. Flash chromatography (silica, CHCl$_3$ saturated with NH$_3$) gave crude 27-1 as a gum.

TLC R$_f$=0.21 (silica, 20% acetone/CH$_2$Cl$_2$); $^1$H NMR (300 MHz, CDCl$_3$) δ 8.29 (d, J=5 Hz, 1H), 7.90–7.40 (m, 10H), 6.90 (d, J=9 Hz, 2H), 6.57 (m, 1H), 4.72 (m, 1H), 4.19 (m, 2H), 3.87 (m, 2H), 2.90 (s, 3H), 1.30 (s, 9H).

4-[2-(Pyrimidin-2-ylamino)ethyloxy]benzoyl-2(S)-(N-methyl)-phenylsulfonylamino-β-alanine (27-2)

A solution of 27-1 (190 mg, 0.35 mmol), TFA (4 mL) and CH$_2$Cl$_2$ (8 mL) was stirred at ambient temperature for 4 h. The reaction was concentrated and the residual TFA removed azeotropically with toluene. Flash chromatography (silica, 95/2.5/2.5 CH$_2$Cl$_2$/CH$_3$OH/AcOH) gave 27-2 as a colorless foam.

TLC R$_f$=0.26 (silica, 9:0.5:0.5 CH$_2$Cl$_2$/CH$_3$OH/AcOH); $^1$H NMR (300 MHz, CD$_3$OD) δ 8.30 (d, J=5 Hz, 2H), 7.74 (d, J=11 Hz, 2H), 7.71 (d, J=9 Hz, 2H), 7.45–7.25 (m, 3H), 6.99 (d, J=9 Hz, 2H), 6.62 (m, 1H), 5.80 (m, 1H), 4.21 (m, 2H), 3.90 (m, 1H), 3.79 (m, 2H), 3.60 (m, 1H), 2.89 (s, 3H).

4-[2-(3,4,5,6-Tetrahydropyrimidin-2-ylamino)ethyloxy] benzoyl-2(S)-(N-methyl)phenylsulfonylamino-β-alanine (27-3)

A mixture of 27-2 (190 mg, 0.35 mmol), HOAc (10 mL), conc. HCl (0.6 mL) and 10% Pd/C (38 mg) was shaken on the Parr apparatus (40 psi) at ambient temperature for 2.0 h. The reaction mixture was filtered through a celite pad and the filtrate concentrated. Flash chromatography (silica, effianol/NH$_4$OH/H$_2$O 9:0.5:0.5) gave 27-3 as a colorless lyophilizate.

TLC R$_f$ 0.34 (silica, 8:1:1 ethanol/NH$_4$OH/H$_2$O); $^1$H NMR (300 MHz, CDCl$_3$) δ 7.80 (m, 4H), 7.55–7.35 (m, 3H), 7.02 (d, J=9 Hz, 2H), 7.02 (d, J=9 Hz, 2H), 4.95 (m, 1H), 4.20 (m, 2H), 3.86 (m, 1H), 3.69 (m, 1H), 3.59 (m, 2H), 3.38 (m, 4H), 2.88 (s, 3H), 1.95 (m, 2H)

SCHEME 28

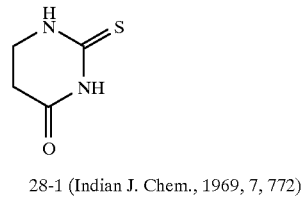

28-1 (Indian J. Chem., 1969, 7, 772)

| THF, CH$_3$I 28-2

| DMF, DIPEA, 12-1, 100° C.

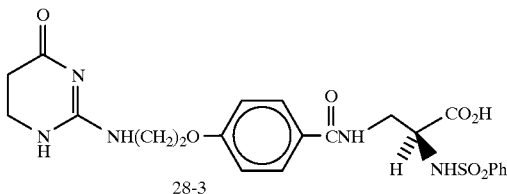

(5,6-Dihydro-4-keto-(1H)-pyrimidin-2-yl)methylsulfide (28-2)

A suspension of 28-1 (1.98 g, 15.2 mmol) in THF (40 mL) was treated with iodomethane and stirred at ambient temperature for 60 h. The heterogeneous reaction mixture was then filtered to give 28-2 as a colorless crystalline solid m.p.=205° C. (D).

$^1$H NMR (300 MHz, CD$_3$OD) δ 3.90 (t, J=7 Hz, 2H), 2.91 (t, J=7 Hz, 2H), 2.77 (s, 3H).

4-[2-(N-(5,6-Dihydro-4-keto-1 (H)-pyrimidin-2-yl)amino) ethyloxy]-benzoyl-2(S)-phenylsulfonylamino-β-alanine (28-3)

A solution of 28-2 (272 mg, 1.0 mmol), 12-1 (222 mg, 0.5 mmol), DIPEA (261 μL, 1.5 mmol) and DMF (5 mL) was heated at 100° C. for 20 h. The cool reaction mixture was concentrated.

Flash chromatography (silica, 95% ethanol/NH$_4$OH) and preparative HPLC (C18, 0.1% TFA in H$_2$O/CH$_3$CN) provided pure 28-3 as a colorless solid after lyophilization.

TLC R$_f$ 0.58 (silica, 95% ethanol/NH$_4$OH); $^1$H NMR (300 MHz, CD$_3$OD) δ 7.83 (d, J=7 Hz, 2H), 7.78 (d, J=9 Hz, 2H), 7.48 (m, 3H), 7.02 (d, J=9 Hz, 2H), 4.26 (m, 2H), 4.20 (m, 1H), 3.80–3.60 (m, 4H), 3.48 (m, 1H), 2.76 (t, J=7 Hz, 2H).

SCHEME 29

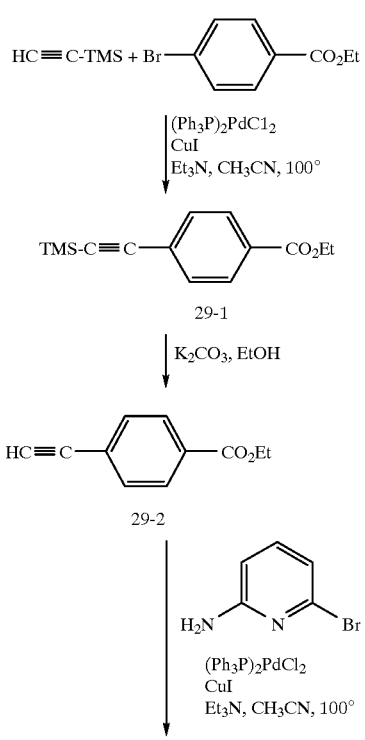

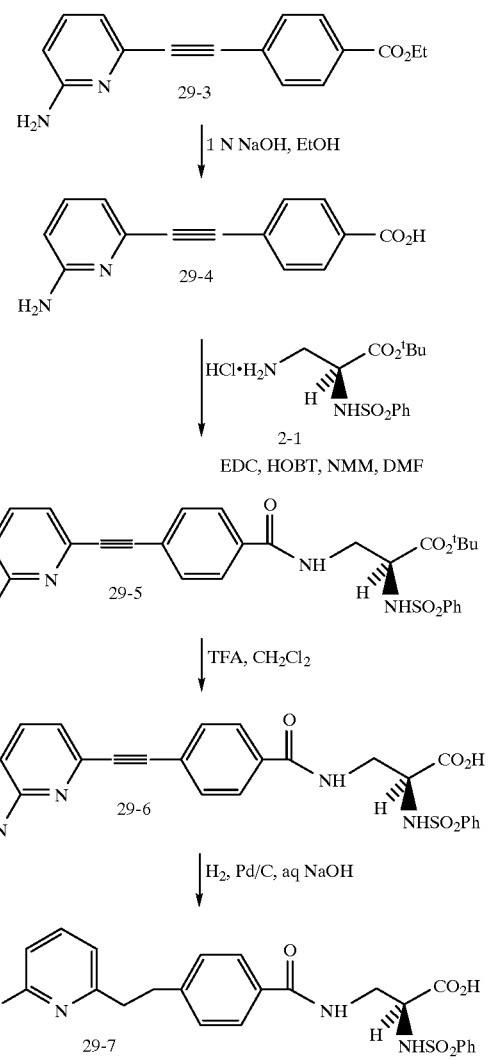

Ethyl 4-(trimethylsilylethynyl)benzoate (29-1)

TMS-acetylene (Aldrich) (5.0 mL, 35.5 mmol), ethyl 4-bromobenzoate (58 mL, 35.5 mmol) and Et$_3$N (20 mL, 144 mmol) were combined in 50 mL CH$_3$CN in a glass pressure tube. (Ph$_3$P)$_2$PdCl$_2$ (198 mg, 0.28 mmol) and CuI (100 mg, 0.53 mmol) were added, and the reaction was sealed and heated at 100° for 18 h. Dilution with EtOAc, washing twice with water, then brine, drying and concentration provided 29-1 as a brown liquid.

R$_f$ 0.60 (silica, 10% EtOAc/hexane). $^1$H NMR (300 MHz, CDCl$_3$) δ 7.97 (d, J=8 Hz, 2H), 7.51 (d, J=9 Hz, 2H), 4.37 (q, J=7 Hz, 2H), 1.40 (t, J=7 Hz, 3H), 0.26 (s, 9H).

Ethyl-4-ethynylbenzoate (29-2)

Silylacetylene 29-1 (9.40 g, 38 mmol) was dissolved in 100 mL EtOH, K$_2$CO$_3$ (0.25 g 1.8 mmol) was added and the mixture was stirred for 16 h, concentrated, and purified by flash chromatography (silica, 5% Et$_2$O/hexane) provided 29-2 as a yellow oil.

R$_f$ 0.47 (silica, 10% EtOAc/hexane). $^1$H NMR (300 MHz, CDCl$_3$) δ 8.00 (d, J=8 Hz, 2H), 7.55 (d, J=8 Hz, 2H), 4.38 (q, J=7 Hz, 2H), 3.22 (s, 1H), 1.40 (t, J=7 Hz, 3H).

Ethyl 4-(2-aminopyridin-6-ylethynyl)benzoate (29-3)

2-Amino-6-bromopyridine (0.38 g, 2.4 mmol), alkyne 29-2 (0.35 g, 2.0 mmol), Et$_3$N (1.0 mL, 7.2 mmol), (Ph$_3$P)$_2$PdCl$_2$ (76 mg, 0.11 mmol), an CuI (26 mg, 0.14 mmol)

were combined in 5 mL CH₃CN, sealed in a glass pressure tube and heated to 100° for 3 h. The mixture was diluted with EtOAc, washed with water and brine, dried (MgSO₄), concentrated, and purified by flash chromatography (silica, 5% acetone/hexane), to give 29-3 as a tan solid.

$R_f$ 0.45 (silica, 10% acetone/hexane). ¹H NMR (300 MHz, CDCl₃) δ 8.03 (d, J=8 Hz, 2H), 7.64 (d, J=8 Hz, 2H), 7.44 (t, J=8 Hz, 1H), 6.95 (d, J=7 Hz, 1H), 6.50 (d, J=8 Hz, 1H), 4.55 (br s, 2H), 4.39 (q, J=7 Hz, 2H), 1.40 (t, J=7 Hz, 3H).

4-(2-Aminopyridin-6-ylethynyl)benzoic acid (29-4)

Ester 29-3 (300 mg, 1.13 mmol) and 1N NaOH (2.8 mL, 2.8 mmol) were combined in 6 mL EtOH. After 16 h the mixture was concentrated, EtOAc was added, and water and 10% KHSO₄ were added to pH 7. The resulting precipitate was collected, the organic phase was washed with brine, dried and concentrated. Both fractions contained 29-4, an orange/yellow solid.

$R_f$ 0.50 (silica, 18:1:1 CH₂Cl₂/MeOH/HOAc). ¹H NMR (400 MHz, CD₃OD+NaOD) δ 7.95 (d, J=9 Hz, 2H), 7.53 (d, J=9 Hz, 2H), 7.46 (dd, J=9,7 Hz, 1H), 6.84 (dd, J=7,1 Hz, 1H), 6.58 (dd, J=8,1 Hz, 1H).

4-(2-Aminopyridin-6-ylethynyl)benzoyl-2(S)-phenylsulfonyl-amino-β-alanine t-butyl ester (29-5)

Acid 29-4 (234 mg, 0.98 mmol), amine 2-1 (351 mg, 0.98 mmol), EDC (225 mg, 1.2 mmol), HOBT (159 mg, 1.2 mmol) and NMM (323 μL, 2.9 mmol) were combined in 5 mL DMF. After 16 h the mixture was diluted with EtOAc, washed with water, sat. NaHCO₃ and brine, dried (MgSO₄), concentrated and chromatographed (silica, 80% EtOAc/hexane) providing 29-5.

$R_f$ 0.53 (EtOAc, silica). ¹H NMR (300 MHz, CDCl₃) δ 7.86 (d, J=8 Hz, 2H), 7.76 (d, J=9 Hz, 2H), 7.62 (d, J=9 Hz, 2H), 7.57–7.41 (m, 4H), 6.95 (dd, J=7,1 Hz, 1H), 6.86 (br m, 1H) 6.50 (dd, J=8, 1H, 1H), 5.92 (br m, 1H), 458 (br s, 2H), 4.00–3.84 (m, 2H), 3.62 (m, 1H), 1.29 (s, 9H).

4-(2-Aminopyridin-6-ylethynyl)benzoyl-2(S)-phenylsulfonylamino-β-alanine (29-6)

Ester 29-5 (375 mg, 0.72 mmol), was disso&lved in 3.6 mL CH₂Cl₂/3.6 mL TFA. After 2 h the reaction was concentrated, azeotroped with toluene, and triturated with 10:1:1 EtOH/NH4OH/H₂O, providing 29-6 as a light yellow solid.

¹H NMR (400 MHz, D₂+NaOD) δ 7.55–7.45 (m, 4H), 7.45–7.36 (m, 3H), 7.10–7.05 (m, 3H), 6.86 (m, 1H), 6.54 (m, 1H), 3.54–3.42 (m, 2H), 3.04 (m, 1H).

4-[2-(2-Aminopyridin-6-yl)ethyl]benzoyl-2(S)-phenylsulfonylamino-β-alanine (29-7)

Alkyne 29-6 (60 mg, 0.13 mmol), was suspended in 1.3 mL H₂O, 1N NaOH was added until the mixture was homogeneous, 10% Pd/C (12 mg) was added, and an H₂ balloon was applied. After 16 h the reaction was filtered, concentrated, and purified by flash chromatography (silica, 12:10:1:1 EtOAc/EtOH/NH₄OH/H₂O) providing 29-7 as a white solid.

¹H NMR (300 MHz, D₂O+NaOD) δ 7.73 (d, J=8 Hz, 2H), 7.52 (d, J=9 Hz, 2H), 7.34 (d, J=8 Hz, 2H), 7.30–7.15 (m, 3H), 6.67 (d, J=7 Hz, 1H), 6.62 (d, J=8 Hz, 1H), 3.80–3.68 (m, 2H), 3.35–3.05 (m, 5H).

SCHEME 30

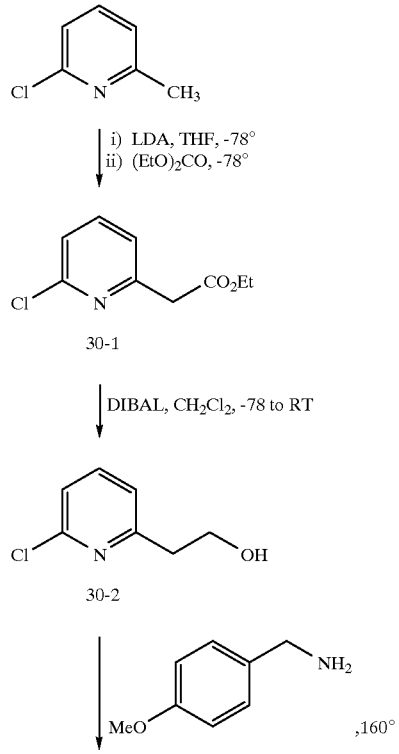

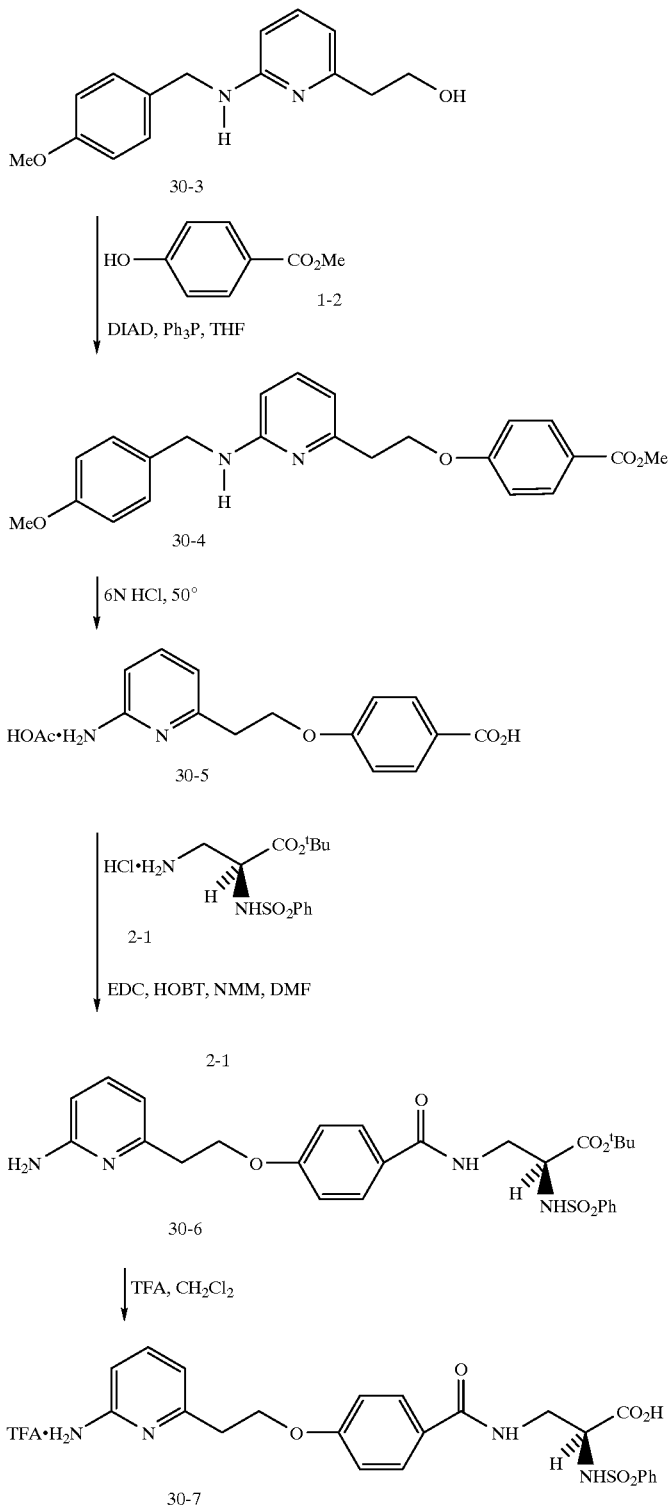

Ethyl 2-Chloropyridin-6-ylacetate (30-1)

LDA (69 mmol) was prepared in 50 mL THF, cooled to −780°, and 6-chloro-2-picoline (Aldrich) (3.7 mL, 34 mmol) was added dropwise, forming a precipitate. After 15 min, diethylcarbonate (4.9 mL, 41 mmol) was added, the burgundy solution was stirred at −78° for 15 min more then quenched with sat. $NH_4Cl$. The mixture was warmed to RT, extracted twice with EtOAc, the organic layers were washed with brine, dried ($MgSO_4$), and concentrated. Flash chromatography (silica, 10% EtOAc/hexane) provided 30-1 as a yellow oil.

$R_f$ 0.41 (silica, 20% EtOAc/hexane). $^1$H NMR (400 MHz, $CDCl_3$) δ 7.64 (d, J=8 Hz, 1H), 7.27–7.24 (m, 2H), 4.19 (q, J=7 Hz, 2H), 3.83 (s, 2H), 1.27 (t, J=7 Hz, 3H).

2-(2-Chloropyridin-6-yl)ethanol (30-2)

Ester 30-1 (1.34 g, 6.7 mmol) was dissolved in 10 mL CH$_2$Cl$_2$ at −78°, DIBAL (1M in CH$_2$Cl$_2$, 17 mL, 17 mmol) was added, the mixture was warmed to RT for 15 min before quenching in a mixture of 25 mL saturated aqueous Na-K tartrate and 100 mL EtOAc. This mixture was shaken vigorously. The phases were allowed to separate, and the organic layer was washed with brine, dried (MgSO$_4$), concentrated and chromatographed (silica, 40% EtOAc/hexane), providing 30-2 as a yellow oil.

R$_f$ 0.26 (silica, 50% EtOAc/hexane). $^1$H NMR (400 MHz, CDCl$_3$) δ 7.59 (t, J=8 Hz, 1H), 7.20 (t, J=8 Hz, 1H), 7.12 (d, J=8 Hz, 1H), 4.02 (q, J=6 Hz, 2H), 3.10 (t, J=6 Hz, 1H), 3.01 (t, J=5 Hz, 2H).

2-[2-(4-Methoxybenzylamino)pyridin-6-yl]ethanol (30-3)

Chloropyridine 30-2 (150 mg, 0.95 mmol) and 4-methoxybenzylamine (4 mL, 31 mmol) were combined neat and heated in a sealed tube at 160° for 4 days. After diluting with EtOAc and water the pH was adjusted to 7 phases separated and the organic phase was washed with brine, dried (MgSO$_4$) and concentrated. Flash chromatography (twice on silica, 50% and 40% EtOAc/hexane) provided 30-3 as a yellow semi-solid.

R$_f$ 0.38 (silica, 50% EtOAc/hexane). $^1$H NMR (400 MHz, CDCl$_3$) δ 7.34 (t, J=8 Hz, 1H), 7.29–7.23 (m, 3H), 6.90–6.85 (m 3H), 6.43 (d, J=7 Hz, 1H), 6.26 (d, J=8 Hz, 1H), 4.76 (brm, 1H), 4.39 (d, J=6 Hz, 2H), 3.95 (t, J=5 Hz, 2H), 3.80 (s, 3H), 2.84 (t, J=5 Hz, 2H).

Methyl 4-[2-(4-methoxybenzylamino)pyridin-6-yl) ethyloxy]benzoate (30-4)

Methyl 4-hydroxybenzoate (68 mg, 0.45 mmol) and Ph$_3$P (175 mg, 0.67 mmol) were dissolved in 5 mL THF. A solution of 30-3 (115 mg, 0.44 mmol) and DIAD (123 μL, 0.62 mmol) in THF was slowly added. After 1 h the reaction was concentrated and purified by flash chromatography (silica, 20% EtOAc/hexane) providing 30-4 as an off-white solid.

R$_f$ 0.64 (silica, 50% EtOAc/hexane). $^1$H NMR (300 MHz, CDCl$_3$) δ 7.96 (d, J=9 Hz, 2H), 7.36 (t, J=8 Hz, 1H), 7.28–7.24 (m, 2H), 6.93–6.83 (m, 4H), 6.55 (d, J=7 Hz, 1H), 6.25 (d, J=8 Hz, 1H), 4.41–4.34 (m, 4H), 3.88 (s, 3H), 3.79 (s, 3H), 3.10 (t, J=7 Hz, 2H).

4-[2-(2-Aminopyridin-6-yl)ethyloxy)benzoic acid acetate (30-5)

Ester 30-4 (240 mg, 0.61 mmol) was dissolved in 6N HCl and heated at 50° for 16 h. Concentration and flash chromatography (silica, 18:1:1 CH$_2$Cl$_2$/MeOH/HOAc) provided 30-5 as a light orange solid.

R$_f$ 0.19 (silica, 18:1:1 CH$_2$Cl$_2$/MeOH/HOAc). $^1$H NMR (300 MHz, DMSO) δ 7.88 (d, J=8 Hz, 2H), 7.29 (t, J=8 Hz, 1H), 6.90 (d, J=8 Hz, 2H), 6.45 (d, J=7 Hz, 1H), 6.29 (d, J=8 Hz, 1H), 4.30 (t, J=7 Hz, 2H), 2.94 (t, J=6 Hz, 2H), 1.83 (s).

4-[2-(2-Aminopyridin-6-yl)ethyloxy)benzoyl-2(S)-phenylsulfonylamino-β-alanine t-butyl ester (30-6)

Acid 30-5 (100 mg, 0.31 mmol), amine 2-1 (210 mg, 0.59 mmol), EDC (90 mg, 0.47 mmol), HOBT (63 mg, 0.47 mmol) and NMM (150 μL, 1.4 mmol) were combined in 2 mL DMF at −15°. After warming to RT for 16 h the mixture was concentrated and chromatographed (silica, 9:1:1 CH$_2$Cl$_2$/MeOH/HOAc), providing 30-6.

R$_f$ 0.32 (silica, 9:1:1 CH$_2$Cl$_2$/MeOH/HOAc).

4-[2-(2-Aminopyridin-6-yl)ethyloxy]benzoyl-2(S)-phenylsulfonylamino-β-alanine (30-7)

Ester 30-6 (120 mg, 0.22 mmol) was dissolved in 1 mL CH$_2$Cl$_2$, and 1 mL TFA was added. After 1 h the reaction was concentrated azeotroped with toluene, chromatographed (silica, 18:1:1→9:1:1→CH$_2$Cl$_2$/MeOH/HOAc) and purified by prep HPLC (C$_{18}$, 0.1% TFA in H$_2$O/CH$_3$CN) providing 30-7 as a white solid.

R$_f$ 0.33 (silica, 4:1:1 CH$_2$Cl$_2$/MeOH/HOAc). $^1$H NMR (400 MHz, D$_2$O) δ 7.46 (d, J=7 Hz, 2H), 7.36–7.29 (m, 3H), 7.02–6.95 (m, 3H), 6.79 (d, J=8 Hz, 2H), 6.57 (d, J=8 Hz, 1H), 6.39 (d, J=8 Hz, 1H), 4.28 (t, J=7 Hz, 2H), 3.50–3.40 (m, 2H), 2.98 (m, 1H), 2.91 (t, J=5 Hz, 2H).

SCHEME 31

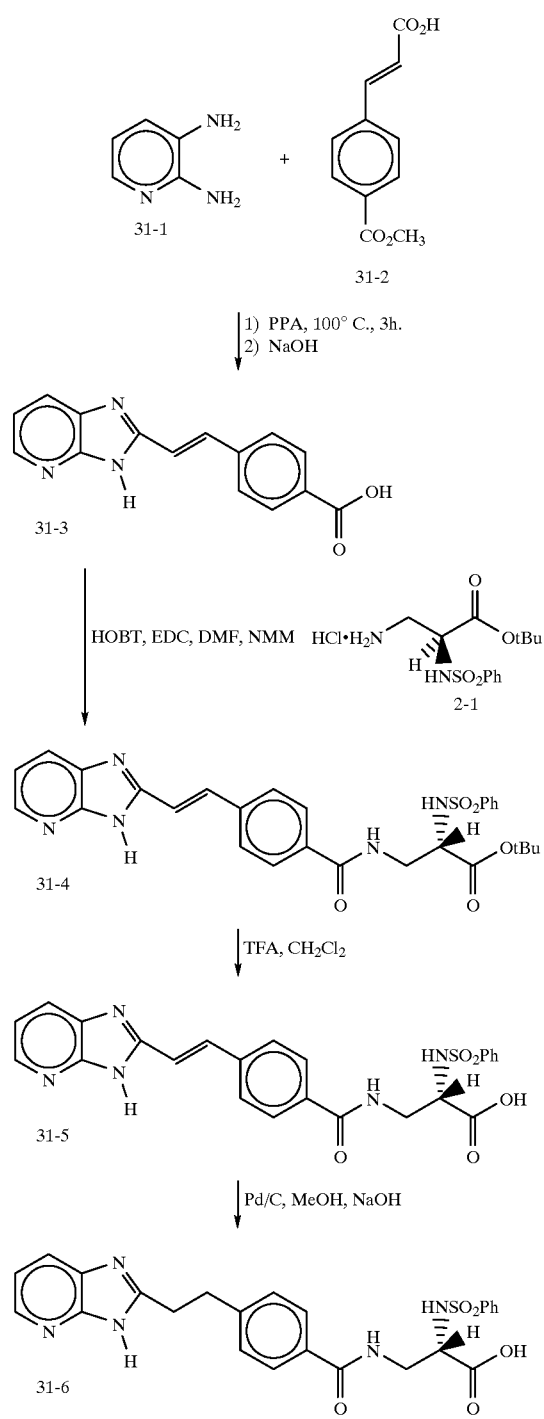

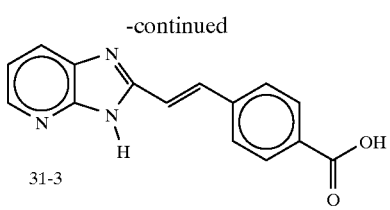

31-3

4-[2-(1H-Imidazo[4,5-b]pyridin-2-yl)ethenyl]benzoic acid (31-3)

A solution of 31-1 (546 mg, 5.0 mmol), (Aldrich) 3-2 (1030 mg, 5.0 mmol) (*Chem. Pharm. Bull.* 36(2), 495 (1988)) and PPA (20 mL) was heated at 100° C. for 3 h. After cooling, the reaction was poured into ice water and the yellow solid collected by filtration and added to 1N NaOH (50 mL). After stirring under ambient conditions for 18 h, the reaction was acidified with 12N HCl to provide 31-3 as a yellow solid.

$^1$H NMR (400 MHz, $d_6$-DMSO) δ 8.54 (m, 1H), 8.25 (m, 1H), 8.10 (d, J=8 Hz, 2H), 8.02 (d, J=16 Hz, 1H), 7.93 (d, J=8 Hz, 2H), 7.46–7.54 (m, 2H).

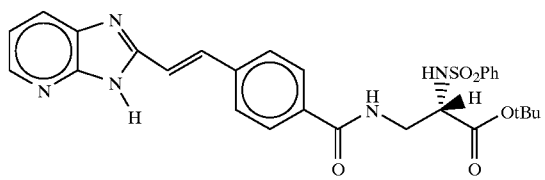

31-4

4-[2-(1H-Imidazo[4,5-b]pyridin-2-yl)ethenyl]benzoyl-2(S)-phenylsulfonylamino-β-alanine t-butyl ester (31-4)

A DMF solution (10 mL) containing 31-3 (301 mg, 1.0 mmol) 2-1 (336 mg, 1.0 mmol), HOBT (206 mg, 1.35 mmol), EDC (258 mg, 1.35 mmol) and NMM (440 μl, 4.0 mmol) was stirred under ambient conditions for 18 h. The DMF was evaporated and the residue partitioned between $CH_2Cl_2$ and $H_2O$. The organic layer was dried ($MgSO_4$) and concentrated to a yellow gum which was purified by flash chromatography (silica, 4:1, $CHCl_3 \cdot NH_3$/IPA) to provide impure 31-4 which was rechromatographed (silica, 9:1 EtOAc/IPA) to give 31-4 as a colorless foam.

$R_f$ 0.33 (silica, 9:1 EtOAc/IPA). $^1$H NMR (400 MHz, $CD_3OD$) δ 8.33 (dd, J=5, 1 Hz, 1H), 7.95 (dd, J=8, 1 Hz, 1H), 7.81–7.84 (m, 4H), 7.70–7.78 (m, 3H), 7.44–7.52 (m, 3H), 7.25–7.30 (m, 2H), 4.15 (dd, J=8, 6 Hz, 1H), 3.69 (dd, J=14, 6 Hz, 1H), 3.51 (dd, J=8 Hz, 14 Hz, 1H), 1.12 (s, 9H).

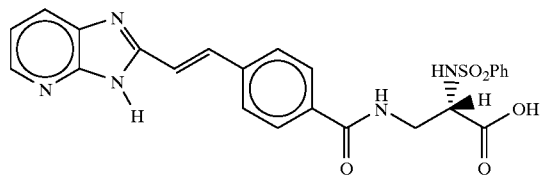

31-5

4-[2-(1H-Imidazo[4,5-b]pyridin-2-yl)ethenyl]benzoyl-2(S)-phenylsulfonylamino-β-alanine (31-5)

A $CH_2Cl_2$ solution (20 mL) of 31-4 (220 mg, 0.4 mmol) and TFA (5 mL) was stirred under ambient conditions for 5 h and concentrated. Flash chromatography (silica 9:0.5:0.5, EtOH/$H_2O$/$NH_4OH$) gave 31-5 as a solid.

$^1$H NMR (400 MHz, $CD_3OD$/NaOD) δ 8.08 (m, 1H), 7.81–7.87 (m, 5H), 7.68–7.75 (m, 3H), 7.33–7.37 (m, 4H), 6.98 (m, 1H), 3.65–3.72 (m, 2H), 3.32 (m, 1H).

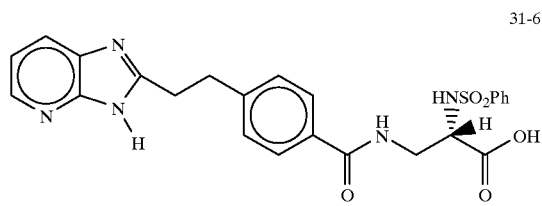

31-6

4-[2-(1H-Imidazo[4,5-b]pyridin-2-yl)ethyl]benzoyl-2(S)-phenylsulfonylamino-β-alanine (31-6)

A mixture of 31-5 (90 mg, 0.18 mmol), 10% Pd/C (50 mg), 1N NaOH (2 mL) and $CH_3OH$ (20 mL) was hydrogenated at 1 atm for 18 h. After filtration and concentration the residue was neutralized with 10% HCl and the solid chromatographed (silica, 19:1 EtOH/$NH_4OH$) to provide 31-6 as a fluffy solid after trituration with aqueous TFA.

$R_f$ 0.48 (19:1 EtOH/$NH_4OH$). $^1$H NMR (400 MHz, $CD_3OD$) δ 8.29 (dd, J=5, 1 Hz, 1H), 7.91 (dd, J=8, 1 Hz, 1H), 7.82 (m, 2H), 7.67 (d, J=8H, 2H), 7.38–7.48 (m, 3H), 7.30 (d, J=8, 1 Hz, 2H), 7.25 (m, 1H), 3.87 (m, 1H), 3.65 (m, 1H), 3.53 (m, 1H), 3.26 (m, 2H).

SCHEME 32

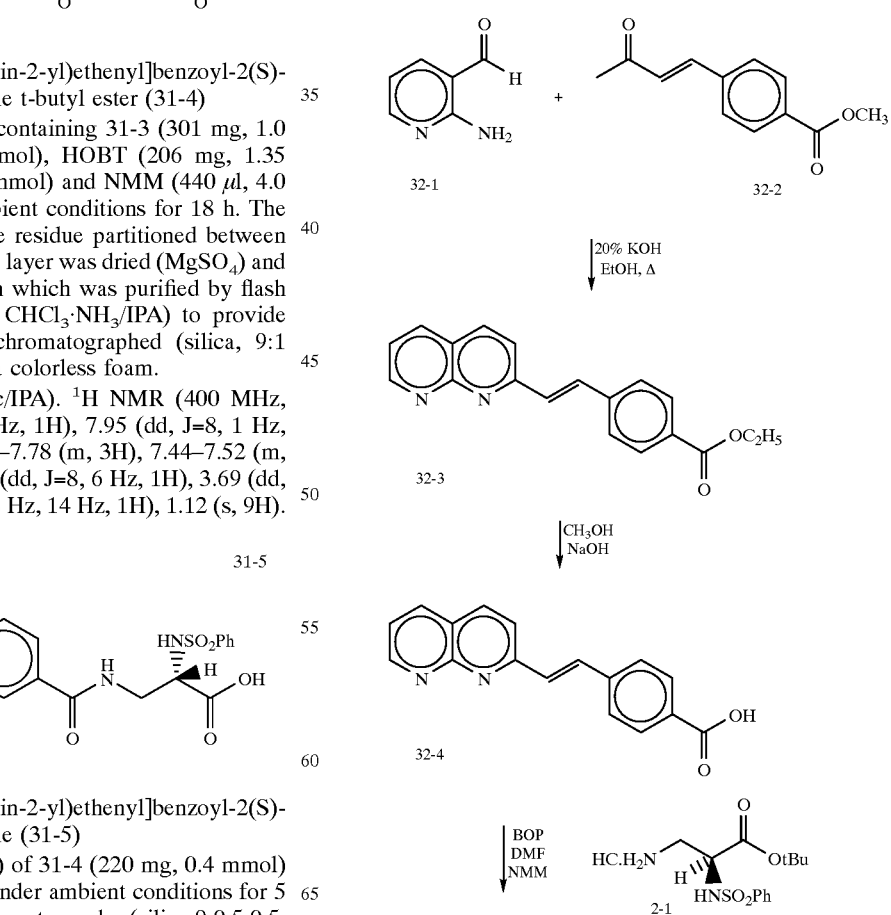

-continued

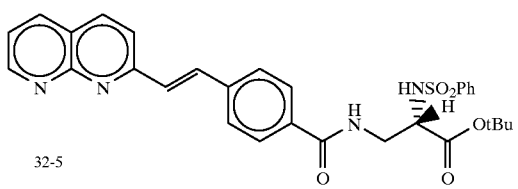
32-5

Pd/C
EtOH, H₂

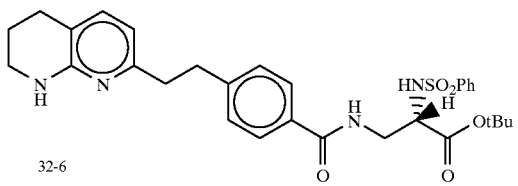
32-6

TFA/CH₂Cl₂

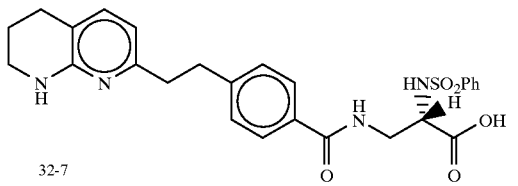
32-7

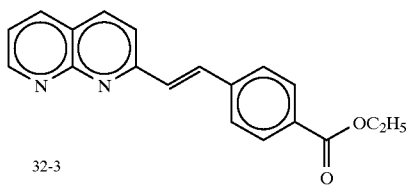
32-3

Ethyl 4-[2-(1,8-Naphthyridin-7-yl)ethenylbenzoate (32-3)

An ethanol solution (10 mL) of 32-1 (260 mg, 2.1 mmol) (*Syn. Comm.* 17(14), 1695(1987), 32-2 (435 mg, 2.1 mmol) (*Tet. Lett.* 34(4), 653(1993) and 20% KOH (100 ml) was refluxed for 6 hours. The reaction was concentrated to dryness and the residue partitioned between EtOAc and H₂O. The organic layer was washed with brine and dried (MgSO₄). Filtration and evaporation provided a yellow solid which was purified by flash chromatography (silica, 4:1 EtOAc/hexane) to give 32-3 as a cream colored solid.

$R_f$ 0.21 (silica, 3/1 EtOAc/hexane). ¹H NMR (300 MHz, CDCl₃) δ 9.12 (dd, J=4, 2 Hz, 1H), 8.15–8.21 (m, 2H), 8.02–8.11 (m, 3H), 7.66–7.72 (m, 3H), 7.48 (d, J=16 Hz, 1H), 7.45 (dd, J=8, 4 Hz, 1H), 4.39 (q, J=7 Hz, 2H), 1.41 (t, J=7 Hz, 3H).

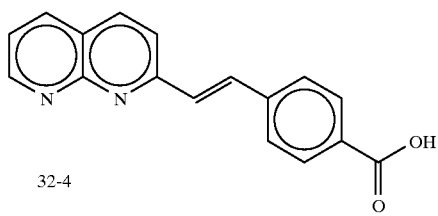
32-4

4-[2-(1,8-Naphthyridin-7-yl)ethenylbenzoic acid (32-4)

A methanol solution (100 mL) of 32-3 (420 mg, 1.38 mmol) and 1N NaOH (13.8 mL, 13.8 mmol) was stirred at ambient conditions for 18 hrs and at reflux for 2 hrs. The reaction was concentrated to dryness and the residue dissolved in H₂O and the solution acidified with 1M NaHSO₄ solution to give 32-4 as a pale yellow solid after filtration.

¹H NMR (300 MHz, CD₃OD) δ 9.05 (m, 1H), 8.43 (d, J=8 Hz, 2H), 8.04–8.10 (m, 2H), 7.96–8.01 (m, 2H), 7.83 (d, J=8 Hz, 2H), 7.61 (m, 2H).

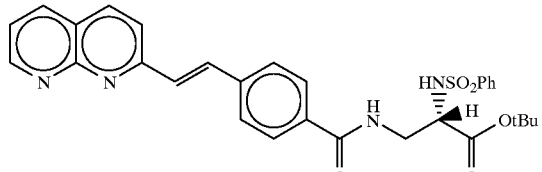
32-5

4-[2-(1,8-Naphthyidin-7-yl)ethenyl)benzoyl-2(S)-phenylsulfonylamino-β-alanine t-butylester (32-5)

To a stirred solution of 32-4 (396 mg, 1.38 mmol), 2-1 (556 mg, 1.65 mmol), NMM (728 μl, 6.62 mmol), and DMF (10 mL) was added BOP (732 mg, 1.65 mmol). After 18 h the reaction was concentrated to dryness and the residue partitioned between EtOAc and H₂O. The organic layer was washed with sat. NaHCO₃ solution, brine, dried (MgSO₄) and concentrated. Flash chromatography (silica, 3:2 CH₂Cl₂/acetone) gave 32-5 as a yellow foam.

$R_f$ 0.34 (silica, 3:2 CH₂Cl₂/acetone). ¹H NMR (300 MHz, CD₃OD) δ 9.05 (m, 1H), 8.41 (d, J=8 Hz, 2H), 7.95–8.03 (m, 2H), 7.78–7.88 (m, 6H), 7.47–7.62 (m, 5H), 4.16 (m, 1H), 3.71 (m, 1H), 3.54 (m, 1H), 1.21 (s, 9H).

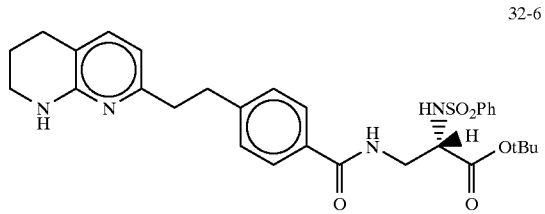
32-6

4-[2-(1,2,3,4-Tetrahydro-1,8-naphthyridin-7-yl)ethyl]benzoyl-2(S)-phenylsulfonylamino-β-alanine t-butyl ester (32-6)

A mixture of 32-5 (670 mg, 1.2 mmol), 10% Pd/C (335 mg) and ethanol (50 mL) was stirred under a hydrogen atmosphere (1 atm) for 18 h. Filtration followed by concentration gave a yellow foam. Flash chromatography (silica, 97:3 CH₂Cl₂/CH₃OH) gave 32-6 as a colorless foam.

$R_f$ 0.26 (silica, 97:3 CH₂Cl₂/CH₃OH). ¹H NMR (300 MHz, CD₃OD) δ 7.82 (d, J=7 Hz, 2H), 7.65 (d, J=8 Hz, 2H), 7.42–7.54 (m, 3H), 7.25 (d, J=8 Hz, 2H), 7.08 (d, J=7 Hz, 1H), 6.29 (d, J=7 Hz, 1H), 4.12 (dd, J=8, 6 Hz, 1H), 3.66 (dd, J=12, 6 Hz, 1H), 3.50 (dd, J=12, 8 Hz, 1H), 3.37 (t, J=6 Hz, 2H), 2.97 (t, J=6 Hz, 2H), 2.81 (t, J=6 Hz, 2H), 2.68 (t, J=6 Hz, 2H), 1.86 (m, 2H), 1.23 (s, 9H).

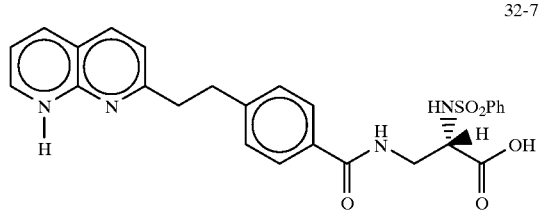

4-[2-(1,2,3,4-Tetrahydro-1,8-naphthyridin-7-yl)ethyl]benzoyl-2(S)-phenylsulfonylamino-β-alanine (32-7)

A solution of 32-6 (221 mg, 0.39 mmol), TFA (5 mL) and $CH_2Cl_2$ (50 mL) was stirred under ambient conditions for 18 h. The reaction was concentrated and the solid residue purified by flash chromatography (silica, 19:1 EtOH/$NH_4OH$) to give 32-7 as a pale yellow solid.

$R_f$ 0.63 (silica, 19:1 EtOH/$NH_4OH$). $^1H$ NMR (300 MHz, $CD_3OD$) δ 7.82 (d, J=7 Hz, 2H), 7.69 (d, J=8 Hz, 2H), 7.28–7.34 (m, 3H), 7.25 (d, J=8 Hz, 2H), 7.08 (d, J=7 Hz, 1H), 6.29 (d, J=7 Hz, 1H), 3.78 (m, 1H), 3.58–3.70 (m, 2H), 3.38 (t, J=6 Hz, 2H), 2.97 (t, J=6 Hz, 2H), 2.81 (t, J=6 Hz, 2H), 2.68 (t, J=6 Hz, 2H), 1.86 (m, 2H).

SCHEME 33

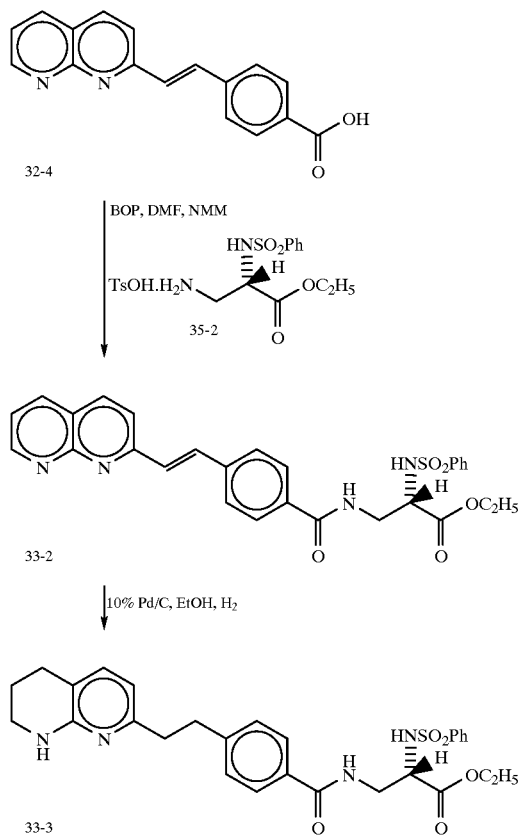

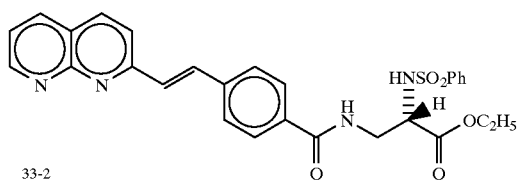

4-[2-(1,8-Naphthyridin-7-yl)ethenyl]benzoyl-2(S)-phenylsulfonylamino-β-alanine ethyl ester (33-2)

Following the procedure for coupling 32-4 to 2-1, 32-4 (2.2 g, 7.96 mmol) was coupled to 35-2 (4.24 g, 9.55 mmol). Flash chromatography (silica, 3:2 Acetone/$CH_2Cl_2$) gave 33-2 as a pale yellow foam.

$R_f$ 0.31 (silica, 1:1 acetone/$CH_2Cl_2$). $^1H$ NMR (300 MHz, $CD_3OD$) δ 9.05 (m, 1H), 8.41 (d, J=8 Hz, 2H), 7.95–8.04 (m, 2H), 7.77–7.86 (m, 6H), 7.55–7.64 (m, 5H), 4.24 (m, 1H), 3.91 (q, J=7 Hz, 2H), 3.70 (m, 2H), 3.57 (m, 2H), 1.06 (t, J=7 Hz, 3H).

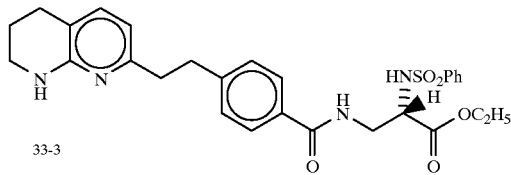

4-[2-(1,2,3,4-Tetrahydro-1,8-naphthyridin-7-yl)ethyl]benzoyl-2(S)phenylsulfonylamino-β-alanine ethyl ester (33-3)

A mixture of 33-2 (1.3 g, 2.45 mmol), 10% Pd/C (650 mg) and ethanol (100 ml) was stirred under a hydrogen atmosphere (1 atm) for 18 hr. Filtration followed by concentration gave a yellow foam which was purified by flash chromatography (silica, 49:1 EtOAc/EtOH.$NH_3$) to provide 33-3 as a pale yellow solid.

$R_f$ 0.42 (silica, 49:1 EtOAc/$NH_3$ saturated EtOH.$NH_3$). $^1H$ NMR (300 MHz, $CD_3OD$) δ 7.81 (d, J=7 Hz, 2H), 7.64 (d, J=8 Hz, 2H), 7.40–7.56 (m, 3H), 7.25 (d, J=8 Hz, 2H), 7.14 (d, J=7 Hz, 1H), 6.33 (d, J=7 Hz, 1H), 4.19 (t, J=6 Hz, 1H), 3.89 (q, J=7 Hz, 2H), 3.63 (m, 1H), 3.53 (m, 1H), 3.39 (t, J=6 Hz, 2H), 2.99 (t, J=8 Hz), 2.83 (t, J=8 Hz, 2H), 2.69 (t, J=6 Hz, 2H), 1.87 (m, 2H), 1.04 (t, J=7 Hz, 3H).

SCHEME 34
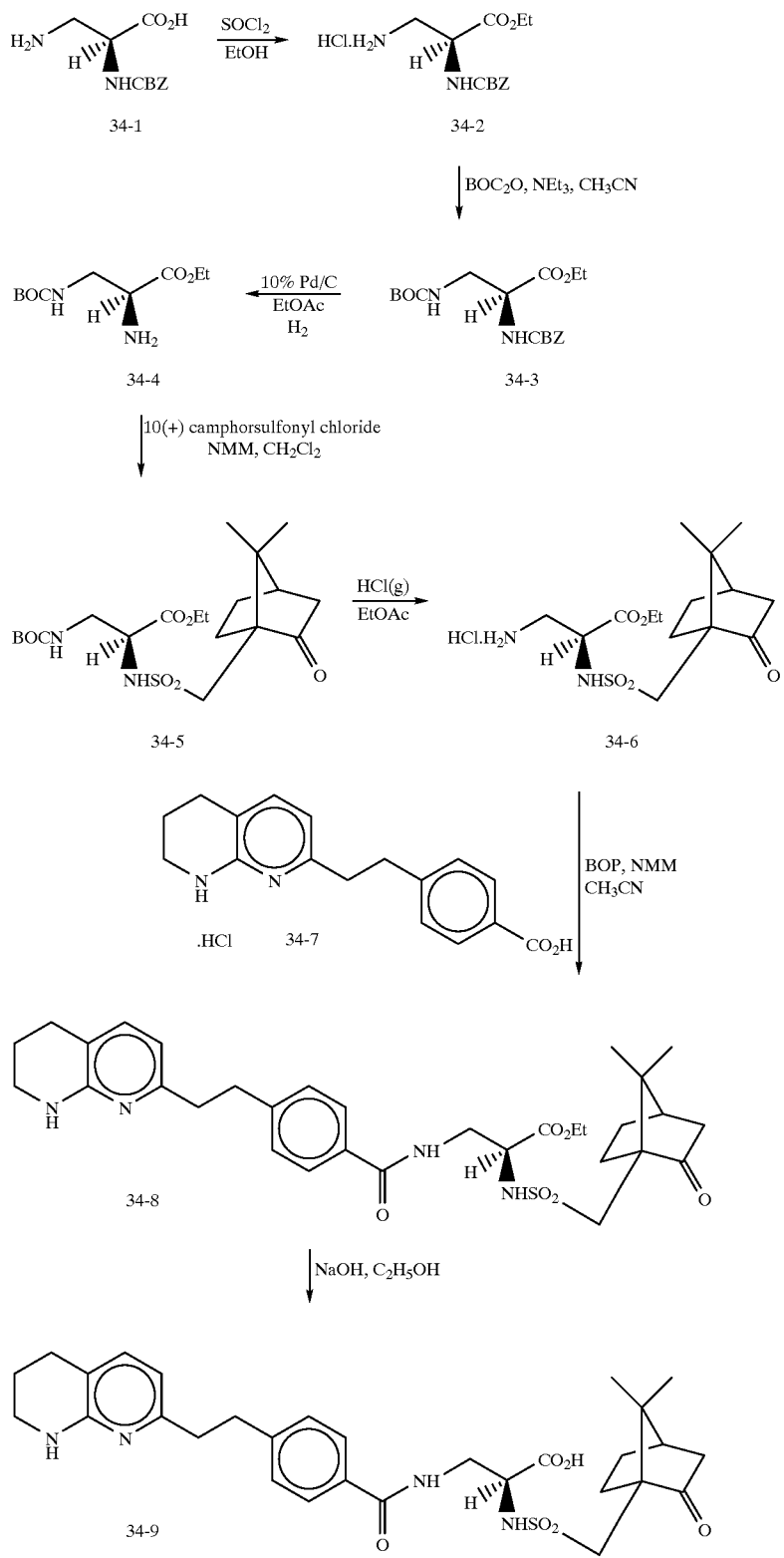

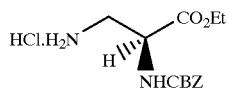

34-2

Ethyl 2(S)-Nα-Cbz-2,3-diaminopropionate hydrochloride (34-2)

34-1 (5 g, 21 mmol) was dissolved in 100 mL EtOH and cooled to 0° C. SOCl$_2$ (9.2 mL, 126 mmol) was added followed by removal of the cooling bath. After 6 hours, the reaction was concentrated to provide 34-2 as a white solid.

$^1$H NMR (300 MHz, CD$_3$OD) δ 7.35 (m, 5H), 5.14 (s, 2H), 4.44 (m, 1H), 4.22 (q, J=7 Hz, 2H), 3.43 (m, 1H), 3.20 (m, 1H), 1.25 (t, J=7 Hz, 3H).

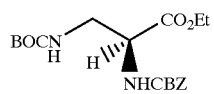

34-3

Ethyl 2(S)-Nα-Cbz-Nβ-Boc-2,3-diaminopropionate (34-3)

34-2 (2 g, 6.6 mmol) was dissolved in 60 mL CH$_3$CN. NEt$_3$ (1 mL, 7.2 mmol) was added followed by BOC$_2$O (1.58 g, 7.3 mmol). After two hours, the reaction was concentrated, diluted with EtOAc, washed with sat. NaHCO$_3$, 10% KHSO$_4$ and brine, dried (MgSO$_4$), filtered and concentrated to provide 34-3 as a clear oil. TLC R$_f$ 0.87 (silica, 80% EtOAc/hex).

$^1$H NMR (300 MHz, CDCl$_3$) δ 7.35 (s, 5H), 5.75 (bs, 1H), 5.12 (s, 2H), 4.81 (bs, 1H), 4.39 (m, 1H), 4.19 (m, 2H), 3.56 (m, 2H), 1.42 (s, 9H), 1.29 (q, J=7 Hz, 3H).

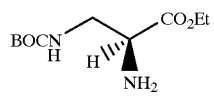

34-4

Ethyl 2(S)-Nβ-Boc-2,3-diaminopropionate (34-4)

34-3 (2.4 g, 6.6 mmol) with 10% Pd/C (240 mg) in EtOAc (35 mL) was stirred under a H$_2$ atmosphere for 20 hours. The reaction was filtered through a celite pad and concentrated to provide 34-4 as a clear oil.

TLC R$_f$ 0.13 (silica, 80% EtOAc/hex). $^1$H NMR (300 MHz, CDCl$_3$) δ 5.00 (bs, 1H), 4.19 (m, 2H), 3.55 (m, 2H), 3.25 (m, 1H), 1.44 (s, 9H), 1.29 (q, J=7 Hz, 3H).

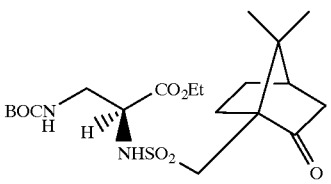

34-5

Ethyl-2(S)-Nα-(1 (S)10-camphorsulfonylamino-Nβ-Boc-2,3-diaminopropionate (34-5)

Amine 34-4 (760 mg, 3.27 mmol) was dissolved in 35 mL CH$_2$Cl$_2$ and cooled to 0° C. NMM (755 μL, 6.87 mmol) and 10(+) camphorsulfonyl chloride (1.23 g, 4.9 mmol) were added. After stirring at 0° C. for one hour, the reaction was concentrated, then diluted with EtOAc, washed with H$_2$O, sat. NaHCO$_3$, 10% KHSO$_4$ and brine, dried (MgSO$_4$), and concentrated to an oil. Flash chromatography (silica, 25–40% EtOAc/hexanes) provided 34-5 as a clear oil. TLC R$_f$ 0.66 (silica, 50% EtOAc/hexanes).

$^1$H-NMR (300 MHz, CDCl$_3$) δ 6.37 (d, J=8 Hz, 1H), 4.99 (bt, 1H), 4.32 (m, 1H), 4.23 (q, J=8 Hz, 2H), 3.56 (m, 3H), 3.0 (d, J=15 Hz, 1H), 2.4 (m, 1H), 2.05 (m, 4H), 1.43 (s, 9H), 1.30 (t, J=7 Hz, 3H), 1.00 (s, 3H), 0.91 (s, 3H).

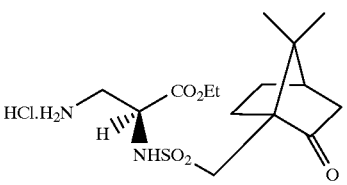

34-6

Ethyl-2(S)-Nα-(1(S)10-camphorsulfonylamino)-2,3-diamino-propionate hydrochloride (34-6)

Ester 34-5 (900 mg, 2.18 mmol) was dissolved in 15 mL EtOAc and cooled to 0° C. HCl (g) was bubbled through the reaction mixture for 15 minutes. The reaction was removed from the cooling bath and purged with Ar (g) for 20 minutes followed by concentration to provide 34-6 as a foamly solid. TLC R$_f$ 0.05 (silica, 20% MeOH/EtOAc).

$^1$H-NMR (300 MHz, CDCl$_3$): δ 4.75 (m, 1H), 4.26 (q, J=7 Hz, 2H), 3.50 (m, 4H), 2.40 (m, 3H), 1.98 (m, 4H), 1.30 (t, J=7 Hz, 3H), 1.04 (s, 3H), 0.91 (s, 3H).

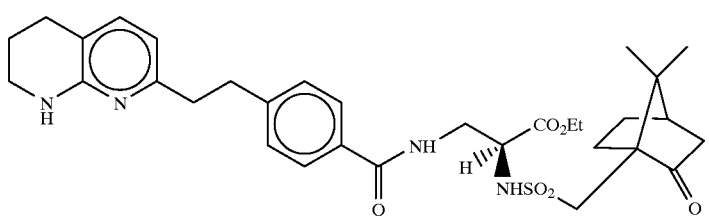

34-8

4-[2-(1,2,3,4-Tetrahydro-1,8-naphthyridin-7-yl)ethyl]benzoyl-2(S)[1(S)10-camphorsulfonylaminol]β-alanine ethyl ester (34-8)

34-7 (Scheme 37) (200 mg, 0.627 mmol), amine 34-6 (240 mg, 0.69 mmol), NMM (345 μL, 3.13 mmol) and BOP reagent (332 mg, 0.75 mmol) were combined in 5 mL CH$_3$CN. After stirring overnight, the reaction was concentrated, then diluted with EtOAc, washed with H$_2$O, sat. NaHCO$_3$ and brine, dried (MgSO$_4$), filtered and concentrated. Flash chromatography (silica, EtOAc) provided 34-8 as an off-white foamy solid.

TLC R$_f$ 0.13 (silica, EtOAc). $^1$H NMR (300 MHz, CDCl$_3$) δ 7.70 (d, J=8 Hz, 2H), 7.25 (d, J=8 Hz, 2H), 7.03 (d, J=7 Hz, 1H), 6.72 (t, J=5 Hz, 1H), 6.5 (bm, 1H), 6.28 (d, J=7 Hz, 1H), 4.79 (s, 1H), 4.42 (bs, 1H), 4.25 (q, J=7 Hz, 2H), 4.04 (m, 1H), 3.85 (m, 1H), 3.55 (d, J=15 Hz, 1H), 3.41 (m, 2H), 3.00 (m, 3H), 2.82 (t, J=4 Hz, 2H), 2.69 (t, J=6 Hz, 2H), 2.04 (m, 8H), 1.58 (bs, 3H), 1.31 (t, J=7 Hz, 3H), 1.00 (s, 3H), 0.90 (s, 3H).

34-9

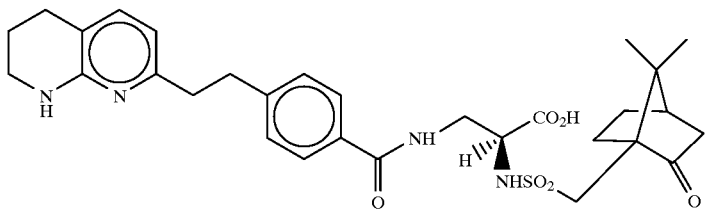

4-[2-(1,2,3,4-Tetrahydro-1,8-naphthyridin-7-yl)ethyl]benzoyl-2(S)-[1(S)10-camphorsulfonylaminol]β-alanine (34-9)

34-8 (250 mg, 0.409 mmol) was dissolved in 4 mL EtOH, 1M NaOH (1.02 mL, 1.02 mmol) was added and the reaction mixture was stirred for two hours. The reaction mixture was neutralized with 1N HCl and then concentrated to a foamy solid. Flash chromatography (silica, 18:10:1:1 EtOAc/EtOH/NH$_4$OH/H$_2$O) provided 34-9 as a slightly yellow solid.

TLC R$_f$ 0.49 (silica, 12:10:1:1 EtOAc/EtOH/NH$_4$OH/H$_2$O). $^1$H NMR (400 MHz, DMSO) δ 8.48 (bt, 1H), 7.72 (d, J=8 Hz, 2H), 7.55 (bs, 1H), 7.28 (d, J=8 Hz, 2H), 7.02 (d, J=7 Hz, 1H), 6.37 (s, 1H), 6.26 (d, J=7 Hz, 1H), 4.13 (s, 1H), 3.54 (m, 3H), 3.37 (m, 2H), 2.94 (m, 3H), 2.73 (t, J=7 Hz, 2H), 2.6 (t, J=6 Hz, 2H), 2.3 (m, 3H), 2.02 (m, 1H), 1.89 (m, 2H), 1.75 (m, 2H), 1.49 (m, 1H), 1.37 (m, 1H), 1.05 (m, 1H), 0.95 (s, 3H), 0.66 (s, 3H).

SCHEME 35

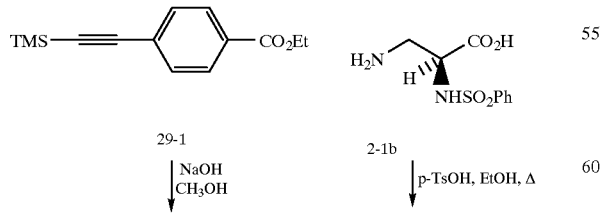

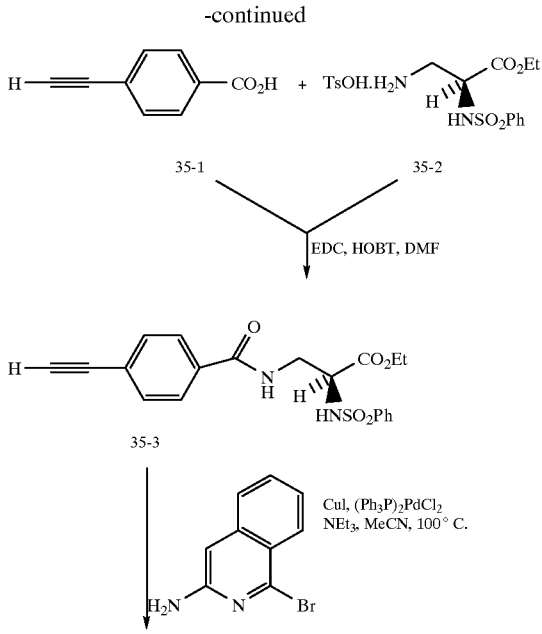

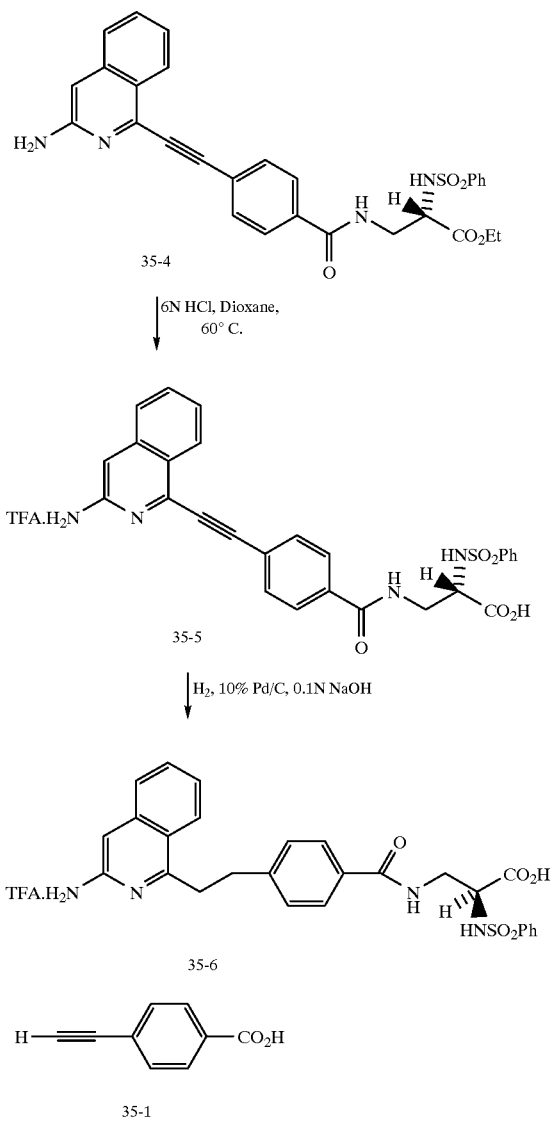

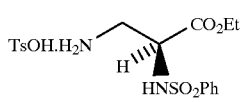

Ethyl 2(S)-phenylsulfonylamino-β-alanine p-toluenesulfonate (35-2)

Acid 2-1 b (13.20 g, 54.1 mmol) was suspended in 500 mL EtOH, p-TsOH·H₂O (11.3 g, 59 mmol) was added and the mixture was heated at reflux overnight. After distilling off the solvent, fresh EtOH was added and distilled off, then more EtOH was added and the mixture was distilled to 100 mL at which point 800 mL ether was added. After cooling to 4°, solvent was decanted from the gum which was rinsed with additional ether, and dried, providing 35-2 as a hygroscopic glass. Additional 35-2 was recovered from the solvent phase by concentration and triturating with ether (2×).

$^1$H NMR (400 MHz, D$_2$O) δ 7.91 (d, J=8 Hz, 2H), 7.75 (t, J=8 Hz, 1H), 7.70 (d, J=8 Hz, 2H), 7.65 (t, J=8 Hz, 2H), 7.37 (d, J=8 Hz, 2H), 4.42 (dd, J=10, 4 Hz, 1H), 3.86 (t, J=7 Hz, 2H), 3.50 (dd, J=13,5 Hz, 1H), 3.20 (dd, J=13, 10 Hz, 1h), 2.40 (s, 3H), 0.99 (t, J=7 Hz, 3H).

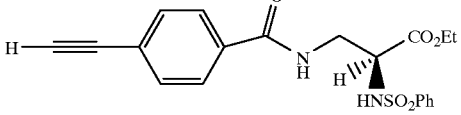

4-Ethynylbenzoyl-2(S)-phenylsulfonylamino-β-alanine ethyl ester (35-3)

4-Ethynylbenzoic acid (35-1) (3.10 g, 21.2 mmol), 35-2 (8.58 g, 19.3 mmol), NMM (8.49 mL, 7.72 mmol), HOBT (3.39 g, 25.1 mmol), and EDC (4.81 g, 25.1 mmol) were combined in 96 mL DMF and stirred overnight. The reaction was concentrated, residue was diluted with EtOAc and washed with water (2×) and brine, dried (Na$_2$SO$_4$), filtered, and concentrated. Flash chromatography (silica, 45–50% EtOAc/Hexane) gave 35-3 as a white solid.

TLC R$_f$ 0.27 (silica, 45% EtOAc/Hexane). $^1$H-NMR (300 MHz, d6-DMSO) δ 8.63 (t, J=6 Hz, 1H), 8.47 (br s, 1H), 7.75 (m, 4H), 7.52 (m, 5H), 4.39 (s, 1H), 4.11 (t, J=7 Hz, 1H), 3.78 (q, J=7 Hz, 2H), 3.44 (m, 3H), 0.94 (t, J=7 Hz, 3H).

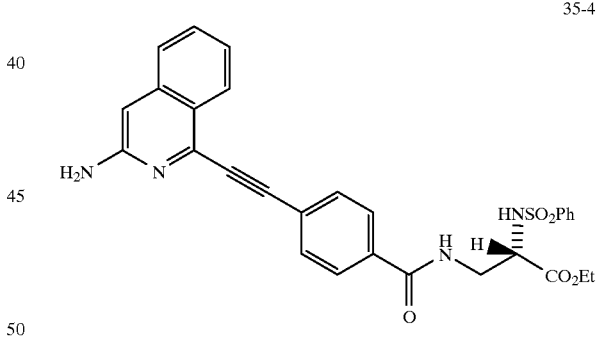

4-[(3-Aminoisoquinolin-1-yl)ethynyl]benzoyl-2(S)-phenylsulfonylamino-β-alanine ethyl ester (35-4)

Ethyl ester 35-3 (0.50 g, 1.25 mmol), 3-amino-1-bromoisoquinoline (0.279 g, 1.25 mmol), triethylamine (0.697 mL, 5.00 mmol), CuI (10 mg, 0.053 mmol), and (Ph$_3$P)$_2$PdCl$_2$ (20 mg, 0.028 mmol) were combined in 5 mL acetonitrile in a sealed pressure tube under Ar and heated to 100° C. overnight. The dark solution was cooled and diluted with EtOAc, then washed with water (2×) and brine, dried (MgSO$_4$), filtered, and concentrated. Flash chromatography (silica, 75% EtOAc/Hexane) gave 35-4 as a greenish foam.

TLC R$_f$ 0.21 (silica, 75% EtOAc/Hexane). $^1$H NMR (400 MHz, CDCl$_3$) δ 8.29 (d, J=8 Hz, 1H), 7.88 (d, J=9 Hz, 2H), 7.82 (d, J=8 Hz, 2H), 7.77 (d, J=8 Hz, 2H), 7.55 (m, 5H), 7.35 (tm, J=7 Hz, 1H), 7.27 (s, 1H), 6.80 (s, 2H), 5.80 (br s, 1H), 4.56 (s, 2H), 4.11 (m, 3H), 3.97 (m, 1H), 3.68 (m, 1H), 1.17 (t, J=7 Hz, 3H).

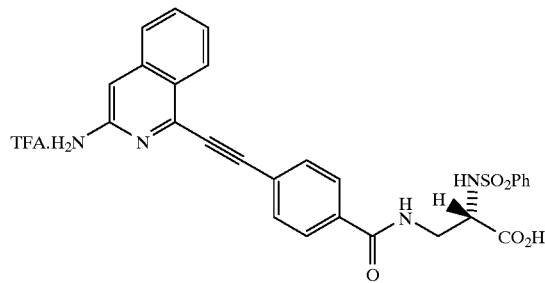

35-5

4-[(3-Aminoisoquinolin-1-yl)ethynyl]benzoyl-2(S)-phenylsulfonylamino-β-alanine trifluoroacetate (35-5)

A solution of ester 35-4 (0.46 g, 0.85 mmol) in dioxane (4 mL) and 6N HCl (8.5 mL) was heated to 60° C. overnight. Concentration yielded an orange solid. Prep. HPLC ($C_{18}$, 0.1% TFA $H_2O/CH_3CN$) followed by lyophilization gave trifluoroacetate 35-5 as an orange solid.

TLC $R_f$ 0.25 (silica, 33:20:1:1 EtOAc:EtOH:$NH_4OH$:$H_2O$). $^1H$ NMR (400 MHz, $CD_3OD$) δ 8.27 (dm, J=9 Hz, 1H), 7.87 (m, 6H), 7.68 (m, 2H), 7.50 (m, 4H), 7.15 (s, 1H), 4.24 (dd, J=9, 5 Hz, 1H), 3.79 (m, 1H), 3.51 (m, 1H).

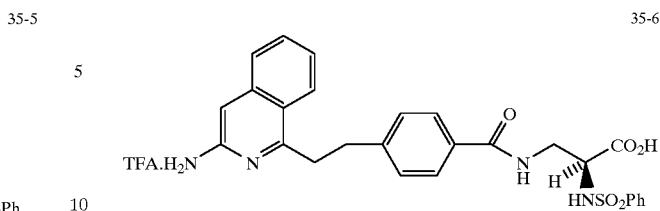

35-6

4-[2-(3-Aminoisoquinolin-1-yl)ethyl]benzoyl-2(S)-phenylsulfonylamino-β-alanine trifluoroacetate (35-6)

A mixture of acetylene 35-5 (0.085 g, 0.13 mmol) and 10% palladium on carbon (40 mg) in aqueous 0.1N NaOH was stirred under a hydrogen balloon overnight. The suspension was filtered through celite and concentrated to a dark oil. Prep. HPLC ($C_{18}$, 0.1% TFA $H_2O/CH_3CN$) followed by lyophilization gave 35-6 as a fluffy, yellow solid.

TLC $R_f$ 0.51 (silica, 22:1:1 iPrOH/$NH_4OH$/$H_2O$). $^1H$ NMR (400 MHz, $d_6$-DMSO) δ 8.40 (t, J=6 Hz, 1H), 8.22 (d, J=9 Hz, 1H), 8.14 (d, J=9 Hz, 1H), 7.75 (d, J=7 Hz, 2H), 7.68 (m, 3H), 7.60 (m, 1H), 7.52 (m, 1H), 7.45 (m, 2H), 7.38 (d, J=8 Hz, 2H), 7.28 (t, J=7 Hz, 1H), 6.86 (br, s, 1H), 4.04 (m, 1H), 3.35 (m), 3.11 (t, J=8 Hz, 2H).

SCHEME 36

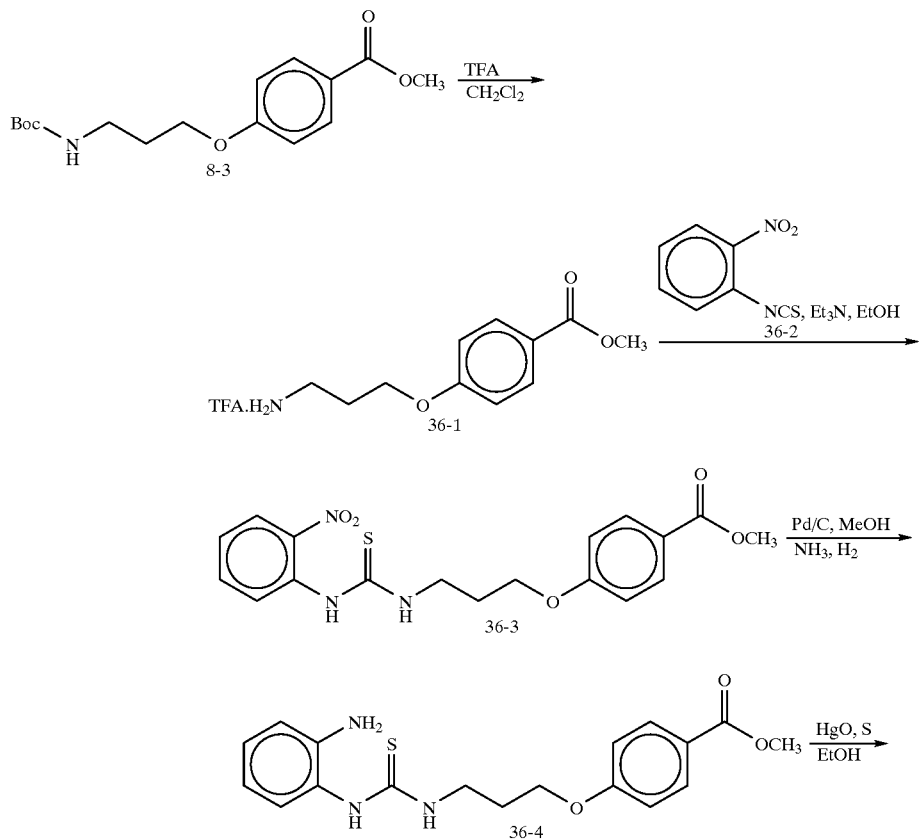

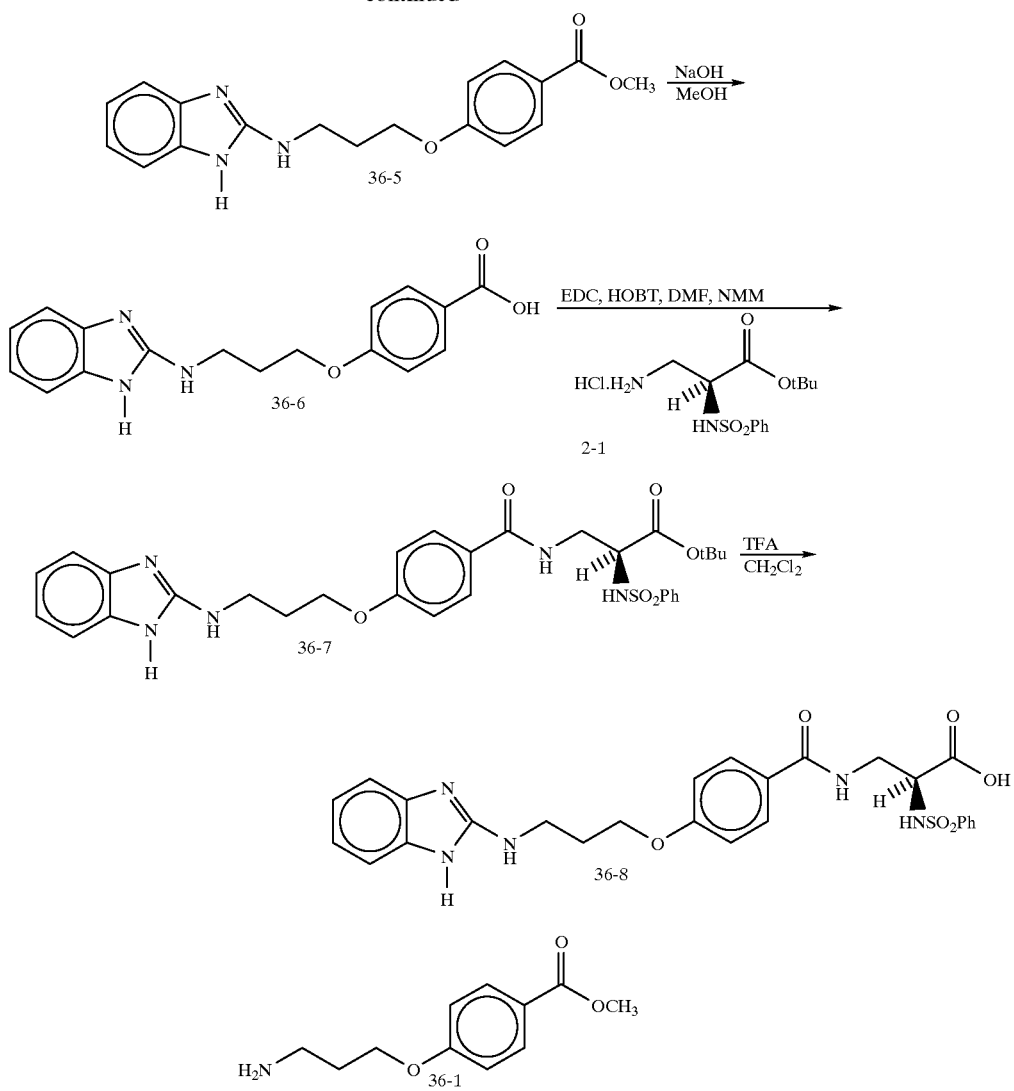

4-(3-aminopropoxy)benzoic acid methyl ester trifluoroacetate (36-1)

A CH$_2$Cl$_2$ solution (25 mL) of 8-3 (2.8 g, 8.97 mmol) and TFA (5 mL) was stirred under ambient conditions for 2 hr. The reaction was concentrated and the residue azeotroped with toluene to give a sticky solid which was triturated with hexane/ether (1:1) to provide 36-1 as a solid.

$^1$H NMR (400 MHz, CD$_3$OD) δ 7.97 (d, J=8 Hz, 2H), 7.02 (d, J=8 Hz, 2H), 4.19 (t, J=7 Hz, 2H), 3.86 (s, 3H), 3.16 (t, J=7 Hz, 2H), 2.17 (m, 2H).

An ethanol solution (20 mL) of 36-1 (2.65 g, 8.19 mmol), 36-2 (1.47 g, 8.19 mmol) (Lancaster), and Et$_3$N (2.28 mL, 16.4 mmol) was stirred under ambient conditions for 18 h. The reaction was concentrated and the residue purified by flash chromatography (silica, 19:1 CH$_2$Cl$_2$/acetone) to provide 36-3 as a yellow foam.

R$_f$ 0.23 (silica, 19:1 CH$_2$Cl$_2$/acetone). $^1$H NMR (400 MHz, CDCl$_3$) δ 8.14 (dd, J=8, 2 Hz, 1H), 7.96 (d, J=8 Hz, 2H), 7.58 (m, 1H), 7.23 (m, 1H), 6.81–6.87 (m, 3H), 4.17 (t, J=7 Hz, 2H), 3.89 (m, 5H), 2.22 (m, 2H).

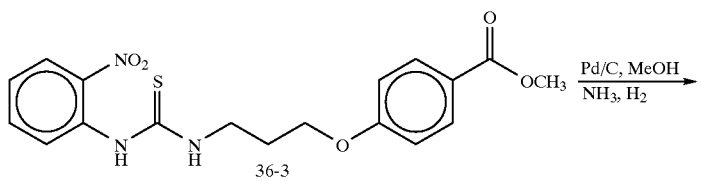

4-[3-[3-(2-nitrophenyl)thioureido]propoxy]benzoic acid methyl ester (36-3)

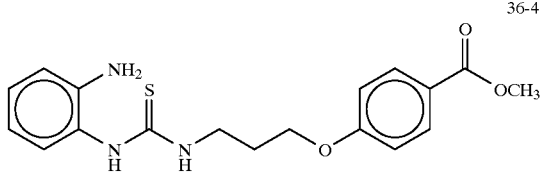

4-[3-[3-(2-aminophenyl)thioureido]propoxy]benzoic acid methyl ester (36-4)

A methanol solution (150 mL) of 36-3 (3.15 g, 8.08 mmol) was saturated with $NH_3$. 10% Pd/C (2 g) was added and the mixture hydrogenated at 1 atm for 4 h. Filtration and concentration provided 36-4 as a purple solid.

$R_f$ 0.18 (silica, 19:1 $CH_2Cl_2$/acetone). $^1$H NMR (400 MHz, $CDCl_3$) δ 7.92 (d, J=8 Hz, 2H), 7.17 (m, 1H), 7.07 (m, 1H), 6.72–6.79 (m, 2H), 6.62 (d, J=8 Hz, 2H), 4.05 (t, J=7 Hz, 2H), 3.83–3.89 (m, 5H), 2.11 (m, 2H).

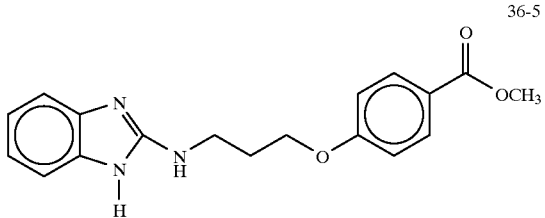

4-[3-[N-(1H-Benzimidazol-2-yl)amino]propoxy]benzoic acid methyl ester (36-5)

A mixture of 36-4 (2.5 g, 7.0 mmol), HgO (3.0 g, 13.9 mmol), sulfur (42 mg) and EtOH (50 mL) was refluxed for 2.5 h. Filtration and concentration gave a brown gum which was purified by flash chromatography (silica, 9:1 $CH_2Cl_2$/$CH_3OH$) to provide 36-5 as a tan solid.

$R_f$ 0.29 (silica, 9:1 $CH_2Cl_2$/$CH_3OH$). $^1$H NMR (400 MHz, $CD_3OD$) δ 7.94 (d, J=9 Hz, 2H), 7.18 (m, 2H), 7.00 (d, J=9 Hz, 2H), 6.96 (m, 2H), 4.19 (t, J=6 Hz, 2H), 3.86 (s, 3H), 3.58 (t, J=6 Hz, 2H), 2.16 (m, 2H).

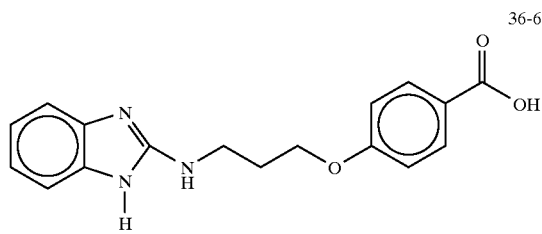

4-[3-[N-(1H.Benzimidazol-2-yl)aminol]propoxyl]benzoic acid (36-6)

A methanol solution (50 mL) of 4-5 (1.3 g, 4.0 mmol) and 1N NaOH (20 mL, 20 mmol) was stirred at 50° C. for 4 h. The reaction was concentrated and the residue acidified with 1M $NaHSO_4$ solution to provide 4-6 as a beige colored solid.

$^1$H NMR (400 MHz, $CD_3OD$) δ 7.91 (d, J=9 Hz, 2H), 7.32 (m, 2H), 7.20 (m, 2H), 6.95 (t, J=9 Hz 2H), 4.21 (t, J=6 Hz, 2H), 3.62 (t, J=6 Hz, 2H), 2.22 (m, 2H).

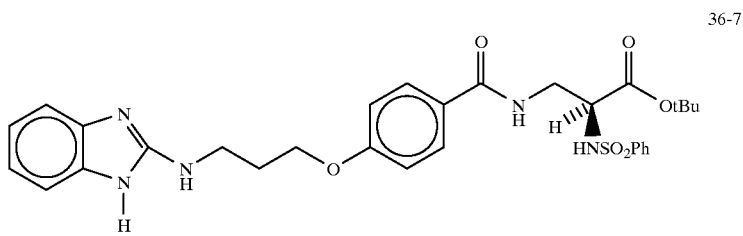

4-[3-[N-(1H-Benzimidazol-2-yl)amino]propoxy]benzoyl-2 (S)-phenylsulfonylamino-β-alanine t-butyl ester (36-7)

A DMF solution (10 mL) of 36-6 (311 mg, 1.0 mmol), 2-1 (370 mg, 1.1 mmol), HOBT (168 mg, 1.1 mmol), NMM (330 μl, 3.0 mmol) and EDC (211 mg, 1.1 mmol) was stirred under ambient conditions for 18 h. Concentration and flash chromatography (silica, 85:15 EtOAc/$CH_3OH$) gave 36-7 as a pale yellow foam.

$R_f$ 0.20 (silica, 85:15 EtOAc/$CH_3OH$). $^1$H NMR (400 MHz, $CD_3OD$) δ 7.83 (d, J=8 Hz, 2H), 7.73 (d, J=9 Hz, 2H), 7.46–7.54 (m, 3H), 7.26–7.30.(m, 2H), 7.10–7.13 (m, 2H), 6.98 (d, J=9 Hz, 2H), 4.20 (m, 2H), 3.63 (m, 3H), 3.44 (m, 1H), 3.31 (m, 1H), 2.19 (m, 2H), 1.23 (s, 9H).

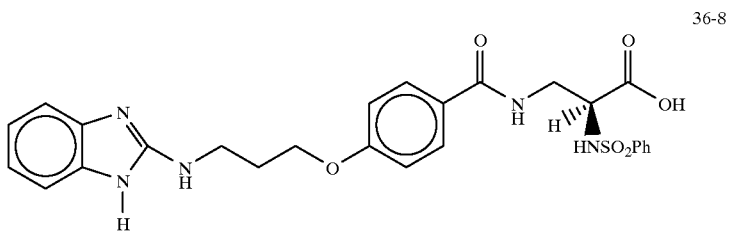

4-[3-[N-(1H-Benzimidazol-2-yl)amino]propoxy]benzoyl-2 (S)-phenylsulfonylamino-β-alanine (36-8)

A CH$_2$Cl$_2$solution (20 mL) of 36-7 (580 mg, 0.97 mmol) and TFA (5 mL) was stirred under ambient conditions for 2 h and at 50° C. for 2 h. Concentration and flash chromatography (silica, 9:0.5:0.5 EtOH/H$_2$O/NH$_4$OH) gave 36-8 as a pale yellow solid.

R$_f$ 0.29 (silica 9.8:0:1:0.1 EtOH/H$_2$O/NH$_4$OH). $^1$H NMR (400 MHz, CD$_3$OD) δ 7.83 (m, 2H), 7.76 (d, J=9 Hz, 2H), 7.32–7.34 (m, 3H), 7.17–7.19 (m, 2H), 6.99 (d, J=9 Hz, 2H), 6.85–6.88 (m, 2H), 4.20 (t, J=6 Hz, 2H), 3.58–3.65 (m, 4H), 3.36 (m, H), 2.16 (m, 2H).

SCHEME 37

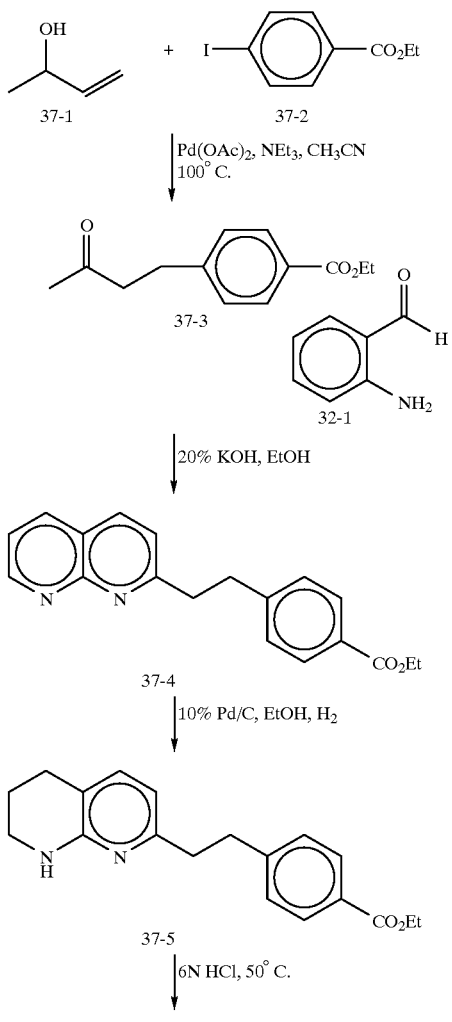

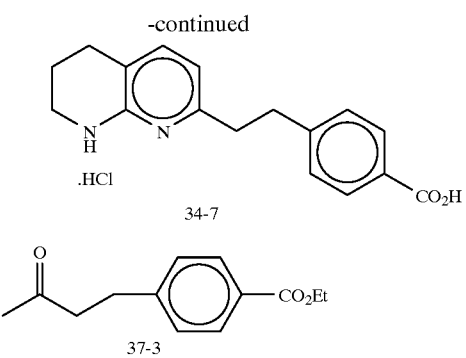

Ethyl-4-(2-butanene)benzoate (37-3)

3-Buten-2-ol 37-1 (2.15 mL, 25 mmol), ethyl 4-iodobenzoate (37-2) (5.52 q, 20 mmol) and NEt$_3$ (3.5 mL, 25 mmol) were combined in 6 mL of CH$_3$CN under Ar in a pressure tube. Pd(OAc)$_2$ (19 mg, 0.08 mmol) was added and the reaction heated to 100° C. for 3 hours. The reaction was cooled, then diluted with Et$_2$O, washed with H$_2$O, 10% KHSO$_4$, sat. NaHCO$_3$ and brine, dried (MgSO$_4$) and concentrated to a yellow oil. Flash chromatography (silica, 10% EtOAc/hex) provided 37-3 as a clear oil.

TLC R$_f$ 0.23 (silica, 30% EtOAc/hex). $^1$H NMR (300 MHz, CDCl$_3$): δ 7.95 (d, J=8 Hz, 2H), 7.25 (d, J=8 Hz, 2H), 4.36 (q, J=7 Hz, 2H), 2.95 (t, J=7 Hz, 2H), 2.78 (t, J=7 Hz, 2H), 2.15 (s, 2H), 1.38 (t, J=7 Hz, 3H).

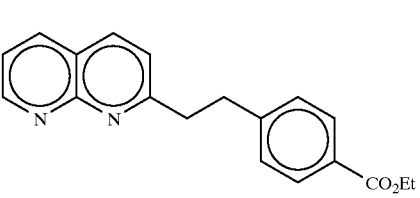

Ethyl 4-[2-(1,8-naphthyridin-7-yl)ethyl]benzoate (37-4)

An ethanol solution of (70 mL) of 37-3 (3.15 g, 14.3 mmol), 32-1 (1.75 g, 14.3 mmol) and 20% KOH (2 mL) was refluxed for 18 hours. The reaction was concentrated to dryness and the residue partitioned between EtOAc and H$_2$O. The organic layer was washed with sat. NaHCO$_3$ and brine, dried (MgSO$_4$) and concentrated to give a yellow oil. Flash chromatography (silica, 60%–80% EtOAc/hex) provided 37-4 as a yellow solid.

TLC R$_f$ 0.31 (silica, 70% EtOAc/hex). $^1$H NMR (300 MHz, CDCl$_3$) δ 9.11 (m, 1H), 8.18 (d, J=8 Hz, 1H), 8.08 (d, J=8 Hz, 1H), 7.95 (d, J=8 Hz, 2H), 7.47 (m, 1H), 7.30 (d, J=8 Hz, 2H), 4.35 (q, J=7 Hz, 2H), 3.35 (m, 4H), 1.38 (t, J=7 Hz, 3H).

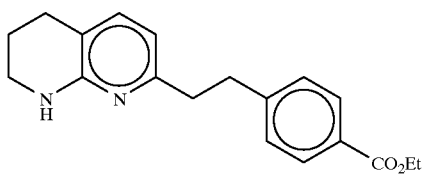

37-5

Ethyl 4-[2-(1,2,3,4-tetrahydro-1,8-naphthyridin-7-yl)ethyl] benzoate (37-5)

A mixture of 37-4 (645 mg, 2.11 mmol), 10% Pd/C (65 mg), and ethanol (10 mL) was stirred under a hydrogen atmosphere for 18 hr. Filtration through a celite pad followed by concentration provided by 37-5 as an off white solid.

TLC $R_f$ 0.75 (silica, 70% EtOAc/hex). $^1$H NMR (300 MHz, CDCl$_3$) δ 7.94 (d, J=8 Hz, 2H), 7.26 (d, J=8 Hz, 2H), 7.03 (d, J=7 Hz, 1H), 6.28 (d, J=7 Hz, 1H), 4.81 (s, 1H), 4.35 (q, J=7 Hz, 2H), 3.40 (m, 2H), 3.03 (m, 2H), 2.84 (m, 2H), 2.69 (t, J=6 Hz, 2H), 1.93 (t, J=6 Hz, 2H), 1.38 (t, J=7 Hz, 3H).

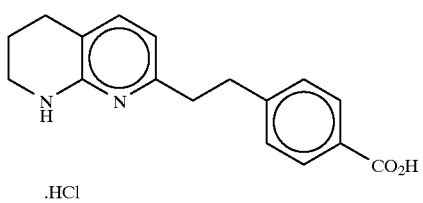

34-7

4-[2-(1,2,3,4-Tetrahydro-1,8-naphthyridin-7-yl)ethyl] benzoic acid hydrochloride (34-7)

Ester 37-5 (680 mg, 2.11 mmol) in 10 mL 6N HCl was heated to 50° C. for 18 hours. Concentration provided 34-7 as a yellow solid.

$^1$H NMR (300 MHz, CD$_3$OD) δ 7.93 (d, J=8 Hz, 2H), 7.52 (d, J=8 Hz, 1H), 7.31 (d, J=8 Hz, 2H), 6.54 (d, J=8 Hz, 1H), 3.48 (t, J=5 Hz, 2H), 3.03 (m, 4H), 2.79 (t, J=6 Hz, 2H), 1.93 (t, J=6 Hz, 2H).

The test procedures employed to measure the bone resorption inhibiting activity of the compounds of the present invention are described below.

BONE RESORPTION-PIT ASSAY

When osteoclasts engage in bone resorption, they will literally cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive cross sections (4.4×4.4×0.2 mm) of bovine femur were cut from the diaphysis with a low-speed diamond saw (Isomet, Beuhler, Ltd., Lake Bluff, Ill.) by the method of Arnett and Dempter. *Endocrinology*, 120: 602–608.

Prior to incubation with osteoclasts, slices were rehydrated in 0.1 ml complete medium 199 in a 48-well plate (Costar, Cambridge, Mass.) overnight in the presence of twice the desired dose of compound being tested.

Osteoclasts were isolated from the long bones of 1 to 3-day-old rats (Sprague-Dawley) by adaptations of methods used by Chambers, et al., *J. Cell Sci.*, 66: 383–399.

Femora, tibiae, and humeri were split and minced with scalpel blades into 2–5 ml Medium 199 (GIBCO, New York). The resulting suspension was gently pipetted (60 times with a wide-bore pipet and then aliquoted onto petri dished (Costar) or bone slices (0.1 ml per slice). Cells were allowed to settle for 30–40 minutes at 37° C. in moist $CO_2$-air before gently washing and reincubation in undiluted incubation medium. Osteoclast yields varied from 300 to 1400 per rat and typically comprised 1% or less of the total cell population.

Osteoclasts were counted at the day of isolation and after 1 day of incubation by phase-constrast microscopy (Nikon Diaphot). Total attached cells were counted 50–70 h. after isolation with a Coulter counter (model ZM, Coulter Electronics, Inc., Hialeah, Fla.). Cell counts of controls varied from $3.352 \times 10^4$ to $2.322 \times 10^5$ per well. Counting mononuclear cells at the time of isolation was not practical because of matrix and cell debris that could not be completely eliminated.

Bone slices exposed to osteoclasts for 20 h. after isolation were processed for staining by ultrasonication (twofold, 15 s, Branson) in 0.25M ammonium hydroxide before fixation (20 minutes) in 2.5% glutaraldehyde, 0.1M cacodylate, pH 7.4 (EM Supplies, Fort Washington, Pa.). Samples were dehydrated in ethanol (40, 70, and 100%; 5 minutes), air dried for 2 h., and then stained for 4 minutes with filtered 1% toluidine blue and 1% borax (Sigma, St. Louis, Mo.). Samples used to count osteoclasts were processed as earlier without ultrasonication in ammonium hydroxide.

A fluorescence microscope (Microphot, Nikon) was adapted for reflected light microscopy by inserting a λ/4 plate between cross polarizers in the epi mode. Fluorescence objectives of long working distance with adjustable correction collars (10×,20×, Nikon) were fitted with rotable λ/4 plates (Polaroid Corp., Massachusetts) mounted as the front element. Correction collars were necessary 20×objectives and higher to correct for the presence of the λ/4 plate and the absence of a coverslip. Coverslips were not used to eliminate stray reflections below the λ/4 plate. Immersion oil (Nikon) was added between the objective front lens and λ/4 to minimize reflections at this interface. Oil was not placed between objective and specimen.

Bone slices were scanned for resorption pits by rotating the λ/4 plate 0°–45° with respect to the plane of polarization in epi-tungsten illumination. Alternatively, Hg illumination (HBO 100w, Nikon) was used with the λ/4 plate fixed at 45° while intermittently viewing stained images by transmission brightfield microscopy with an NCB 10 filter (Nikon).

Quantitation of resorbed areas of bone slices examined by bright-field, RLM, and SEM was achieved through digital image processing (Magiscan 2A, Joyce Loebl, N.Y.) of video images (Newvicon or SIT, Dage-MTI, Inc. Michigan City, Ind.) fed through a NTSC/PAL digital standards converter (CEL P156, James Grunder and Assoc., Inc., Mission, Kans.).

Osteoclasts were processed for immunofluorescence by briefly rinsing coverslips in buffer S (60 mM Pipes, pH 6.9; 25 mM Hepes; 10 mM EGTA; and 2 mM $MgCl_2$) at 37° C. and then fixing for 2 minutes in buffer S+10% formaldehyde, pH 7.0. Cells were permeabilized in buffer S+0.5% Triton X-100 and then rinsed. Specimens were incubated (30 minutes) in appropriate antibody or rhodamine-phalloidine (Molecular Probes, Eugene, Oreg.) followed by fluorescein goat antirabbit antibody (Cappel).

The bone slice assay is used to examine the effect of the compound of interest on the activity of isolated osteoclasts from rat long bones.

The number of resorption pits formed by osteoclasts after 1 day on consecutive cross sections of bovine femur was first compared to control samples by the method of Arnett and Dempster, Endocrinology 120:602–608, and then plotted as a function of concentration of the compound of interest.

The appropriateness of extrapolating data from this assay to utility and use in mammalian (including himan) disease states is supported by the teaching found in Sato, M., et al., *Journal of Bone and Mineral Research*, Vol. 5, No. 1, 1990. That article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB ASSAY

Duong et al., *J. Bone Miner. Res.*, 8:S 378, describe a system for expressing the human integrin $\alpha_v\beta_3$. It has been suggested that the integrin is involved in the attachment of osteoclasts to bone matrix, since antibodies against the integrin, or RGD-containing molecules, such as echistatin (European Publication 382 451), can effectively block bone resorption.

Reaction Mixture:
1. 175 μl TBS buffer (50 mM Tris-HCl pH 7.2, 150 mM NaCl, 1% BSA, 1 mM CaCl$_2$, 1 mM MgCl2).
2. 25 μl cell extract (dilute with 100 mM octylgiucoside buffer to give 2000 cpm/25 μl).
3. $^{125}$I-echistatin (25 μ/50,000 cpm) (see EP 382 451).
4. 25 μl buffer (total binding) or unlabeled echistatin (non-specific binding).

The reaction mixture was then incubated for 1 h at room temp. The unbound and the bound $\alpha_{v\ \beta3}$ were separated by filtration using a Skatron Cell Harvester. The filters (prewet in 1.5% polyethyleneimine for 10 mins) were then washed with the wash buffer (50 mM Tris HCl, 1 mM CaCl$_2$/MgCl$_2$, pH 7.2). The filter was then counted in a gamma counter.

OCFORM ASSAY

Osteoblast-like cells (1.8 cells), originally derived from mouse calvaria, are plated in CORNING 24 well tissue culture plates in α MEM medium containing ribo- and deoxyribonucleosides, 10% fetal bovine serum and penicillin-streptomycin. Cells are seeded at 40,000/well in the morning. In the afternoon, bone marrow cells are prepared from six week old male Balb/C mice as follows:

Mice are sacrificed, tibiae removed and placed in the above medium. The ends are cut off and the marrow is flushed out of the cavity into a tube with a 1 mL syringe with a 27.5 guage needle. The marrow is suspended by pipetting up and down with a glass pasteur pipet. The suspension is passed through two layers of approximately 400 μm mesh stainless steel cloth. The resulting suspension is centrifuged at 350×g for seven minutes. The pellet is resuspended, and a sample is diluted in 2% acetic acid to lyse the red cells. The remaining cells are counted in a hemacytometer. The cells are pelleted and resuspended at 1×10$^6$ cells/mL. 50 μL is added to each well of 1.8 cells to yield 50,000 cells/well and 1,25-dihydroxy-vitamin D$_3$(D$_3$) is added to each well to a final concentration of 10 nM. The cultures are incubated at 37° C. in a humidified, 5% CO$_2$ atmosphere. After 48 h, the medium is changed. 72 h after the addition of bone marrow, test compounds are added with fresh medium containing D$_3$ to triplicate wells. Compounds are added again after 48 h with fresh medium containing D$_3$. After an additional 24 h the medium is removed, cells are fixed with 10% formaldehyde in phosphate buffered saline for 10 minutes at room temperature, followed by a 1–2 minute treatment with ethanol:acetone (1:1) and air dried. The cells are then stained for tartrate resistant acid phosphatase as follows:

The cells are stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS -MX phosphate. After staining, the plates are washed extensively with dionized water and air dried. The number of multinucleated, positively staining cells are counted in each well.

The compounds of the invention have values in the range 0.5–500 nM in EIB and 1–1000 nM in OCFORM.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula

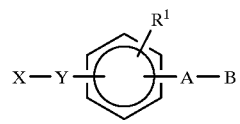

wherein

X is selected from the group consisting of

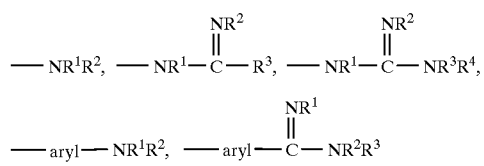

Y is selected from the group consisting of
C$_{1-8}$ alkylene,
(CH$_2$)$_m$—C≡C(CH$_2$)$_n$,
(CH$_2$)$_m$CR$^1$=CR$^2$(CH$_2$)$_n$,
(CH$_2$)$_m$CR$^1$=CR$^2$(CH$_2$)$_n$O,
C$_{0-8}$ alkylene-NR$^3$—CO—C$_{O-8}$ alkylene,
C$_{0-8}$ alkylene—O—C$_{0-8}$ alkylene,
C$_{0-8}$ alkylene-NR$^3$—C$_{0-8}$ alkylene and
C$_{0-8}$ alkylene-NR$^3$—C$_{0-8}$ alkylene-O—;

A is selected from the group consisting of

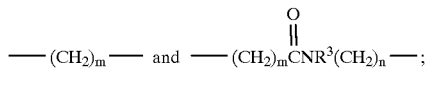

B is

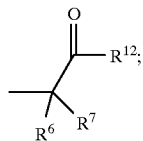

$R^1$, $R^2$, $R^3$ and $R^4$ are each independently selected from the group consisting of
hydrogen,
$C_{1-4}$ alkoxy $C_{0-6}$ alkyl,
$C_{1-4}$ alkoxycarbonyl $C_{0-6}$ alkyl,
$C_{1-6}$ alkylanmino $C_{0-8}$ alkyl,
$C_{1-6}$ dialkylamino $C_{0-8}$ alkyl,
amino $C_{0-8}$ alkyl and
aryl $C_{0-8}$ alkyl;
$R^5$ is selected from the group consisting of
hydrogen,
$C_{1-4}$ alkoxy $C_{0-6}$ alkyl,
$C_{1-4}$ alkoxycarbonyl $C_{0-6}$ alkyl,
$C_{1-6}$ alkylamino $C_{0-8}$ alkyl,
$C_{1-6}$ dialkylamino $C_{0-8}$ alkyl,
amino $C_{0-8}$ alkyl,
oxo and
aryl $C_{0-8}$ alkyl;
$R^6$ and $R^7$ are each independently selected from the group consisting of:
hydrogen,
$C_{0-6}$ alkylamino $C_{0-6}$ alkyl,
$C_{0-6}$ dialkylamino $C_{0-6}$ alkyl,
aryl $C_{0-6}$ alkyloxycarbonylamino $C_{0-6}$ alkyl,
aryl $C_{0-6}$ alkylsulfonylamino $C_{0-6}$ alkyl,
camphorsulfonylamino, and
aryl $C_{0-6}$ alkylcarbonylamino $C_{0-6}$ alkyl;
$R^{12}$ is selected from the group consisting of
hydroxy,
$C_{1-8}$ alkyloxy,
$C_{1-6}$ dialkylamiocarbonylmethoxy and
aryl $C_{1-6}$ dialkylaminocarbonylmethoxy; and
m and n are integers independently chosen from 0–6; provided that when the compound is

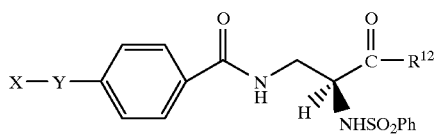

wherein $R^{12}$ is hydroxy or $C_{1-4}$ alkyloxy, then X-Y is not
$NH_2$—$(CH_2)_2$—NH—CO—, BOC—HN—$(CH_2)_2$—NH—CO—, or

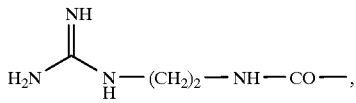

and the pharmaceutically acceptable salts thereof.

2. A compound of claim 1 having the formula

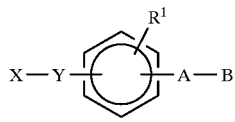

wherein
X is selected from the group consisting of

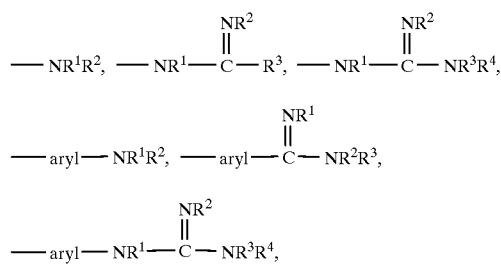

and the pharmaceutically acceptable salts thereof.

3. The compound of claim 2, or a pharmaceutically acceptable salt thereof, wherein
X is selected from the group consisting of

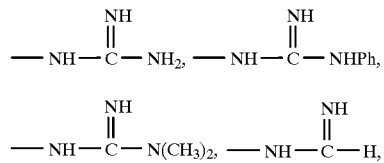

Y is selected from the group consisting of
$C_{1-2}$ alkylene,
C≡C—,
$C_{0-2}$ alkylene-NH—CO—,
$C_{0-5}$ alkylene-O—$C_{0-1}$ alkylene and
—NH—$C_{2-4}$ alkylene-O—;
A is selected from the group consisting of

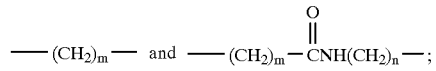

$R^1$ is selected from the group consisting of
hydrogen and
$C_{1-4}$ alkoxy;
$R^6$ and $R^7$ are each independently selected from the group consisting of
hydrogen,
—NHCbz, —NHSO₂Ph,
—NHC(O)—Ph,
camphorsulfonylamino; and
—N(CH₃)—SO₂Ph; and m and n are integers independently chosen from 0–1.

4. The compound of claim 3, or a pharmaceutically acceptable salt thereof, selected from the group of:

4-(2-Guanidoethyloxy)benzoyl-2(S)-benzyloxycarbonylamino-β-alanine, 4-(2-Guanidoethyloxy)benzoyl-2(S)-phenylsulfonylamino-β-alanine, 2(S)-Phenylsulfonylamino-3-propionic acid, 2(S)-(N-Benzyloxycarbonylaniino)-3-propionic acid, 4-(3-Guanidinoinpropyloxy)benzoyl-2-(S)-phenylsulfonylamino-β-alanine, 4-(3-Formamidinopropyloxy)benzoyl-2-(S)-phenylsulfonylamino-β-alanine, 3-Methoxy-4-(3-guanidinopropyloxy)benzoyl-2(S)-phenylsulfonyl-amino-β-alanine, 3-Methoxy-4-(3-aminopropyloxy)benzoyl-2(S)-phenylsulfonylamino-β-alanine, 3-benzoyl-2(S)-phenylsulfonylamino-β-alanine, 4-benzoyl-2(S)-phenylsulfonylamino-β-alanine, 4-benzoyl-2(S)-phenylsulfonyl-amino-β-alanine, 4-(Guanidinophen-3-yloxy)benzoyl-2(S)-phenylsulfonylamino-β-alanine, 4-benzoyl-2(S)-phenylsulfonylamino-β-alanine, and 3-benzoyl-2(S)-phenylsulfonyl-amino-β-alanine.

5. A method of inhibiting the bone resorption activity of mammalian osteoclast cells comprising the step of administering a pharmacologically effective amount of a compound of claim 2.

6. A composition for inhibiting bone resorption activity of mammalian osteoclast cells comprising a pharmacologically effective amount of the compound of claim 2 and a pharmaceutically acceptable carrier.

7. A method of inhibiting the bone resorption activity of mammalian osteoclast cells comprising the step of administering a pharmacologically effective amount of a compound of claim 4.

8. A composition for inhibiting bone resorption activity of mammalian osteoclast cells comprising a pharmacologically effective amount of a compound of claim 4 and a pharmaceutically acceptable carrier.

9. A method for inhibiting tumor metastasis in a patient comprising the step of administering a pharamacologically effective amount of a compound of claim 2.

10. A composition for inhibiting tumor metastasis in a patient comprising a pharmacologically effective amount of a compound of claim 2 and a pharmaceutically acceptable carrier.

11. A method for inhibiting restenosis in a patient comprising the step of administering a pharamacologically effective amount of a compound of claim 2.

12. A composition for inhibiting restenosis in a patient comprising a pharmacologically effective amount of a compound of claim 2 and a pharmaceutically acceptable carier.

13. A method for inhibiting diabetic retinopathy in a patient comprising the step of administering a pharamacologically effective amount of a compound of claim 2.

14. A composition for inhibiting diabetic retinopathy in a patient comprising a pharmacologically effective amount of a compound of claim 2 and a pharmaceutically acceptable carrier.

* * * * *

UNITED STATES PATENT AND TRADEMARK OFFICE
CERTIFICATE OF CORRECTION

PATENT NO. : 5,929,120

DATED : Jul. 27, 1999

INVENTOR(S) : George D. Hartman, Mark E. Duggan, William F. Hoffman, and Nathan C. Ihle It is certified that error appears in the above-identified patent and that said Letters Patent is hereby corrected as shown below:

On the Title Page:

(54) please correct the title to read as follows:

"GUANIDINO, FORMAMIDINO, AMINO AND RELATED COMPOUNDS FOR INHIBITING OSTEOCLAST-MEDIATED BONE RESORPTION"

Column 1, lines 1-4,

"GUAINIDINO, FORMAMIDINO, AMINO AND RELATED COMPOUNDS FOR INHIBITING OSTEOCLAST-MEDIATERD BONE RESORPTION" should read as:

"GUANIDINO, FORMAMIDINO, AMINO AND RELATED COMPOUNDS FOR INHIBITING OSTEOCLAST-MEDIATED BONE RESORPTION."

Signed and Sealed this

Twenty-first Day of March, 2000

Attest:

Q. TODD DICKINSON

Attesting Officer

Commissioner of Patents and Trademarks